(12) United States Patent
Sawhney et al.

(10) Patent No.: US 8,003,705 B2
(45) Date of Patent: Aug. 23, 2011

(54) BIOCOMPATIBLE HYDROGELS MADE WITH SMALL MOLECULE PRECURSORS

(75) Inventors: Amarpreet S. Sawhney, Lexington, MA (US); Steven Bennett, Cheshire, CT (US); Peter G. Edelman, Maple Grove, MN (US)

(73) Assignee: Incept LLC, Bedford, MA (US)

( * ) Notice: Subject to any disclaimer, the term of this patent is extended or adjusted under 35 U.S.C. 154(b) by 527 days.

(21) Appl. No.: 12/156,085

(22) Filed: May 29, 2008

(65) Prior Publication Data

US 2008/0260802 A1    Oct. 23, 2008

Related U.S. Application Data

(63) Continuation-in-part of application No. 12/069,821, filed on Feb. 13, 2008, now Pat. No. 7,592,418, which is a continuation of application No. 11/293,892, filed on Dec. 2, 2005, now Pat. No. 7,332,566, which is a continuation of application No. 10/010,715, filed on Nov. 9, 2001, now Pat. No. 7,009,034, which is a continuation-in-part of application No. 09/454,900, filed on Dec. 3, 1999, now Pat. No. 6,566,406, said application No. 10/010,715 is a continuation-in-part of application No. 09/147,897, filed as application No. PCT/US97/16897 on Sep. 22, 1997, now abandoned.

(60) Provisional application No. 60/110,849, filed on Dec. 4, 1998, provisional application No. 60/040,417, filed on Mar. 13, 1997, provisional application No. 60/039,904, filed on Mar. 4, 1997, provisional application No. 60/026,526, filed on Sep. 23, 1996.

(51) Int. Cl.
*A61K 47/30* (2006.01)
*A61K 47/32* (2006.01)
*A61K 47/34* (2006.01)

(52) U.S. Cl. ............ 514/772.1; 514/773; 424/422; 424/423; 424/426; 424/78.08

(58) Field of Classification Search .......... None
See application file for complete search history.

(56) References Cited

U.S. PATENT DOCUMENTS

| | | |
|---|---|---|
| 2,533,004 A | 12/1950 | Ferry et al. |
| 3,520,949 A | 7/1970 | Shepard et al. |
| 4,101,380 A | 7/1978 | Rubinstein et al. |
| 4,359,049 A | 11/1982 | Redl et al. |
| 4,414,976 A | 11/1983 | Schwarz et al. |
| 4,427,651 A | 1/1984 | Stroetmann |
| 4,565,784 A | 1/1986 | Franzblau et al. |
| 4,601,286 A | 7/1986 | Kaufman |
| 4,631,055 A | 12/1986 | Redl et al. |
| 4,631,188 A | 12/1986 | Stoy et al. |
| 4,646,730 A | 3/1987 | Schonfeld et al. |
| 4,693,887 A | 9/1987 | Shah |
| 4,717,378 A | 1/1988 | Perrault et al. |
| 4,735,616 A | 4/1988 | Eibl et al. |
| 4,740,534 A | 4/1988 | Matsuda et al. |
| 4,803,075 A | 2/1989 | Wallace et al. |
| 4,826,945 A | 5/1989 | Cohn et al. |
| 4,874,368 A | 10/1989 | Miller et al. |
| 4,902,281 A | 2/1990 | Avoy |
| 4,925,677 A | 5/1990 | Feijen |
| 4,932,942 A | 6/1990 | Maslanka |
| 4,937,270 A | 6/1990 | Hamilton et al. |
| 4,938,763 A | 7/1990 | Dunn et al. |
| 4,978,336 A | 12/1990 | Capozzi et al. |
| 4,979,959 A | 12/1990 | Guire |
| 5,030,215 A | 7/1991 | Morse et al. |
| 5,041,292 A | 8/1991 | Feijen |
| 5,093,319 A | 3/1992 | Higham et al. |
| 5,100,992 A | 3/1992 | Cohn et al. |
| 5,104,909 A | 4/1992 | Grasel et al. |
| 5,116,315 A | 5/1992 | Capozzi et al. |
| 5,143,662 A | 9/1992 | Chesterfield et al. |
| 5,160,745 A | 11/1992 | DeLuca et al. |
| 5,162,430 A | 11/1992 | Rhee et al. |
| 5,192,743 A | 3/1993 | Hsu et al. |

(Continued)

FOREIGN PATENT DOCUMENTS

EP    0246380 A3    10/1986

(Continued)

OTHER PUBLICATIONS

Sierra, "Fibrin Sealant Adhesive Systems: A Review of Their Chemistry, Material Properties and Clinical Applications," Journal of Biomaterials Applications 7:309-352 (1993).

Silver et al., "Effect of Protein Adsorption on the Blood-Contacting Response of Sulphonated Polyurethanes," Biomaterials 14:834-844 (1993) (abstract).

Smith et al., "Thrombin and Albumin Adsorption to PV A and Heparin-PV A Hydrogels. 2: Competition and Displacement," J Biomed Mater Res 27:89-95 (1993) (abstract).

Tabata et al., "Controlled Delivery Systems for Proteins Using Polyanhydride Microspheres," Pharmaceutical Research 10:487-496 (1993).

(Continued)

Primary Examiner — Christina Bradley
(74) Attorney, Agent, or Firm — Dardi & Herbert, PLLC

(57) ABSTRACT

Biocompatible crosslinked polymers, and methods for their preparation and use, are disclosed in which the biocompatible crosslinked polymers are formed from water soluble precursors having electrophilic and nucleophilic functional groups capable of reacting and crosslinking in situ. Methods for making the resulting biocompatible crosslinked polymers biodegradable, or not, are provided, as are methods for controlling the rate of degradation. The crosslinking reactions may be carried out in situ on organs or tissues or outside the body. Applications for such biocompatible crosslinked polymers and their precursors include controlled delivery of drugs, prevention of post-operative adhesions, coating of medical devices such as vascular grafts, wound dressings and surgical sealants. Visualization agents may be included with the crosslinked polymers. Embodiments that include hydrogels having isolated hydrolytically degradable esters are set forth. Embodiments including the use of low molecular weight amines to make degradable hydrogels are also set forth.

22 Claims, 30 Drawing Sheets

U.S. PATENT DOCUMENTS

| | | | |
|---|---|---|---|
| 5,213,760 A | 5/1993 | Dziabo, Jr. et al. |
| 5,213,808 A | 5/1993 | Bar-Shalom et al. |
| 5,219,564 A | 6/1993 | Zalipsky et al. |
| 5,278,202 A | 1/1994 | Dunn et al. |
| 5,281,662 A | 1/1994 | Ito et al. |
| 5,290,776 A | 3/1994 | Caulkett et al. |
| 5,292,362 A | 3/1994 | Bass et al. |
| 5,296,518 A | 3/1994 | Grasel et al. |
| 5,304,595 A | 4/1994 | Rhee et al. |
| 5,318,524 A | 6/1994 | Morse et al. |
| 5,324,775 A | 6/1994 | Rhee et al. |
| 5,328,955 A | 7/1994 | Rhee et al. |
| 5,330,768 A | 7/1994 | Park et al. |
| 5,368,563 A | 11/1994 | Lonneman et al. |
| 5,395,923 A | 3/1995 | Bui-Khac et al. |
| 5,399,351 A | 3/1995 | Leshchiner et al. |
| 5,405,607 A | 4/1995 | Epstein |
| 5,410,016 A | 4/1995 | Hubbell et al. |
| 5,413,791 A | 5/1995 | Rhee et al. |
| 5,419,491 A | 5/1995 | Breitsprecher |
| 5,423,821 A | 6/1995 | Pasque |
| 5,426,148 A | 6/1995 | Tucker |
| 5,431,639 A | 7/1995 | Shaw |
| 5,446,090 A | 8/1995 | Harris |
| 5,446,091 A | 8/1995 | Rhee et al. |
| 5,455,027 A | 10/1995 | Zalipsky et al. |
| 5,470,911 A | 11/1995 | Rhee et al. |
| 5,474,540 A | 12/1995 | Miller et al. |
| 5,475,052 A | 12/1995 | Rhee et al. |
| 5,476,909 A | 12/1995 | Kim et al. |
| 5,505,704 A | 4/1996 | Pawelka et al. |
| 5,514,379 A | 5/1996 | Weissleder et al. |
| 5,514,380 A | 5/1996 | Song et al. |
| 5,527,856 A | 6/1996 | Rhee et al. |
| 5,529,914 A | 6/1996 | Hubbell et al. |
| 5,550,187 A | 8/1996 | Rhee et al. |
| 5,550,188 A | 8/1996 | Rhee et al. |
| 5,565,519 A | 10/1996 | Rhee et al. |
| 5,567,435 A | 10/1996 | Hubbell et al. |
| 5,573,934 A | 11/1996 | Hubbell et al. |
| 5,580,923 A | 12/1996 | Yeung et al. |
| 5,583,114 A | 12/1996 | Barrows et al. |
| 5,587,175 A | 12/1996 | Viegas et al. |
| 5,605,541 A | 2/1997 | Holm |
| 5,605,938 A | 2/1997 | Roufa et al. |
| 5,612,052 A | 3/1997 | Shalaby |
| 5,614,587 A | 3/1997 | Rhee et al. |
| 5,618,563 A | 4/1997 | Berde et al. |
| 5,626,863 A | 5/1997 | Hubbell et al. |
| 5,631,322 A | 5/1997 | Veronese et al. |
| 5,643,464 A | 7/1997 | Rhee et al. |
| 5,645,583 A | 7/1997 | Villain et al. |
| 5,656,035 A | 8/1997 | Avoy |
| 5,668,236 A | 9/1997 | Engelhardt et al. |
| 5,672,622 A | 9/1997 | Hedgepeth et al. |
| 5,681,576 A | 10/1997 | Henry |
| 5,698,213 A | 12/1997 | Jamiolkowski et al. |
| 5,702,361 A | 12/1997 | Evans et al. |
| 5,714,159 A | 2/1998 | Shalaby |
| 5,733,950 A | 3/1998 | Dunn et al. |
| 5,741,223 A | 4/1998 | Janzen et al. |
| 5,744,545 A | 4/1998 | Rhee et al. |
| 5,749,968 A | 5/1998 | Melanson et al. |
| 5,752,974 A | 5/1998 | Rhee et al. |
| 5,773,025 A | 6/1998 | Baichwal |
| 5,776,493 A | 7/1998 | Barclay et al. |
| 5,786,421 A | 7/1998 | Rhee et al. |
| 5,800,541 A | 9/1998 | Rhee et al. |
| 5,801,033 A | 9/1998 | Hubbell et al. |
| 5,807,581 A | 9/1998 | Rosenblatt et al. |
| 5,810,885 A | 9/1998 | Zinger |
| 5,814,621 A | 9/1998 | Kanaya et al. |
| 5,830,178 A | 11/1998 | Jones et al. |
| 5,830,196 A | 11/1998 | Hicks |
| 5,844,023 A | 12/1998 | Tomka |
| 5,858,746 A | 1/1999 | Hubbell et al. |
| 5,863,551 A | 1/1999 | Woerly |
| 5,869,096 A | 2/1999 | Barclay et al. |
| 5,874,500 A | 2/1999 | Rhee et al. |
| 5,900,245 A | 5/1999 | Sawhney et al. |
| 5,932,462 A | 8/1999 | Harris et al. |
| 5,936,035 A | 8/1999 | Rhee et al. |
| 5,962,023 A | 10/1999 | Jamiolkowski et al. |
| 5,986,043 A | 11/1999 | Hubbell et al. |
| 5,990,193 A | 11/1999 | Russell et al. |
| 6,017,301 A | 1/2000 | Schwartz et al. |
| 6,020,326 A | 2/2000 | Roufa et al. |
| 6,033,654 A | 3/2000 | Stredronsky et al. |
| 6,051,248 A | 4/2000 | Sawhney et al. |
| 6,051,648 A | 4/2000 | Rhee et al. |
| 6,110,484 A | 8/2000 | Sierra |
| 6,124,273 A | 9/2000 | Drohan et al. |
| 6,129,761 A | 10/2000 | Hubbell |
| 6,133,325 A | 10/2000 | Schwartz et al. |
| 6,136,333 A | 10/2000 | Cohn et al. |
| 6,149,931 A | 11/2000 | Schwartz et al. |
| 6,153,211 A | 11/2000 | Hubbell et al. |
| 6,156,345 A | 12/2000 | Chudzik et al. |
| 6,156,531 A | 12/2000 | Pathak et al. |
| 6,162,241 A | 12/2000 | Coury et al. |
| 6,165,489 A | 12/2000 | Berg et al. |
| 6,166,130 A | 12/2000 | Rhee et al. |
| 6,174,645 B1 | 1/2001 | Russell et al. |
| 6,177,095 B1 | 1/2001 | Sawhney et al. |
| 6,201,065 B1 | 3/2001 | Pathak et al. |
| 6,214,966 B1 | 4/2001 | Harris |
| 6,238,403 B1 | 5/2001 | Greene, Jr. et al. |
| 6,251,382 B1 | 6/2001 | Greenwald et al. |
| 6,258,351 B1 | 7/2001 | Harris |
| 6,261,544 B1 | 7/2001 | Coury et al. |
| 6,271,278 B1 | 8/2001 | Park et al. |
| 6,277,394 B1 | 8/2001 | Sierra |
| 6,303,102 B1 | 10/2001 | Schlichte |
| 6,306,922 B1 | 10/2001 | Hubbell et al. |
| 6,312,725 B1 | 11/2001 | Wallace et al. |
| 6,323,278 B2 | 11/2001 | Rhee et al. |
| 6,348,558 B1 | 2/2002 | Harris et al. |
| 6,371,975 B2 | 4/2002 | Cruise et al. |
| 6,413,539 B1 | 7/2002 | Shalaby |
| 6,428,571 B1 | 8/2002 | Lentz et al. |
| 6,458,147 B1 | 10/2002 | Cruise et al. |
| 6,458,889 B1 | 10/2002 | Trollsas et al. |
| 6,465,001 B1 | 10/2002 | Hubbell et al. |
| 6,495,127 B1 | 12/2002 | Wallace et al. |
| 6,515,534 B2 | 2/2003 | Dabral |
| 6,566,406 B1 | 5/2003 | Pathak et al. |
| 6,610,033 B1 | 8/2003 | Melanson et al. |
| 6,632,457 B1 | 10/2003 | Sawhney |
| 6,818,018 B1 | 11/2004 | Sawhney |
| 6,958,212 B1 | 10/2005 | Hubbell et al. |
| 7,009,034 B2 | 3/2006 | Pathak et al. |
| 7,332,566 B2 | 2/2008 | Pathak et al. |
| 2001/0003126 A1 | 6/2001 | Rhee et al. |
| 2004/0076602 A1 | 4/2004 | Harris et al. |
| 2008/0095736 A1* | 4/2008 | Pathak et al. ............. 424/78.08 |

FOREIGN PATENT DOCUMENTS

| | | |
|---|---|---|
| EP | 0414848 B1 | 3/1991 |
| EP | 0732109 A1 | 9/1996 |
| EP | 0863933 B1 | 11/1996 |
| EP | 1 967 220 A2 | 9/2008 |
| JP | 3-502704 | 6/1991 |
| JP | 5-508161 | 11/1993 |
| JP | 6-508169 | 9/1994 |
| JP | 10-503102 | 3/1998 |
| WO | 89/02445 A1 | 3/1989 |
| WO | 9109641 A1 | 7/1991 |
| WO | 92/00105 A1 | 1/1992 |
| WO | 92/20349 A1 | 11/1992 |
| WO | 96/03159 A1 | 2/1996 |
| WO | 9603159 A1 | 2/1996 |
| WO | 9614095 A1 | 5/1996 |
| WO | 9719973 A1 | 5/1997 |
| WO | 9722371 A1 | 6/1997 |
| WO | 9722372 A1 | 6/1997 |
| WO | 9835631 A1 | 8/1998 |
| WO | 99/03454 A1 | 1/1999 |

| | | | |
|---|---|---|---|
| WO | 9908718 A3 | 2/1999 |
| WO | 9910022 A3 | 3/1999 |
| WO | 9914259 A1 | 3/1999 |
| WO | 9922770 A1 | 5/1999 |
| WO | 9934833 A1 | 7/1999 |
| WO | 0009087 A1 | 2/2000 |
| WO | 0033764 A1 | 6/2000 |
| WO | 0166017 A1 | 9/2001 |
| WO | 0168155 A1 | 9/2001 |

OTHER PUBLICATIONS

Vermes, "Cerebrospinal Fluid Proteins: I. Comparative Study of Concentration Methods," Arq Neuropsiquiatr 41:1-8 (1983) (abstract).
Walther et al., "Pore-Size Distributions of Cationic Polyacrylamide Hydrogels of Different Compositions Maintained at the Same Swelling Capacity", J. Macromol. Sci.-Phys. B33 (3&4):267-286 (1994).
Wang et al., "Hydrogels as Separation Agents," Advances in Polymer Science 110:67-79 (1993).
Jarrett et al., "Bioabsorbable Hydrogel Tissue Barrier: In Situ Gelation Kinetics," Soc. For Biomater., Transactions of 21st Annual Meeting: 182 (1995).
Achterberg et al., "Hydroactive Dressings and Serum Proteins: An In Vitro Study," J Wound Care, 5:79-82 (1996)(abstract).
Audebert MD, "Initial Bordeaux Experience with SprayGel Adhesion Barrier System", Presented at the 10th Congress of the European Society for Gynaecological Endoscopy, Nov. 21-24, 20001, Lisbon, Portugal.
Baines et al., "Adsorption and Removal of Protein Bound to Hydrogel Contact Lenses," Optom Vis Sci 67:807-810 (1990) (abstract).
Bick, "Hemostasis Defects," Seminars in Thrombosis and Hemostasis 11:263-264 (1985).
Bick, "Physiology and Pathophysiology of Hemostasis During Cardiac Surgery" (excerpts), (1995).
Bite et al., "Macrosorb Kieselguhr-Agarose Composite Adsorbents. New Tools for Downstream Process Design and Scale Up. Scientific Note," App/ Biochem Biotechno/ 18:275-284 (1988) (abstract).
Brochure information related to Matrix published by Confluent Surgical, Inc.
Burczak et al., "Protein Permeation Through Poly(Vinyl Alcohol) Hydrogel Membranes," Biomateria/s 15:231-238 (1994) (abstract).
Dunn et al., "Evaluation of a Sprayable Postsurgical Adhesion Barrier in Two Rodent Models", Presented at the Global Congress of Gynecological Endoscopy, 29th Annual Meeting American Association of Gynecological Laparocopists, Nov. 15-19, 2000, Orlando, Florida.
Dunn et al., "Evaluation of the SprayGelTM adhesion barrier in the rat cecum abrasion and rabbit uterine horn adhesion models", Fertility and Sterility, 75(2):411-416, Feb. 2001.
Dunn et al., "Rat (Abdominal) & Rabbit (Pelvic) Studies", Confluent Surgical Inc. Efficacy Preclinical Studies, Summary of the SprayGel Preclinical Animal Models and Studies (2000).
Ferland et al., "Evaluation of a Sprayable, Absorbable Adhesion Barrier in a New Porcine Adhesion Model", Presented at the Global Congress of Gynecological Endoscopy, 29th Annual Meeting American Association of Gynecological Laparocopists, Nov. 15-19, 2000, Orlando, Florida.
Ferland et al., "Evaluation of a sprayable polyethylene glycol adhesion barrier in a porcine efficacy model", Human Reproduction, 16(12): 2718-2723 (2001).
Ferland et al., "Evaluation of SprayGelTM Adhesion Barrier System as a Barrier for the Prevention of Adhesion Formation After Gynecological Surgery", ISGE 10, Chicago, Mar. 2001.
Ferland et al., "Porcine (Pelvic) Efficacy Studies", Confluent Surgical Inc. Efficacy Preclinical Studies, Summary of the SprayGel Preclinical Animal Models and Studies (2000).
Gander et al., "Crosslinked Poly(alkylene Oxides) for the Preparation of Controlled Release Micromatrices", Journal of Controlled Release, (5)271-283 (1988).
Garrett et al., "Human Serum Albumin Adsorption on Hydrogel Contact Lenses In Vitro," Invest aphthalmol Vis Sci 37:2594-2602 (1996) (abstract).
Hill-West et al., "Prevention of Postoperative Adhesions in the Rat by In Situ Photopolymerization of Bioresorbably Hydrogel Barriers," Obstetrics and Gynecology, 83(1): 59 (1994).
Irwin et al., "The Effect of Cyclodextrins on the Stability of Peptides in Nasal Enzymic Systems," Pharmaceutical Research 11:1968-1703 (1994).
Jacobs et al, "SprayGelTM as New Intraperitoneal Adhesion Prevention Method for Use in Laparoscopy and Laparotomy", ISGE 10 Convention, Chicago, Mar. 2001.
Jacobs et al., "A Pressure-Balanced Sprayer for Intraabdominal Application of Soluble Biomaterials in Laparoscopy", ISGE 10 Convention, Chicago, Mar. 2001.
Keogh et al., "Albumin Binding Surfaces for Biomaterials", J. Laboratory & Clinical Med. 124.4:537-545 (1994).
Kissell et al., "Parenteral depot-systems on the basis of biodegradable polyesters," Journal of Controlled Release 16:27-42 (1991).
Kolthammer, "The In Vitro Adsorption of Drugs from Horse Serum onto Carbon Coated with an Acrylic Hydrogel," J Pharm Pharmaco/ 27:801-805 (1975) (abstract).
Kulik et al., "In Vitro Platelet Adhesion to Nonionic and Ionic Hydrogels with Different Water Contents," J Biomed Mater Res 30:295-304 (1996) (abstract).
Lazarus et al., "Selective In Vivo Removal of Rheumatoid Factor by an Extracorporeal Treatment Device in Rheumatoid Arthritis Patients," Transfusion 31:122-128 (1991) (abstract).
Lin et al., "The Influence of Adsorption of Native and Modified Antibodies on Their Activity," J Immunol Methods 125:67-77 (1989) (abstract).
Mathiowitz et al., "Polyanhydride Microspheres As Drug Carriers I. Hot-Melt Microencapsulation", J Controlled Release 5:13-22 (1987).
Mettler et al., "Prospective Clinical Trial of SprayGel as a Barrier to Adhesion Formation: Interim Analysis", The Journal of the American Association of Gynecologic Laparocopists, 10(3):339-344 (2003).
Mettler MD et al., A Randomised Prospective Multi-Centre Clinical Trial of Spraygel as a Barrier for Prevention of Adhesion Formation after Gynaecological Surgery: An Intermin Analysis, Presented at the 10th Congress of the European Society for Gynaecological Endoscopy, Nov. 21-24, 20001. Lisbon Portugal.
Nasaduke et al., "The Use of Autogenous Rabbit Fibrin Sealant to Plug Retinal Holes in Experimental Detachments" Annals of Ophthalmology, 18:324-327 (1986).
Nihant et al., "Polylactide Microparticles Prepared by Double Emulsion-Evaporation", J. Colloid & Interface Science 173:55-65 (1995).
Pathak et al., "Rapid Photopolymerization of Immunoprotective gels in Contact with Cells and Tissue," J. Am. Chem. Soc. 114(21):8311-8312 (1992).
Quinn et al., "Biocompatible, glucose-permeablehydrogel for in situ coating of implantable biosensors", Biomaterials, 18(24):1665-1670 (1997).
Reddy et al., "Polyurethane Microspheres as Drug Carriers", Macromolecular Reports A32:789-799 (1995).
Saraydin et al., "Adsorption of Bovine Serum Albumin onto Acrylamide-Maleic Acid Hydrogels," Biomaterials 15:917-920 (1994) (abstract).
Sawhney et al., "Bioerodible Hydrogels Based on Photopholmerized Poly(ethylene glycol)-co-poly(α-hydroxy acid) Diacrylate Macromers", Macromolecules 26:581-587 (1993).
Sawhney et al. "Rabbit (Pericardial) Adhesion Study", Confluent Surgical Inc. Efficacy Preclinical Studies, Summary of the SprayGel Preclinical Animal Models and Studies (2000).
Schlag et al., "Fribin Sealant in Orthopedic Surgery" Fibrin Sealant in Operative Orthopedic Surgery, vol. 1-7:269-284 (1986).
US 6,214,374, 04/2001, Schmirler et al. (withdrawn)

* cited by examiner

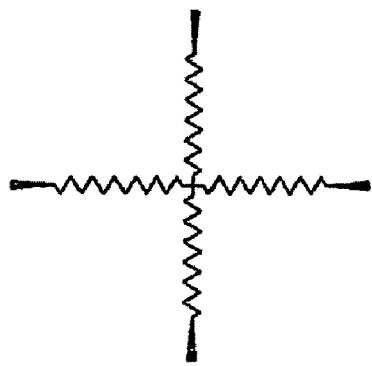
FIG. 3M
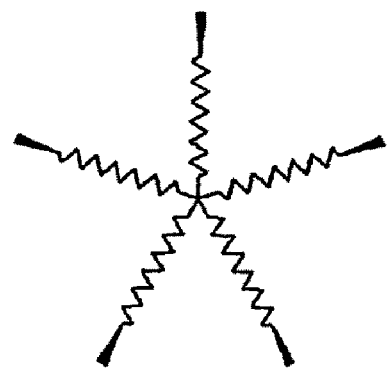
FIG. 3O
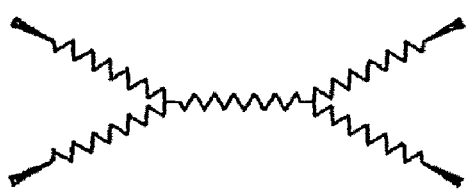
FIG. 3N
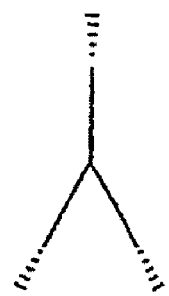
FIG. 4Q
FIG. 4P
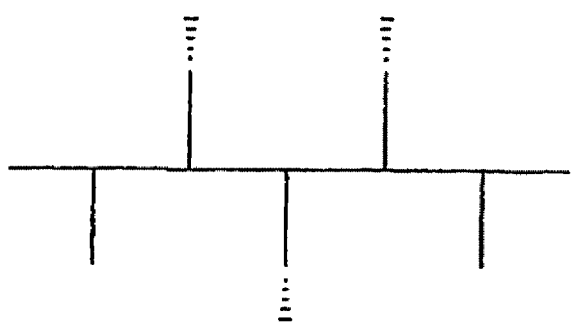
FIG. 4T Spermidine MW 145 Dalton Spermine MW 202 Dalton Ornithine MW 168 Daltons Dilysine MW ~347 Daltons

BIOCOMPATIBLE HYDROGELS MADE WITH SMALL MOLECULE PRECURSORS

RELATED APPLICATIONS

The present patent application is a continuation in part of U.S. Ser. No. 12/069,821 filed Feb. 13, 2008, now U.S. Pat. No. 7,592,418 which is a continuation of U.S. Ser. No. 11/293,892 filed Dec. 2, 2005 issued as U.S. Pat. No. 7,332,566, which is a continuation of U.S. Ser. No. 10/010,715 filed Nov. 9, 2001 issued as U.S. Pat. No. 7,009,034, which is a continuation-in-part of U.S. Ser. No. 09/454,900 filed Dec. 3, 1999 issued as U.S. Pat. No. 6,566,406 that claims priority to U.S. Ser. No. 60/110,849 filed Dec. 4, 1998; U.S. Pat. No. 7,009,034 is also a continuation-in-part of U.S. Ser. No. 09/147,897 filed Aug. 30, 1999, now abandoned which has priority to application No. PCT/US97/16897 filed Sep. 22, 1997 which has priority to U.S. Ser. No. 60/040,417 filed Mar. 13, 1997, U.S. Ser. No. 60/039,904 filed Mar. 4, 1997, and U.S. Ser. No. 60/026,526 filed Sep. 23, 1996. Each of these patent applications are claimed as priority documents and are hereby incorporated by reference herein.

FIELD OF THE INVENTION

The field of the invention relates generally to biocompatible crosslinked polymers, and methods for preparing and using the same.

BACKGROUND

Almost every surgical treatment carries a risk that bodily tissues exposed during the course of the surgery will adhere to each other, a condition termed an adhesion. Gynecological and abdominal surgeries, in particular, are prone to causing adhesions, which often have the appearance of scar-like masses. Adhesions are frequently painful and are a significant cause of infertility resulting from gynecological surgeries. Adhesions caused by surgeries are often called surgical adhesions.

One approach to the treatment of adhesions has been to coat surgically exposed tissues with a gel before closing the surgical site. Gels of various types have been used, including suspensions of colloidal particles, and pastes of natural polymers.

Hydrogels are especially useful for use in the body because they are more biocompatible than non-hydrogels and are thus better tolerated in the body.

SUMMARY

Some embodiments are hydrogels having controlled degradability and swelling properties. The reaction of at least two precursors forms the hydrogel, which may have an isolated ester molecular functional group. The isolated ester group spontaneously degrades in the patient's body as a result of being in contact with water, a process known as hydrolysis.

Some embodiments are methods for making a readily degradable hydrogel by providing at least a first biocompatible precursor having at least two electrophilic functional groups, providing at least a second biocompatible precursor comprising at least two primary amine functional groups; optionally providing at least a third biocompatible precursor comprising at least two primary amine functional groups; wherein the first precursor, the second precursor, and the third precursor are reactable with each other to form a crosslinked hydrogel, are resistant to enzymatic degradation, and at least one of the first, second, or third precursors includes at least one isolated hydrolytically degradable ester group. And mixing at least the first precursor, the second precursor, and optionally the third precursor to form a crosslinked hydrogel in situ including covalent bonds formed by reaction of the functional groups of the precursors and further including the at least one isolated hydrolytically degradable ester group; and, providing a sufficient number of the at least one isolated hydrolytically degradable ester groups in the crosslinked hydrogel so that the crosslinked hydrogel is readily degradable in less than about 180, 90, or 45 days. The crosslinked hydrogel may be resistant to enzymatic degradation and may be degradable by hydrolysis of the at least one isolated hydrolytically degradable ester group.

Embodiments can include a kit having a first biocompatible precursor with at least two electrophilic functional groups, and a second biocompatible precursor comprising at least two primary amine functional groups, an optional third biocompatible precursor including at least two primary amine functional groups and, and an applicator. In some embodiments, the first precursor, the second precursor, and the third precursor are reactable with each other to form a crosslinked hydrogel, are resistant to enzymatic degradation, and at least one of the first, second, or third precursors includes at least one isolated hydrolytically degradable ester group. The applicator can be configured to mix at least the first precursor, the second precursor, and the third precursor to form a crosslinked hydrogel in situ comprising covalent bonds formed by reaction of the functional groups of the precursors and further including the at least one isolated hydrolytically degradable ester group; wherein the hydrogel includes a sufficient number of the at least one isolated hydrolytically degradable ester groups in the crosslinked hydrogel so that the crosslinked hydrogel is readily degradable in less than about 180 days, is resistant to enzymatic degradation, and is degradable by hydrolysis of the at least one isolated hydrolytically degradable ester group. A kit can have instructions that include directions for making a hydrogel that is degradable in an amount of time, with the amount of time being less than about 180, 90, or 45 days.

The instructions of a kit may be written, e.g., electronic or paper format, including electronic publication, e.g., by posting on the world wide web. Examples of instructions include a label referring to a web site, directions on packaging, directions on a label, a written insert in a package. Materials provided independently of the kit that provide directions to the user are also instructions, e.g., seminar materials, training materials, videotapes, audiotapes, internet-based seminars, and explanatory brochures.

Some embodiments are hydrogels made from electrophiles and low molecular weight amines, e.g., wherein the second precursor and the third precursor may be dilysine, trilysine, tetralysine, and Tris. Other embodiments, e.g., kits, systems, methods, and hydrogels, include a low molecular weight amine such as ornithine, spermine, spermidine, urea, guanidine, diaminopimelic acid, diaminobutyric acid, methylornithine, diaminopropionic acid, cystine, lanthionine, cystamine, trioxamidecanediamine, cyclohexanebis(methylamine), tetraethylenepentamine, pentaethylenehexamine, methylenebis(methylcyclohexamine), diaminocyclohexane, n-(2-aminoethyl)-1,3-propanediamine, diaminomethyldipropylamine, iminobispropylamine, bis(hexamethlyene)triamine, triethylenetetramine, bis(aminopropyl)ethylenediamine, bis(2-aminoethyl)-1,3-propanediamine, bis(aminopropyl)propanediamine, diaminomethylpropane, 1,2-diamino-2-methylpropane, 1,3-diaminopentane, dimethylpropanediamine, 2,2-dimethyl 1,3-propanediamine, methylpentanediaminea, 2-methyl-1,5 pentanediamine, diaminoheptane, diaminooctane, diaminononane, diaminodecane, and diaminododecane.

Some embodiments are methods for making a readily degradable hydrogel by providing at least a first biocompatible precursor having at least two electrophilic functional groups and providing at least a second biocompatible precursor including at least two primary amine functional groups. In some embodiments, the first precursor and the second precursor are reactable with each other to form a crosslinked hydrogel, are resistant to enzymatic degradation, and at least one of the first or second precursors include at least one isolated hydrolytically degradable ester group. Some embodiments entail steps of mixing at least the first precursor and the second precursor to form a crosslinked hydrogel comprising covalent bonds formed by reaction of the functional groups of the precursors and further including the at least one isolated hydrolytically degradable ester group; and providing a sufficient number of the at least one isolated hydrolytically degradable ester groups in the crosslinked hydrogel so that the crosslinked hydrogel is readily degradable in less than about 180, 90, 45, or fewer, days; wherein the crosslinked hydrogel is resistant to enzymatic degradation, and is degradable by hydrolysis of the at least one isolated hydrolytically degradable ester group, and wherein the second precursor is a low molecular weight amine.

Some embodiments are a method for making a medical device chosen from a group consisting of an adhesion prevention barrier, a tissue glue, a drug delivery matrix, a wound dressing, a tissue engineering matrix, an implant and a tissue coating. Medical devices may be made by providing at least a first biocompatible precursor having least two electrophilic functional groups, and providing at least a second biocompatible precursor comprising at least two primary amine functional groups and mixing at least the first precursor and the second precursor in situ to form the device. Some embodiments of the device include a crosslinked hydrogel including covalent bonds formed by reaction of the functional groups of the precursors and further include the at least one isolated hydrolytically degradable ester group; wherein the crosslinked hydrogel is resistant to enzymatic degradation, is readily degradable by hydrolysis of the at least one isolated hydrolytically degradable ester group, and includes a sufficient number of the isolated hydrolytically degradable ester groups in the crosslinked hydrogel so that the device is readily degradable in less than about 180 days. Some embodiments provide a first precursor and a second precursor that are resistant to enzymatic degradation and have at least one isolated hydrolytically degradable ester group.

Some embodiments are readily degradable materials that have a crosslinked biocompatible hydrogel that includes products of a reaction between a first biocompatible precursor, a second biocompatible precursor, and a third biocompatible precursor, with at least one of the precursors including an isolated hydrolytically degradable ester group, wherein the crosslinked hydrogel is resistant to enzymatic degradation and is degradable by hydrolysis of the isolated hydrolytically degradable ester groups. The second biocompatible precursor can be, before reaction, dilysine, trilysine, and tetralysine. The third biocompatible precursor, before reaction, can be a low molecular weight amine, e.g., Tris, ornithine, spermine, spermidine, urea, guanidine, diamniopimelic acid, diaminobutyric acid, methylornithine, diaminopropionic acid, cystine, lanthionine, cystamine, trioxamidecanediamine, cyclohexanebis(methylamine), tetraethylenepentamine, pentaethylenehexamine, methylenebis(methylcyclohexamine), diaminocyclohexane, n-(2-aminoethyl)-1,3-propanediamine, diaminomethyldipropylamine, iminobispropylamine, bis(hexamethlyene)triamine, triethylenetetramine, bis(aminopropyl)ethylenediamine, bis(2-aminoethyl)-1,3-propanediamine, bis(aminopropyl)propanediamine, diaminomethylpropane, 1,2-diamino-2-methylpropane, 1,3-diaminopentane, dimethylpropanediamine, 2,2-dimethyl 1,3-propanediamine, methylpentanediamine, 2-methyl-1,5 pentanediamine, diaminoheptane, diaminooctane, diaminononane, diaminodecane, and diaminododecane.

Some embodiments are methods for using the polymeric compositions to coat a tissue by mixing hydrophilic precursor polymers with chemically distinct reactive functional groups such that they form crosslinks via nucleophilic-electrophilic reaction after mixing and contact with the tissue. The polymers crosslink to form a biodegradable hydrogel. A preferred application is to prevent surgical adhesions by applying the hydrogel as a coating on a tissue substrate and maintaining another surface of the hydrogel as a free surface. A visualization agent may be included so that the visualization agent is disposed within the hydrogel and reflects or emits light at a wavelength detectable to a human eye.

DETAILED DESCRIPTION

Figure 1A:
FIG. 1 depicts electrophilic functional group water soluble and biodegradable crosslinkers or functional polymers, which can be crosslinked with appropriate nucleophilic functional group precursors.
Figure 1B:
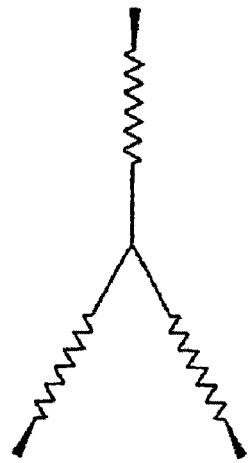
Figure 1C:
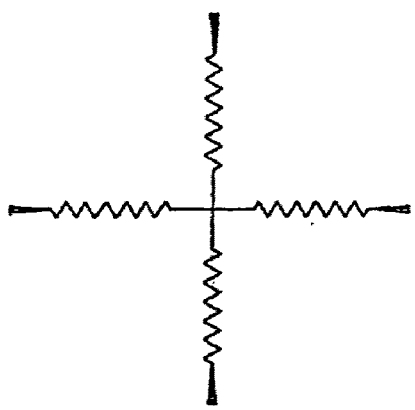
Figure 1E:
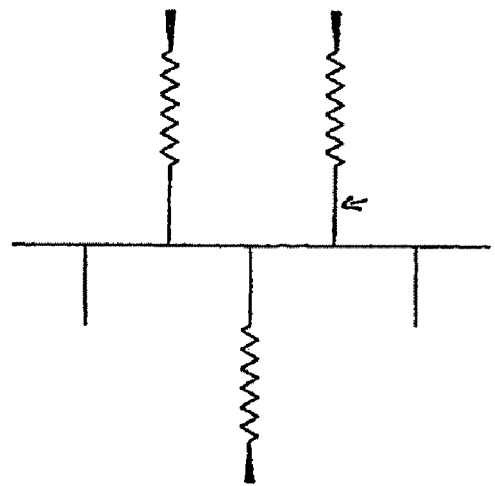
Figure 1D:
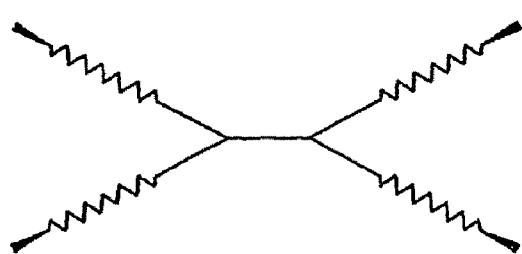
Figure 2F:
FIG. 2 depicts nucleophilic water soluble and biodegradable crosslinkers or functional polymers, which can be crosslinked with appropriate electrophilic precursors.
Figure 2G:
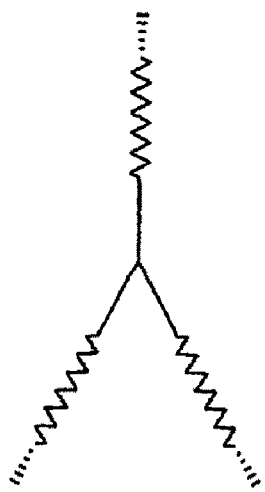
Figure 2H:
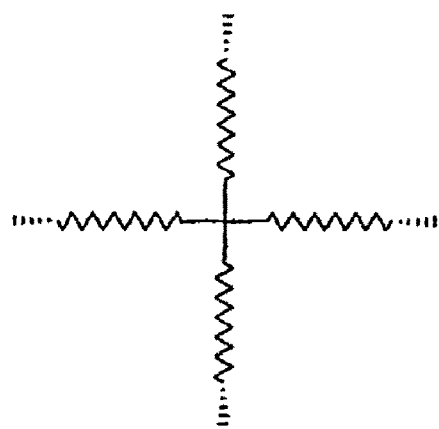
Figure 2J:
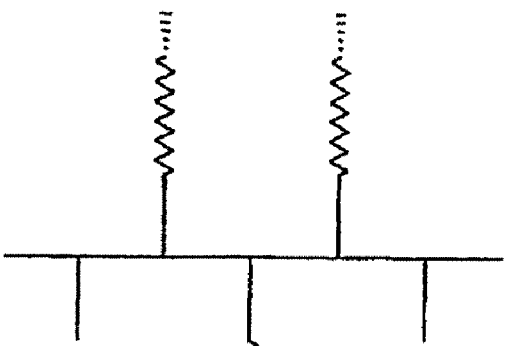
Figure 2I:
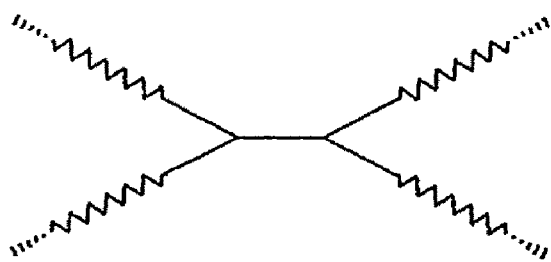

The degradation rate of a hydrogel implant in a patient is an important aspect of the hydrogel. It is desirable for many applications to make a hydrogel that is readily degradable. Further, it is desirable for many applications that the hydrogel be formulated so that its degradability is predictable. Set forth herein are certain embodiments directed to readily degradable hydrogels that have a predictable degradation profile. Set forth are certain embodiments made from precursors having isolated esters and low molecular weight amines that provide unexpected results of ready degradation and predictable degradation profiles.

Previously, biodegradable implants were typically made of polylactides and/or polyglycolides, or other polymers having contiguous esters. The esters degrade in water, a process termed hydrolysis. Polyglycolides are, in general, absorbed by a patient's body in the space of a few months, whereas polylactides require longer times. Polylactides include Poly-L-lactide, which is generally crystalline in structure, and Poly-DL-lactide, which is generally amorphous. The crystalline structure resorbs more slowly because it is hydrated more slowly. Since these polymers, generally speaking, degrade in a few months' time span, it is difficult to make readily degradable implants using these materials.

One would normally predict that a polyester would degrade more rapidly than an isolated ester because average time for hydrolysis of the first ester in a group of esters should be shorter than the time required for just one ester. In other words, if an ester were to typically require one to three days to hydrolyze in water, then it is more likely that one out of ten esters would hydrolyze before one out of one esters would hydrolyze. Therefore, it would normally be expected that a polymer having multiple adjacent esters would degrade more rapidly than polymers having the same number of isolated esters, or a polymer having fewer isolated esters. It is unexpected, therefore, that hydrogels made using isolated esters would readily degrade under circumstances where hydrogels made of multiple adjacent esters do not readily degrade.

Certain embodiments set forth herein, however, include hydrogels made from combinations of polymers having isolated esters plus low molecular weight amines that degrade readily. An isolated ester is an ester that is not adjacent to another ester. A low molecular weight amine is a molecule having at least two primary amine groups and a molecular weight of less than 1000. Without being bound to any particular theory, it is believed that unreacted primary amines present in the hydrogel enhance the basicity of water in the region next to the isolated esters so that their hydrolysis is accelerated. Further, or alternatively, tension in the polymers created by the short length of the low molecular weight amine may serve to accelerate degradation.

It has not been previously appreciated in the relevant arts that isolated esters are readily degradable. As a result, methods of making hydrogels that degrade by the action of isolated esters have not been previously appreciated, and readily degradable devices or products for use in the body have not been made using isolated esters. Readily degradable means being approximately completely degraded after less than approximately six months, as indicated by an essentially complete loss of mechanical strength. Further, the use of low molecular weight amines in certain compositions and methods has yielded unexpected results that have not been previously expected or appreciated. Various examples of the use of gels or hydrogels in the body, or for various other uses, are described in, for example, U.S. Pat. Nos. 6,020,326, 5,874,500, 5,814,621, 5,605,938, 5,527,856, 5,550,188, 4,414,976, 4,427,651, and 4,925,677; each of which are hereby incorporated by reference to the extent they do not contradict what is explicitly disclosed herein.

Figure 46:
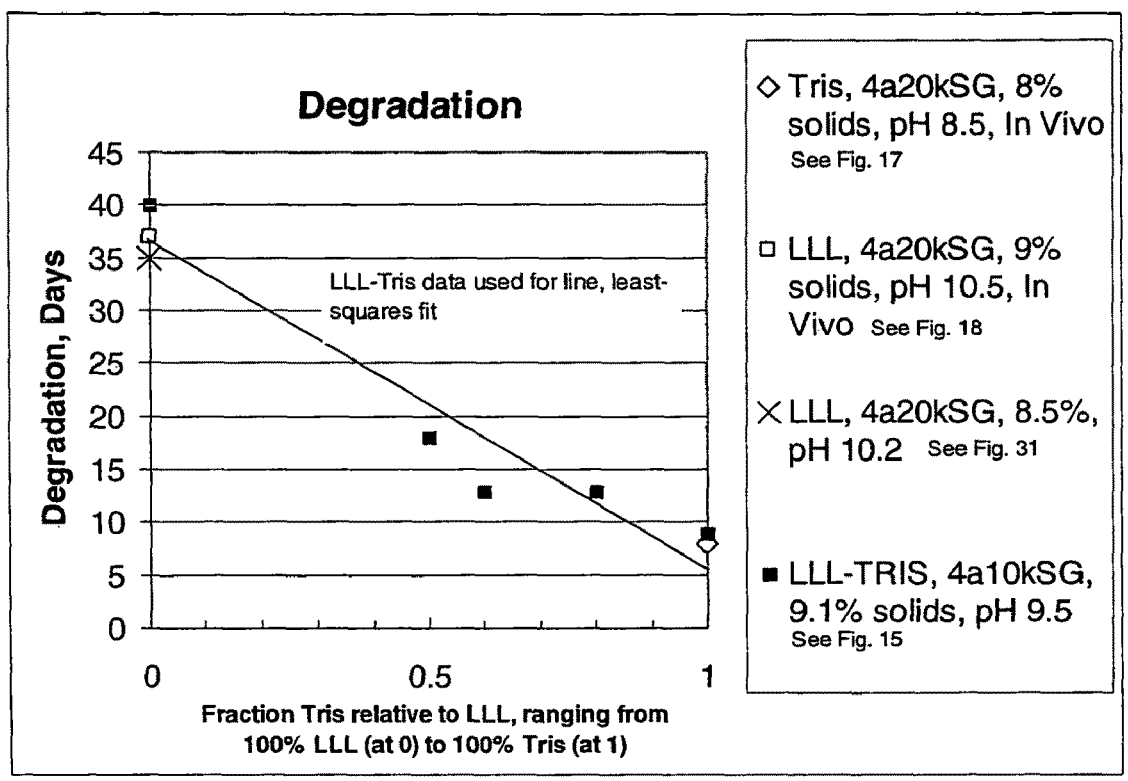
FIG. 46 is a graph showing the degradability of hydrogels made from multiarmed electrophiles mixed with low molecular weight amines.

One aspect of the use of combinations of low molecular weight amines is that they unexpectedly have an approximately linear degradation profile. Referring to FIG. 46, the degradation time for hydrogels made of mixtures of low molecular weight amines, Tris and trilysine, is approximately linearly dependent upon the relative amounts of the low molecular weight amines. A predictable degradation rate is useful for designing devices and materials that require degradation within a certain time window. This result is unexpected because it is not exhibited by polymers having multiple adjacent esters. For example, a crosslinked material of lactide and glycolide polymers (both having multiple adjacent esters) does not degrade in a time that directly correlates to the ratio of the materials.

The Applicants have appreciated the aspect of isolated esters being useful for making readily degradable materials. Multiple low molecular weight amines have been tested and determined to be suitable to make readily degradable hydrogels. An in vitro gel time disappearance test may be used to approximate in vivo degradability, as described in Example 13, which sets forth procedures that a person of ordinary skill in these arts may use to determine degradation. Embodiments of readily degradable gels that degrade in less than six months are also contemplated, including gel degradation times of one day or six months and every amount of time in between one day and six months.

Figure 13:
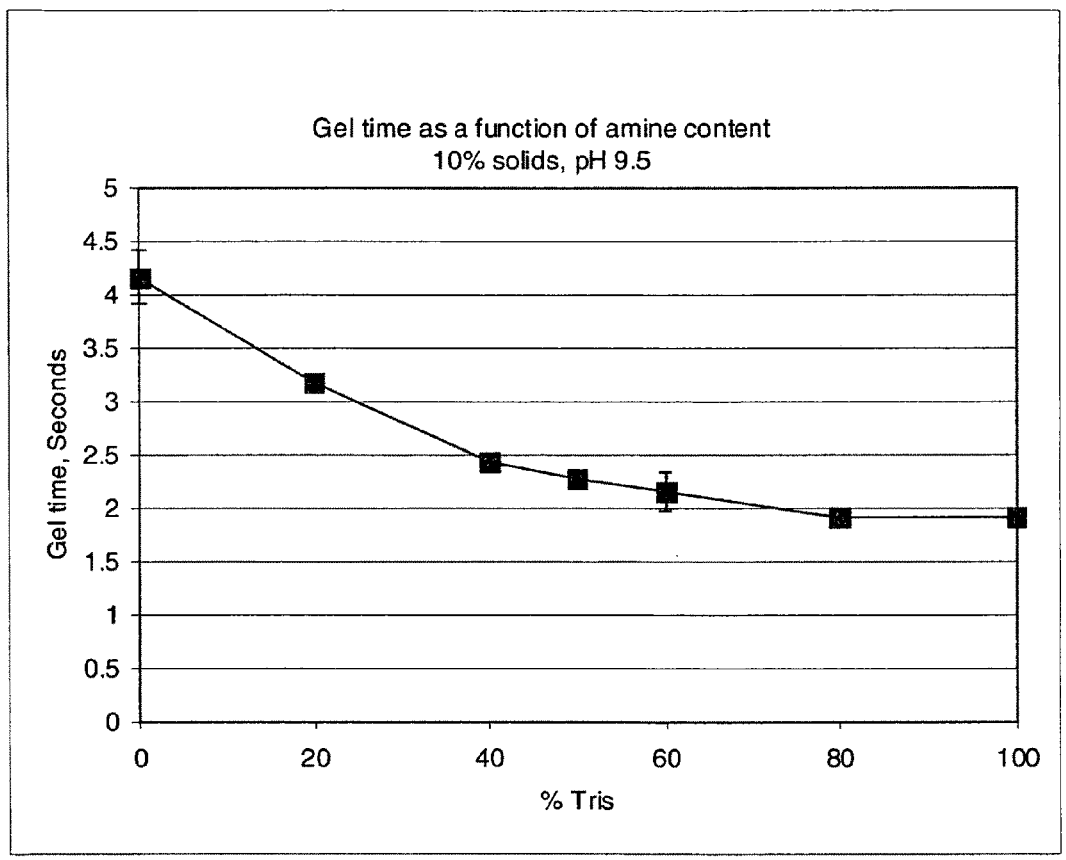
FIG. 13 is a graph of an example of a gel time of a hydrogel as a function of Tris content in an LLL-Tris hydrogel, as is further described in Example 13.
Figure 14:
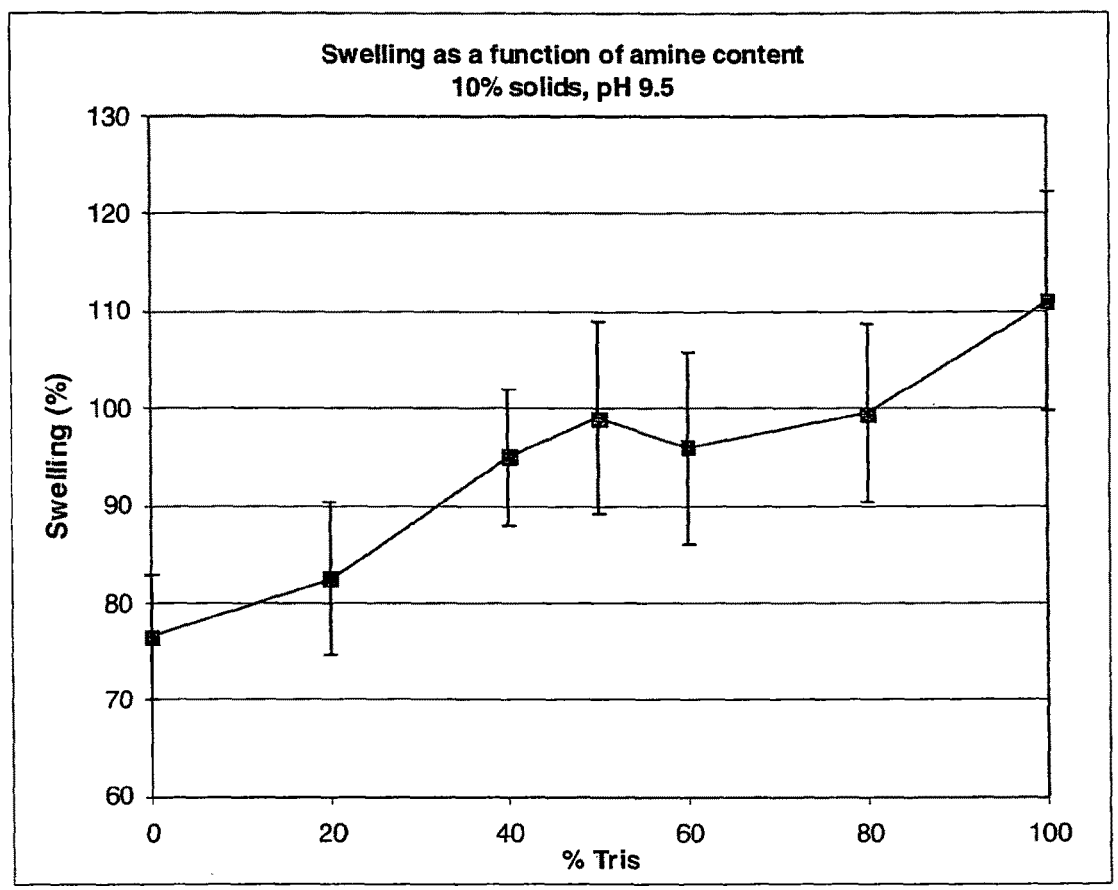
FIG. 14 is a graph of swelling of a hydrogel as a function of Tris content in an LLL-Tris hydrogel, as is further described in Example 13.
Figure 15:
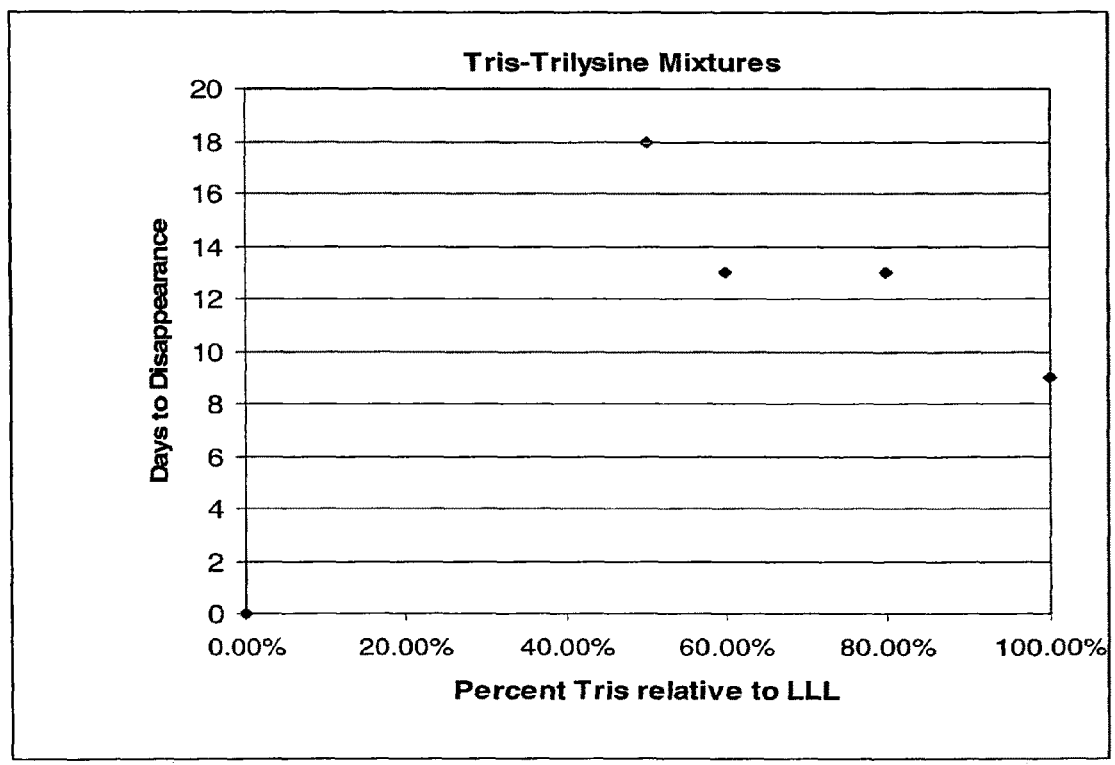
FIG. 15 is a graph of degradation of a hydrogel as a function of Tris content in an LLL-Tris hydrogel, as is further described in Example 13.
Figure 16:
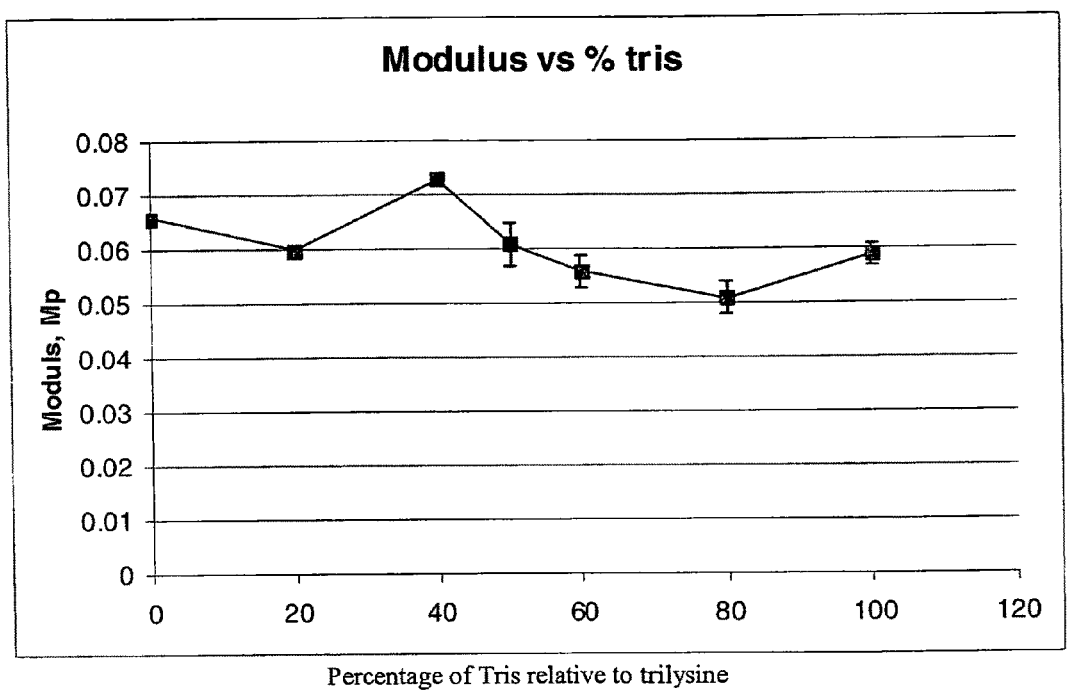
FIG. 16 is a graph of a modulus of a hydrogel as a function of Tris content in an LLL-Tris hydrogel, as is further described in Example 13.

The combination of at least two low molecular weight amines with a polymer having at least one isolated ester to make a hydrogel having isolated esters was found to be particularly effective in making a degradable gel. For instance, Example 13 shows that the combination of Tris and trilysine had unexpectedly accelerated gelation, and degradation rates compared to formulations of only trilysine (FIGS. 13-15).

Figure 21:
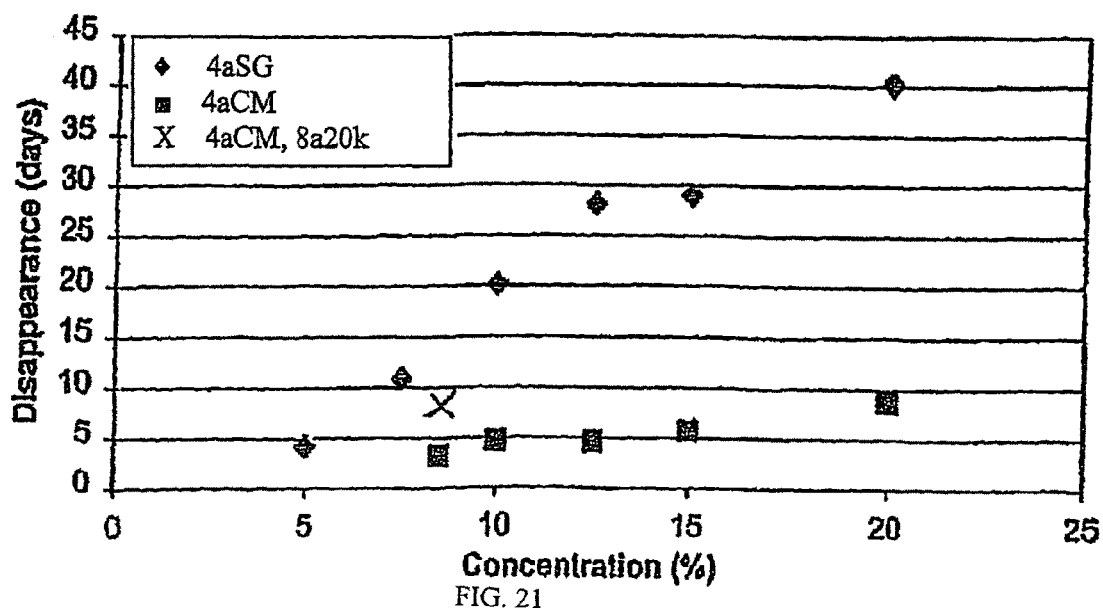
FIG. 21 depicts the degradation of hydrogels formed with dilysine (LL or Lys-Lys), see also Example 16.
Figure 22:
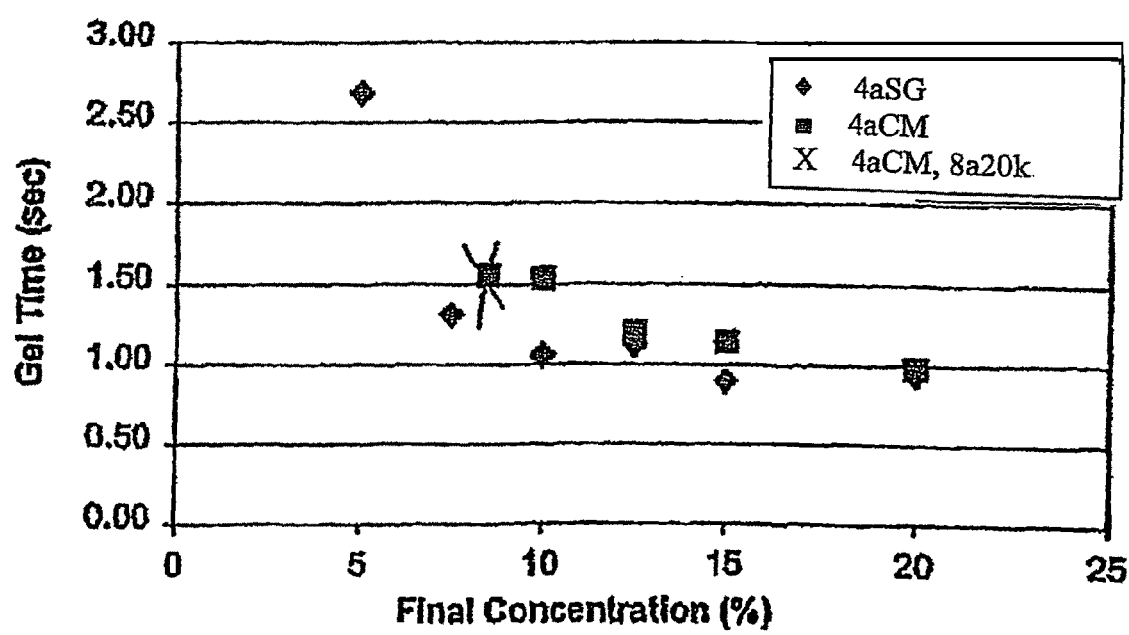
FIG. 22 depicts the gel time of hydrogels formed with dilysine (LL or Lys-Lys) as a function of solids concentration, see also Example 16.
Figure 23:
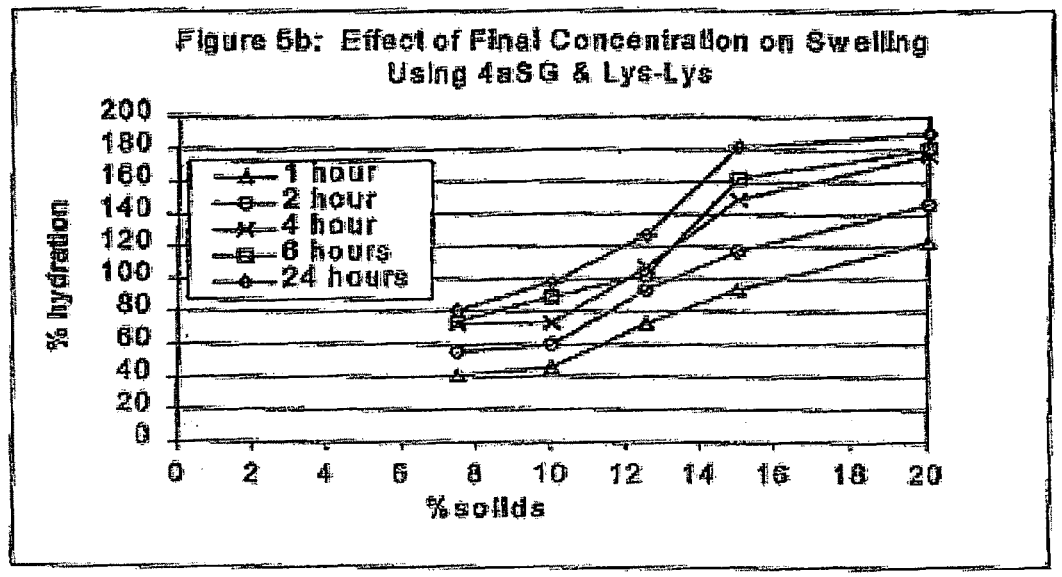
FIG. 23 depicts the swelling of hydrogels formed with dilysine (LL or Lys-Lys) as a function of solids concentration, see also Example 16.

Detailed methods and procedures for using low molecular weight amines in conjunction with isolated ester precursors are set forth herein. For example, FIGS. 17 and 18 (Examples 14 and 15) show the persistence of isolated ester hydrogels made using the low molecular weight amine trilysine or the combination Tris-trilysine in vivo. The properties of isolated ester hydrogels made using dilysine were also examined, as shown in FIGS. 21-23 (Example 16). Multiple low molecular weight amines were used in Examples 17 and 18 to make hydrogels that contained isolated esters (FIGS. 11, 12, 25-39). Aspects relating to the solids content, pH, pot life, swelling, degradation, gel time, and modulus are set forth in the Examples. Example 19 provides a detailed example of maintaining hydrogels having a predictable degradability using combinations of low molecular weight amines in conjunction with isolated esters (FIGS. 42-45). Examples 20 and 21 set forth a detailed study involving the low molecular weight amine dilysine in conjunction with various electrophiles having isolated esters.

A coating has a surface that can be viewed for use with a visually observable visualization agent. In contrast, a hydrogel injected into a blood vessel, muscle, or other tissue has essentially no surface for viewing a visualization agent because its surface area is essentially engaged with tissues of the patient. Further, polymers injected into a tissue lack a surface that is disposed on the surface of a tissue and do not provide a means for a user to control the thickness of the coating on the surface of the tissue. Hydrogels that are merely injected into a patient's body would not be equivalent to embodiments that involve a hydrogel coating on a substrate and are inoperative for embodiments that entail use of a visualization agent in a hydrogel coating.

An embodiment involves a mixture or a process of mixing hydrophilic reactive precursor species having nucleophilic functional groups with hydrophilic reactive precursor species having electrophilic functional groups such that they form a mixture that crosslinks quickly after contact with the tissue of a patient to form a biodegradable hydrogel that coats and adheres to a tissue. This may be achieved by making reactive precursor species that crosslink quickly after mixing. Hydrophilic reactive precursor species can be dissolved in buffered water such that they provide low viscosity solutions that readily mix and flow when contacting the tissue. As they flow across the tissue, they conform to the shape of the small features of the tissue such as bumps, crevices and any deviation from molecular smoothness. If the reactive precursor species are too slow to crosslink, they will flow off the tissue and away into other portions of the body with the result that the user will be unable to localize the hydrogel on the desired tissue. Without limiting the invention to a particular theory of operation, it is believed that reactive precursor species that crosslink appropriately quickly after contacting a tissue surface will form a three dimensional structure that is mechanically interlocked with the coated tissue. This interlocking contributes to adherence, intimate contact, and essentially continuous coverage of the coated region of the tissue.

Adherence is important for medical applications that require a coating, e.g., for prevention of adhesions, since a user must be able to place the hydrogel in the portions of the patient that are needful, for example, around an ovary or surrounding an intestine. Further, the hydrogel must remain on the intended tissue or it will be unable to provide a prophylactic barrier. The hydrogels have good adhesion onto tissue and are useful for all applications wherein surgical glues have previously been used. For example, sealing of the dura mater of the brain to prevent leakage of cerebrospinal fluid may be accomplished with combinations of reactive precursor species described herein by using reactive precursor species with nucleophilic functional groups for mixing with hydrophilic reactive precursor species having electrophilic functional groups to form a mix that crosslinks quickly after contact with the tissue of a patient, e.g., the dura mater, to form a hydrogel that coats a tissue.

A simple dip test that shows that a hydrogel has adherence. To perform this test, a gel of about 5×5 centimeters in length× width and about 4 to 10 mm in thickness is formed on a substrate, the hydrogel is immersed in water or physiological saline for five minutes, removed, and tilted to an angle of 90 degrees above horizontal, and dipped into and out of a vessel of physiological saline five times at a rate of about 10 mm per second so that the hydrogel passes through the air-water interface ten times. Then the substrate is rotated about 90 degrees so that the substrate is approximately horizontal and the hydrogel is below the substrate. The substrate is left in this position for five minutes. The gel passes the dip test if less than about 1 square centimeter of the gel is then observed to be separated from the substrate. If the substrate lacks stiffness, it may be affixed to a stiff support so that it may tested. Physiological saline, in the context of the dip test, means a saline solution with an approximately physiological osmolarity and a pH of 7.0-7.4 at room temperature that is customarily used in cell culture, for example, phosphate buffered saline. As used herein, the gel has adherence to a substrate if it passes the dip test.

Suitable crosslinking times vary for different applications. In most applications, the crosslinking reaction leading to gelation occurs within about 10 minutes, more preferably within about 2 minutes, even more preferably within 10 seconds. In the case of most surgical adhesion prevention applications, it is preferable to use a hydrogel that crosslinks in less than about 10 seconds and more preferably in about 2-4 seconds in order to allow a user to make multiple passes with a hydrogel applicator tool such as a sprayer; see, for example commonly assigned U.S. Pat. Nos. 6,179,862; 6,165,201; 6,152,943; and 6,610,033, which are hereby incorporated herein by reference to the extent they do not contradict what is explicitly disclosed. In the case of tissues that can be accessed only indirectly, longer times are most preferable to allow the gel a longer time to flow into the inaccessible space. For example, application of an adhesion barrier in and around the spinal cord and exiting nerve roots following spine surgery may require several extra seconds to penetrate around the complex geometry of the tissues so that a preferred time is between about 5 and about 90 seconds and more preferably between about 10 and about 30 seconds. The Examples herein describe a variety of reactive precursor species and methods of making reactive precursor species that may be mixed to provide crosslinked networks that crosslink quickly after mixing such that one skilled in these arts will understand how to make the required materials after reading this disclosure.

Functional Groups

Each precursor is multifunctional, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products. Such reactions are referred to as "crosslinking reactions".

Preferably, each precursor comprises only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly(allyl amine), or amine-terminated di- or multifunctional poly(ethylene glycol) ("PEG") can be used.

Low Molecular Weight Amine Precursors and Hydrogels

Some embodiments are directed to the use of low molecular weight amines having at least two primary amines and a molecular weight of less than about 1000. Examples of such low molecular weight amines are dilysine, trilysine, tetralysine, and Tris. Following the nomenclature set forth in the Aldrich Catalog of 2002, other such examples are ornithine, spermine, spermidine, urea, guanidine, diamniopimelic acid, diaminobutyric acid, methylornithine, diaminopropionic acid, cystine, lanthionine, cystamine, trioxamidecanediamine, cyclohexanebis(methylamine), tetraethylenepentamine, pentaethylenehexamine, methylenebis(methylcyclohexamine), diaminocyclohexane, n-(2-aminoethyl)-1,3-propanediamine, diaminomethyldipropylamine, iminobispropylamine, bis(hexamethlyene)triamine, triethylenetetramine, bis(aminopropyl)ethylenediamine, bis(2-aminoethyl)-1,3-propanediamine, bis(aminopropyl)propanediamine, diaminomethylpropane, 1,2-diamino-2-methylpropane, 1,3-diaminopentane, dimethylpropanediamine, 2,2-dimethyl 1,3-propanediamine, methylpentanediamine, 2-methyl-1,5 pentanediamine, diaminoheptane, diaminooctane, diaminononane, diaminodecane, and diaminododecane.

Low molecular weight amines may be used to make hydrogels by combining them with suitable electrophiles such as those set forth herein. A low molecular weight amine having only two primary amines would normally require combination with an electrophile having at least three arms in order to achieve a cross-linked hydrogel. The low molecular weight amines may be used in combination with other nucleophiles set forth herein, including multiarmed polyethylene glycols. For example, Tris may be combined with dilysine, trilysine, tetralysine, or other low molecular weight amines. Combinations of at least one low molecular weight amine are contemplated, including combinations of two, three, four, or more. Combinations of low molecular weight amines with proteins, degradable polymers, and other materials as set forth herein are also contemplated.

Multiple working examples are presented herein that describe how to make and use materials created from low molecular weight amines, including various considerations involving solids content, pH, and stoichiometry. For instance, Examples 2-4 describe use of di-, tri-, and tetra-lysine, and Example 17 describes the use of ornithine, spermidine, and spermine. Some embodiments entail use of low molecular weights amines with isolated esters to make hydrogels having isolated esters.

Water Soluble Cores

The precursors preferably have biologically inert and water soluble cores. When the core is a polymeric region that is water soluble, preferred polymers that may be used include: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly (vinyl pyrrolidinone) ("PVP"); poly (amino acids); dextran and proteins such as albumin. The polyethers and more particularly poly(oxyalkylenes) or poly (ethylene glycol) or polyethylene glycol are especially preferred. When the core is small molecular in nature, any of a variety of hydrophilic functionalities can be used to make the precursor water soluble. For example, functional groups like hydroxyl, amine, sulfonate and carboxylate, which are water soluble, maybe used to make the precursor water soluble. In addition, N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

Biodegradable Linkages

If it is desired that the biocompatible crosslinked polymer be biodegradable or absorbable, one or more precursors having biodegradable linkages present in between the functional groups may be used. The biodegradable linkage optionally also may serve as the water soluble core of one or more of the precursors. In the alternative, or in addition, the functional groups of the precursors may be chosen such that the product of the reaction between them results in a biodegradable linkage. For each approach, biodegradable linkages may be chosen such that the resulting biodegradable biocompatible crosslinked polymer will degrade or be absorbed in a desired period of time. Preferably, biodegradable linkages are selected that degrade under physiological conditions into non-toxic products.

The biodegradable linkage may be chemically or enzymatically hydrolyzable or absorbable. Illustrative chemically hydrolyzable biodegradable linkages include polymers, copolymers and oligomers of glycolide, dl-lactide, l-lactide, caprolactone, dioxanone, and trimethylene carbonate. Another chemically hydrolyzable biodegradable linkage is an isolated ester group. An isolated ester group is an ester group that is not adjacent to another ester group. In contrast, polymers and oligomers of, for example, glycolides and lactides, have ester groups that are adjacent to each other. The results set forth herein indicate that the behavior of an isolated ester group is often distinct from that of non-isolated esters in the context of hydrolysis. Additional illustrative biodegradable linkages include polymers and copolymers of poly(hydroxy acid)s, poly(orthocarbonate)s, poly(anhydride)s, poly(lactone)s, poly(aminoacid)s, poly(carbonate)s, and poly(phosphonate)s.

Illustrative enzymatically biodegradable linkages include peptidic linkages cleavable by proteases, metalloproteinases and collagenases. A hydrogel that is resistant to enzymatic degradation does not contain linkages that are preferentially cleaved by enzymes, including metalloproteinases and collagenases. Preferential cleavage of a polymer by enzymes means that an enzyme has a preference for a particular chemical group in a polymer as compared to most other chemical groups. In contrast, some enzymes secrete chemicals that exhibit little specificity, for example, enzymes that secrete radicals that degrade the materials that they contact. Further, proteins may generally be considered to be enzymatically cleavable since most proteins have specific sequences that are susceptible to enzymatic degradation.

Biodegradable linkages may be chosen so that a hydrogel is readily degradable. One method of determining that a hydrogel is substantially degraded is to perform an in vitro degradation test, as set forth in Example 13. These tests are generally predictive for degradation in animals, as shown in Examples 13, 15, and 17, as shown in FIG. 46. FIG. 46 shows that in vitro degradation of a trilysine-based hydrogel was about forty days in vitro, and about thirty-eight days in vivo. Thus, for example, a hydrogel may be made using only polymers that have hydrolytically degradable ester groups and no other groups that are enzymatically degradable or degrade by hydrolysis. Other embodiments include hydrogels made using isolated hydrolytically degradable ester groups as the biodegradable linkages. The term "hydrolytically degradable ester group" means an ester group that degrades spontaneously in aqueous solution; such esters will be hydrolyzed in vitro in water, free of enzymes or bacteria, when kept at 37° C. The Application describes a wide variety of materials made with hydrolytically degradable ester groups. In some of these embodiments, the materials degrade to components that are too small to be observed with the naked eye or small enough to dissolve into aqueous solutions, with the result that the materials seem to disappear over time when exposed to water.

Visualization Agents

Where convenient, the biocompatible crosslinked polymer or precursor solutions (or both) may contain visualization agents to improve their visibility during surgical procedures. Visualization agents are especially useful when used in MIS procedures, due among other reasons to their improved visibility on a color monitor.

Visualization agents may be selected from among any of the various non-toxic colored substances suitable for use in medical implantable medical devices, such as FD&C BLUE dyes 3 and 6, eosin, methylene blue, indocyanine green, or colored dyes normally found in synthetic surgical sutures. The preferred color is green or blue because it has better visibility in presence of blood or on a pink or white tissue background. Red is the least preferred color, when used on a highly vascularized tissue that is red in color. However, red may be suitable when the underlying tissue is white, for example the cornea.

The visualization agent may be present with either reactive precursor species, e.g., a crosslinker or functional polymer solution. The preferred colored substance may or may not become chemically bound to the hydrogel. The visualization agent may be used in small quantities, preferably less than 1% weight/volume, more preferably less that 0.01% weight/volume and most preferably less than 0.001% weight/volume concentration.

Additional visualization agents may be used, such as fluorescent (e.g., green or yellow fluorescent under visible light) compounds (e.g., fluorescein or eosin), x-ray contrast agents (e.g., iodinated compounds) for visibility under x-ray imaging equipment, ultrasonic contrast agents, or MRI contrast agents (e.g., Gadolinium containing compounds).

A visualization agent may be used to allow the user to determine the thickness of the applied hydrogel. The visualization agent is preferably an agent that provides a color that is visible to the human eye, e.g., a color that is detected visually by the user or detected by a video camera and relayed to a video screen observed by the user.

Visually observable visualization agents are preferred. Wavelengths of light from about 400 to 750 nm are observable to the human as colors (R. K. Hobbie, Intermediate Physics for Medicine and Biology, $2^{nd}$ Ed., pages 371-373). Blue color is perceived when the eye receives light that is predominantly from about 450 to 500 nm in wavelength and green is perceived at about 500 to 570 nm (Id.). The color of an object is therefore determined by the predominant wavelength of light that it reflects or emits. Further, since the eye detects red or green or blue, a combination of these colors may be used to simulate any other color merely by causing the eye to receive the proportion of red, green, and blue that is perceived as the desired color by the human eye. Blue and green visualization agents are preferred since they are most readily visible when observing in situ crosslinking due to the approximately red color of the background color of tissue and blood. The color blue, as used herein, means the color that is perceived by a normal human eye stimulated by a wavelength of about 450 to 500 nm and the color green, as used herein, means the color that is perceived by a normal human eye stimulated by a wavelength of about 500 to 570 nm.

The use of a visualization agent may be used when a hydrogel is used to coat a substrate. A substrate coating surface is a surface of a hydrogel that contacts a substrate and, in the region of contact, is essentially in continuous contact with that substrate. Although some small portions of the coating or substrate may not be in contact, the contact is intimate. A substrate coating surface can be formed when the hydrogel crosslinks after contacting the substrate surface because the contact before crosslinking allows the hydrogel precursors to mix and conform to the shape of the substrate. A preformed hydrogel material generally does not have a substrate coating surface. A suitable substrate is a tissue of a patient.

An embodiment is a hydrogel for use on a patient's tissue that has water, a biocompatible visualization agent, and crosslinked hydrophilic polymers that form a hydrogel after contact with the tissue. The hydrogel coats the tissue and also has a free surface. The visualization agent reflects or emits light at a wavelength detectable to a human eye so that a user applying the hydrogel can observe the gel and also estimate its thickness.

A hydrogel with a substrate coating surface may also have a free surface when the hydrogel is used for prevention of adhesions. The hydrogel is applied to a tissue and crosslinks while having one free surface that is not adherent to any tissue but is instead freely movable relative to any tissues that it may subsequently contact. The free surface prevents the coated tissue from contact with other tissues and does not prevent the movement of other tissues so that protection and free movement are optimal. In this situation, a user that applies the hydrogel may observe the hydrogel by looking through the free surface into the hydrogel and at the coated tissue.

Some suitable biocompatible visualization agents are FD&C BLUE #1, FD&C BLUE #2, and methylene blue. These agents may be present in the final electrophilic-nucleophilic reactive precursor species mix at a concentration of more than 0.05 mg/ml, in a concentration range of at least 0.1 to about 12 mg/ml, and in the range of 0.1 to 4.0 mg/ml, although greater concentrations may potentially be used, up to the limit of solubility of the visualization agent. These concentration ranges were found to give a color to the hydrogel that was desirable without interfering with crosslinking times (as measured by the time for the reactive precursor species to gel). The visualization agent may also be a fluorescent molecule.

Crosslinking Reactions

The crosslinking reactions preferably occur in aqueous solution under physiological conditions. More preferably the crosslinking reactions occur "in situ", meaning they occur at local sites such as on organs or tissues in a living animal or human body. More preferably the crosslinking reactions do not release heat of polymerization. Preferably the crosslinking reaction leading to gelation occurs within about 10 minutes, more preferably within about 2 minutes, more preferably within about one minute, and most preferably within about 30 seconds. When it is desirable to build up a coating on a convex surface, the crosslinking reaction preferably occurs within about 2 minutes, more preferably in 30-60 seconds, and most preferably in 2-4 seconds.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Several methods for activating such functional groups are known in the art. Preferred activating groups include carbonyldiimidazole, sulfonyl chloride, aryl halides, sulfosuccinimidyl esters, N-hydroxysuccinimidyl ester, succinimidyl ester, epoxide, aldehyde, maleimides, imidoesters and the like. The N-hydroxysuccinimide esters or N-hydroxysulfosuccinimide groups are the most preferred groups for crosslinking of proteins or amine functionalized polymers such as amino terminated polyethylene glycol ("APEG").

FIGS. 1 to 5 illustrate various embodiments of preferred crosslinkers and functional polymers. FIG. 1 illustrates possible configurations of degradable electrophilic crosslinkers or functional polymers. The biodegradable regions are represented by (^^^^^^); the functional groups are represented by ( ◄ )and the inert water soluble cores are represented by (—). For crosslinkers, the central core is a water soluble small molecule and for functional polymers the central core is a water soluble polymer of natural or synthetic origin.

When Structure A in FIG. 1 is a functional polymer, it is a linear water soluble and biodegradable functional polymer, end-capped with two functional groups (e.g., N-hydroxysuccinimide ester or NHS, epoxide or similar reactive groups). The water soluble core may be a polyalkylene oxide, preferably polyethylene glycol block copolymer, and it is extended with at least one biodegradable linkage between it and each terminal functional group. The biodegradable linkage may be a single linkage or copolymers or homopolymers of absorbable polymers such as polyhydroxy acids or polylactones.

When Structure B in FIG. 1 is a functional polymer it is a branched or star shaped biodegradable functional polymer which has an inert polymer at the center. Its inert and water soluble core is terminated with oligomeric biodegradable extensions, which in turn are terminated with reactive functional groups.

When Structures C and D in FIG. 1 are functional polymers, they are multifunctional 4 arm biodegradable functional polymers. This polymer again has a water-soluble soluble core at the center, which is a 4 arm, tetrafunctional polyethylene glycol (Structure C) or block copolymer of PEO-PPO-PEO such as TETRONIC 908 (Structure D) which is extended with by small oligomeric extensions of biodegradable polymer to maintain water solubility and terminated with reactive functional end-groups such as CDI or NHS.

When Structure E in FIG. 1 is a functional polymer, it is a multifunctional star or graft type biodegradable polymer. This polymer has a water-soluble polymer like polyethylene oxide, polyvinyl alcohol or poly(vinyl pyrrolidinone) at the core which is completely or partially extended with biodegradable polymer. The biodegradable polymer is terminated with reactive end groups.

Structures A-E in FIG. 1 need not have polymeric cores and may be small molecule crosslinkers. In that case, the core may comprise a small molecule like ethoxylated glycerol, inositol, trimethylolpropane etc. to form the resultant crosslinker. In addition, Structures A-E in FIG. 1 need not have polymeric biodegradable extensions, and the biodegradable extensions may consist of small molecules like succinate or glutarate or combinations of 2 or more esters, such as glycolate/2-hydroxybutyrate or glycolate/4-hydroxyproline, etc. A dimer or trimer of 4-hydroxyproline may be used not only to add degradability, but also to add nucleophilic functional group reactive sites via the pendant primary amines which are part of the hydroxyproline moiety.

Other variations of the core, the biodegradable linkage, and the terminal electrophilic group in Structures A-E in FIG. 1 may be constructed, so long as the resulting functional polymer has the properties of low tissue toxicity, water solubility, and reactivity with nucleophilic functional groups.

FIG. 2 illustrates various embodiments of nucleophilic biodegradable water soluble crosslinkers and functional polymers suitable for use with electrophilic functional polymers and crosslinkers described herein. The biodegradable regions are represented by ( ^^^^^^ ) the functional groups are represented by (|); and the inert water soluble cores are represented by (—). For crosslinkers, the central core is a water soluble small molecule and for functional polymers the central core is a water soluble polymer of natural or synthetic origin.

When Structure F in FIG. 2 is a functional polymer, it is a linear water soluble biodegradable polymer terminated with reactive functional groups like primary amine. The linear water-soluble core is a polyalkylene oxide, preferably polyethylene glycol block copolymer, which is extended with the biodegradable region which is a copolymer or homopolymers of polyhydroxy acids or polylactones. This biodegradable polymer is terminated with primary amines. When Structure G in FIG. 2 is a functional polymer, it is a branched or star shaped biodegradable polymer which has an inert polymer at the center. The inert polymer is extended with single or oligomeric biodegradable extensions which are terminated with reactive functional groups. When Structures H and I in FIG. 2 are functional polymers, they are multifunctional 4 arm biodegradable polymers. These polymers again have water-soluble cores at their center which are either a 4 arm, tetrafunctional polyethylene glycol (Structure H) or a block copolymer of PEO-PPO-PEO such as TETRONIC 908 (Structure I), extended with small oligomeric extensions of biodegradable polymers to maintain water solubility, and terminated with functional groups such as amines and thiols.

When Structure J in FIG. 2 is a functional polymer, it is a multifunctional star or graft type biodegradable polymer. This polymer has a water soluble polymer like polyethylene oxide, polyvinyl alcohol or poly(vinyl pyrrolidinone) at the core which is completely or partially extended with biodegradable polymer. The biodegradable polymer is terminated with reactive end groups. Structures F-J in FIG. 2 need not have polymeric cores and may be small molecule crosslinkers. In that case, the core may comprise a small molecule like ethoxylated glycerol, inositol, trimethylolpropane etc. to form the resultant crosslinker. Other variations of the core, the biodegradable linkage, and the terminal nucleophilic functional group in Structures F-J in FIG. 2 may be constructed, so long as the resulting functional polymer has the properties of low tissue toxicity, water solubility, and reactivity with electrophilic functional groups.

Figure 3K:
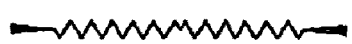
FIG. 3 depicts electrophilic water soluble and biodegradable crosslinkers or functional polymers, which can be crosslinked with appropriate nucleophilic functional group precursors, wherein either the biodegradable linkages or the functional groups are selected so as to make the precursor water soluble.
Figure 3L:
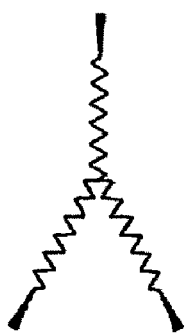

FIG. 3 illustrates configurations of water-soluble electrophilic crosslinkers or functional polymers where the core is biodegradable. The biodegradable regions are represented by ( ˄˄˄˄˄˄ ) and the functional groups are represented by ( ◀ ) The biodegradable core is terminated with a reactive functional group that is also water solubilizing, such a N-hydroxysulfosuccinimide ester ("SNHS") or N-hydroxyethoxylated succinimide ester ("ENHS"). Structure K in FIG. 3 depicts a difunctional biodegradable polymer or oligomer terminated with SNHS or ENHS. The oligomers and polymers may be made of a poly(hydroxy acid) such as poly(lactic acid), which is insoluble in water. However, the terminal carboxylic acid group of these oligomers or polymers can be activated with N-hydroxysulfosuccinimide ester ("SNHS") or N-hydroxyethoxylated succinimide ester ("ENHS") groups. An ionic group, like a metal salt (preferably sodium salt) of sulfonic acid, or a nonionic group, like a polyethylene oxide on the succinimide ring, provides water-solubility while the NHS ester provides chemical reactivity towards amines. The sulfonate groups (sodium salts) or ethoxylated groups on the succinimide ring solubilize the oligomer or polymer without appreciably inhibiting reactivity towards amine groups. Structures L-0 in FIG. 3 represent multibranched or graft type structures with terminal SNHS or ENHS group. The cores may comprise various non-toxic polyhydroxy compounds like sugars (xylitol, erythritol), glycerol, trimethylolpropane, which have been reacted with anhydrides such as succinic or glutaric anhydrides. The resultant acid groups were then activated with SNHS or ENHS groups to form water soluble crosslinkers or functional polymers.

Figure 4R:
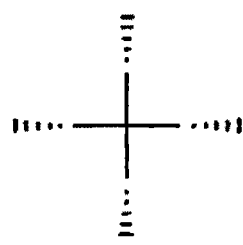
FIG. 4 depicts nucleophilic functional group water soluble crosslinkers or functional polymers, which can be crosslinked with appropriate electrophilic functional group precursors, and which are not biodegradable.
Figure 4S:
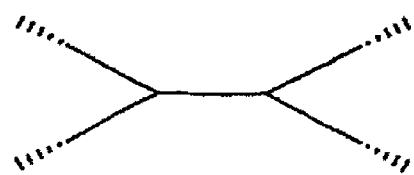
Figure 5U:
FIG. 5 depicts electrophilic water soluble crosslinkers or functional polymers, which can be crosslinked with appropriate nucleophilic functional group precursors, and which are not biodegradable.
Figure 5V:
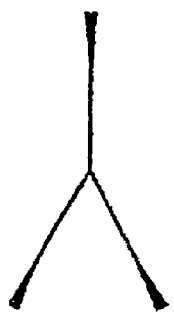
Figure 5W:
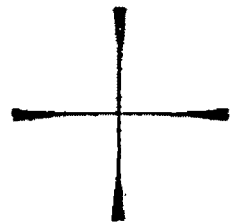
Figure 5Y:
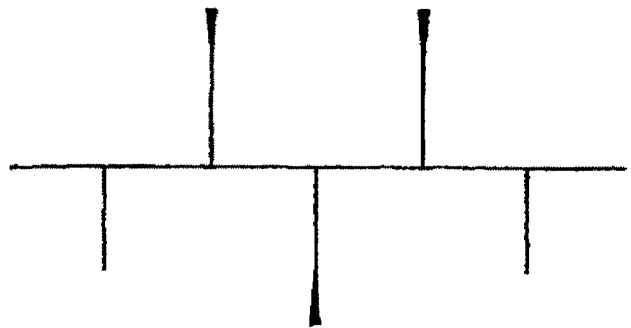
Figure 5X:
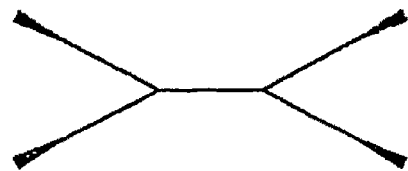

FIG. 4 illustrates various nucleophilic functional polymers or crosslinkers that are not biodegradable. The nucleophilic functional groups are represented by (|) and the inert water-soluble cores are represented by (—). For crosslinkers, the central core is a water-soluble small molecule and for functional polymers the central core is a water soluble polymer of natural or synthetic origin. When Structure P in FIG. 4 is a functional polymer it may be a water-soluble linear polymer such as polyethylene glycol terminated with reactive end group such as primary amines and thiols. Such polymers are commercially available from Sigma (Milwaukee, Wis.) and Shearwater Polymers (Huntsville, Ala.). Some other preferred difunctional polymers are PPO-PEO-PPO block copolymers such as PLURONIC F68 terminated with amine groups. PLURONIC or TETRONIC polymers are normally available with terminal hydroxyl groups. The hydroxyl groups are converted into amine groups by methods known in the art. When Structures Q-T in FIG. 4 are functional polymers they may be multifunctional graft or branch type water soluble copolymers with terminal amine groups. Structures P-T in FIG. 4 need not have polymeric cores and may be small molecule crosslinkers. In that case, the core may comprise a small molecule like ethoxylated glycerol, inositol, trimethylolpropane, dilysine etc. to form the resultant crosslinker. Other variations of the core and the terminal nucleophilic functional group in Structure P-T in FIG. 4 may be employed, so long as the properties of low tissue toxicity, water solubility, and reactivity with electrophilic functional groups are maintained.

FIG. 5 illustrates various electrophilic functional polymers or crosslinkers that are not biodegradable. The electrophilic functional groups are represented by (|) and the inert water soluble cores are represented by (—). For crosslinkers, the central core is a water soluble small molecule and for functional polymers the central core is a water soluble polymer of natural or synthetic origin. When Structure U is a functional polymer, it may be a water-soluble polymer such as polyethylene glycol terminated reactive end group such as NHS or epoxide. Such polymers are commercially available from Sigma and Shearwater polymers. Some other preferred polymers are PPO-PEO-PPO block copolymers such as PLURONIC F68 terminated with NHS or SNHS group. PLURONIC or TETRONIC polymers are normally available with terminal hydroxyl groups. The hydroxyl groups are converted into acid group by reacting with succinic anhydride. The terminated acid groups are reacted with N-hydroxysuccinimide in presence of DCC to generate NHS activated PLURONIC polymer. When Structures V-Y are functional polymers they may be multifunctional graft or branch type PEO or PEO block copolymers (TETRONICS) activated with terminal reactive groups such as NHS. Structures U-Y in FIG. 5 need not have polymeric cores and may be small molecule crosslinkers. In that case, the core may comprise a small molecule like ethoxylated glycerol, tetraglycerol, hexaglycerol, inositol, trimethylolpropane, dilysine etc. to form the resultant crosslinker. Other variations of the core and the terminal nucleophilic functional group in Structures U-Y in FIG. 5 may be employed, so long as the properties of low tissue toxicity, water solubility, and reactivity with electrophilic functional groups are maintained.

Preparation of Structures A-Y in FIGS. 1-5

The polymeric crosslinkers and functional polymers illustrated as Structures A-Y in FIGS. 1 to 5 may be prepared using variety of synthetic methods. Their preferred compositions are described in Table 1.

TABLE 1

Suitable Crosslinkers and Functional Polymers

| Structure | Brief Description | Typical Example |
|---|---|---|
| A | Water soluble, linear difunctional crosslinker or functional polymer with water soluble core, extended with biodegradable regions such as oligomers of hydroxyacids or peptide sequences which are cleavable by enzymes and terminated with protein reactive functional groups | Polyethylene glycol or ethoxylated propylene glycol chain extended with oligolactate and terminated with N-hydroxysuccinimide esters |
| B | Water soluble, trifunctional crosslinker or functional polymer with water soluble core, extended with biodegradable regions such as oligomers of hydroxyacids or peptide sequences and terminated with protein reactive functional groups | Ethoxylated glycerol chain extended with oligolactate and terminated with N-hydroxysuccinimide esters |
| C | Water soluble, tetrafunctional crosslinker or functional polymer with water soluble core, extended with biodegradable regions such as oligomers of hydroxyacids or peptide sequences and terminated with protein reactive functional groups | 4 arm polyethylene glycol, erythritol or pentaerythritol or pentaerythritol chain extended with oligolactate and terminated with N-hydroxysuccinimide esters |
| D | Water soluble, tetrafunctional crosslinker or functional polymer with water soluble core, extended with biodegradable regions such as oligomers of hydroxyacids or peptide sequences and terminated with protein reactive functional groups | Ethoxylated ethylene diamine or polyethylene oxide-polypropylene oxide-polyethylene oxide block copolymer like TETRONIC 908 chain extended with oligotrimethylene carbonate and terminated with N-hydroxysuccinimide ester |
| E | Water soluble, branched crosslinker or functional polymer with water soluble core, extended with biodegradable regions such as oligomers of hydroxyacids or peptide sequences and terminated with protein reactive functional groups | Low molecular weight polyvinyl alcohol with 1% to 20% hydroxyl groups extended with oligolactate and terminated with N-hydroxysuccinimide ester |
| F | Water soluble, liner difunctional crosslinker or functional polymer with water soluble core, extended with biodegradable regions such as oligomers of hydroxyacids or peptide sequences and terminated with amines, carboxylic acid or thiols | Polyethylene oxide-polypropylene oxide-polyethylene oxide block copolymer surfactant like PLURONIC F68 chain extended with oligolactate and terminated with amino acids such as lysine or peptide sequences that may contain two amine groups |
| G | Water soluble, trifunctional crosslinker or functional polymer with water soluble core, extended with biodegradable regions such as oligomers of hydroxyacids or peptide sequences and terminated with amines, carboxylic acid or thiols | Ethoxylated glycerol chain extended with oligolactate and terminated with aminoacid such as lysine |
| H | Water soluble, tetrafunctional crosslinker or functional polymer with water soluble core, extended with biodegradable regions such as oligomers of hydroxyacids or peptide sequences and terminated with amines, carboxylic acid or thiols | 4 arm polyethylene glycol or tetra erythritol chain extended with oligolactate and terminated with aminoacid such as lysine |
| I | Water soluble, tetrafunctional crosslinker or functional polymer with water soluble core, extended with biodegradable regions such as oligomers of hydroxyacids or peptide sequences and terminated with amines, carboxylic acid or thiols | Ethoxylated ethylene diamine or polyethylene oxide-polypropylene oxide-polyethylene oxide block copolymer like TETRONIC 908 chain extended with oligotrimethylene carbonate and terminated with aminoacid such as lysine |
| J | Water soluble, multifunctional or graft type crosslinker or functional polymer with water soluble core, extended with biodegradable regions such as oligomers of hydroxyacids or peptide sequences and terminated with amines, carboxylic acid or thiols | Low molecular weight polyvinyl alcohol with 1-20% hydroxyl groups extended with oligolactate and terminated with aminoacid such as lysine |
| K | Water soluble, linear difunctional crosslinker or functional polymer such as oligomers of hydroxyacids or peptide sequences which are terminated with protein reactive functional groups | Difunctional oligolactic acid with terminal carboxyl groups which are activated with n-hydroxysulfosuccinimide ester or ethoxylated n-hydroxysuccinimide ester. |
| L | Water soluble branched trifunctional crosslinker or functional polymer such as oligomers of hydroxyacids or peptide sequences which are terminated with protein reactive functional groups | Trifunctional oligocaprolactone with terminal carboxyl groups which are activated with n-hydroxysulfosuccinimide ester or ethoxylated n-hydroxysuccinimide ester. |
| M | Water soluble, branched tetrafunctional crosslinker or functional polymer such as oligomers of hydroxyacids or peptide sequences which are terminated with protein reactive functional groups | Tetrafunctional oligocaprolactone with terminal carboxyl groups which are activated with n-hydroxysulfosuccinimide ester or ethoxylated n-hydroxysuccinimide ester. |
| N | Water soluble, branched tetrafunctional crosslinker or functional polymer such as oligomers of hydroxyacids or peptide sequences which are terminated with protein reactive functional groups | Tetrafunctional oligocaprolactone with terminal carboxyl groups which are activated with n-hydroxysulfosuccinimide ester or ethoxylated n-hydroxysuccinimide ester. |
| O | Water soluble, branched multifunctional crosslinker or functional polymer such as oligomers f hydroxyacids or peptide sequences which are terminated with protein reactive functional groups | Multifunctional oligolactic acid with terminal carboxyl groups which are activated with n-hydroxysulfosuccinimide ester or ethoxylated n-hydroxysuccinimide ester. |
| P | Water soluble, linear difunctional crosslinker or functional polymer terminated with amines, carboxylic acid or thiols functional groups | Polyethylene glycol with terminal amines groups |
| Q | Water soluble, branched trifunctional crosslinker or functional polymer terminated with amines, carboxylic acid or thiols as functional group | Ethoxylated glycerol with terminal amines groups |
| R | Water soluble, branched tetrafunctional crosslinker of functional polymer terminated with amines, carboxylic acid or thiols functional groups | 4 arm polyethylene glycol modified to produce terminal amine groups |
| S | Water soluble, branched tetrafunctional crosslinker or functional polymer terminated with amines, carboxylic acid or thiols functional groups | Ethoxylated ethylene diamine or polyethylene oxide-polypropylene oxide-polyethylene oxide block copolymer like TETRONIC 908 modified to generate terminal amine groups |
| T | Water soluble, branched or graft crosslinker or functional | Polylysine, albumin, polyallyl amine |

TABLE 1-continued

Suitable Crosslinkers and Functional Polymers

| Structure | Brief Description | Typical Example |
|---|---|---|
| | polymer with terminal amines, carboxylic acid or thiols functional groups | |
| U | Water soluble, linear difunctional crosslinker or functional polymer terminated with protein reactive functional groups | Polylysine, albumin, polyallyl amine |
| V | Water soluble branched trifunctional crosslinker or functional polymer terminated with protein reactive functional groups | Ethoxylated glycerol terminated with n-hydroxysuccinimide |
| W | Water soluble branched tetrafunctional crosslinker or functional polymer terminated with protein reactive functional groups | 4 arm polyethylene glycol terminated with n-hydroxysuccinimide esters |
| X | Water soluble branched tetrafunctional crosslinker or functional polymer terminated with protein reactive functional groups | Ethoxylated ethylene diamine or polyethylene oxide-polypropylene oxide-polyethylene oxide block copolymer like TETRONIC 908 with n-hydroxysuccinimide ester as end group |
| Y | Water soluble, branched or graft polymer crosslinker or functional polymer with protein reactive functional groups | Poly (vinyl pyrrolidinone)-co-poly (n-hydroxysuccinimide acrylate) copolymer (9:1), molecular weight <40000 Da |

First, the biodegradable links of Structures A-J in FIGS. 1 and 2 may be composed of specific di or multifunctional synthetic amino acid sequences which are recognized and cleaved by enzymes such as collagenase, and may be synthesized using methods known to those skilled in the peptide synthesis art. For example, Structures A-E in FIG. 1 may be obtained by first using carboxyl, amine or hydroxy terminated polyethylene glycol as a starting material for building a suitable peptide sequence. The terminal end of the peptide sequence is converted into a carboxylic acid by reacting succinic anhydride with an appropriate amino acid. The acid group generated is converted to an NHS ester by reaction with N-hydroxysuccinimide.

The functional polymers described in FIG. 2 may be prepared using a variety of synthetic methods. In a preferred embodiment, the polymer shown as Structure F may be obtained by ring opening polymerization of cyclic lactones or carbonates initiated by a dihydroxy compound such as PLURONIC F 68 in the presence of a suitable catalyst such as stannous 2-ethylhexanoate. The molar equivalent ratio of caprolactone to PLURONIC is kept below 10 to obtain a low molecular weight chain extension product so as to maintain water solubility. The terminal hydroxyl groups of the resultant copolymer are converted into amine or thiol by methods known in the art.

In a preferred method, the hydroxyl groups of a PLURONIC-caprolactone copolymer are activated using tresyl chloride. The activated groups are then reacted with lysine to produce lysine terminated PLURONIC-caprolactone copolymer. Alternatively, an amine-blocked lysine derivative is reacted with the hydroxyl groups of a PLURONIC-caprolactone copolymer and then the amine groups are regenerated using a suitable deblocking reaction.

Structures G, H, I and J in FIG. 2 may represent multifunctional branched or graft type copolymers having water soluble core extended with oligohydroxy acid polymer and terminated with amine or thiol groups.

Figure 6:
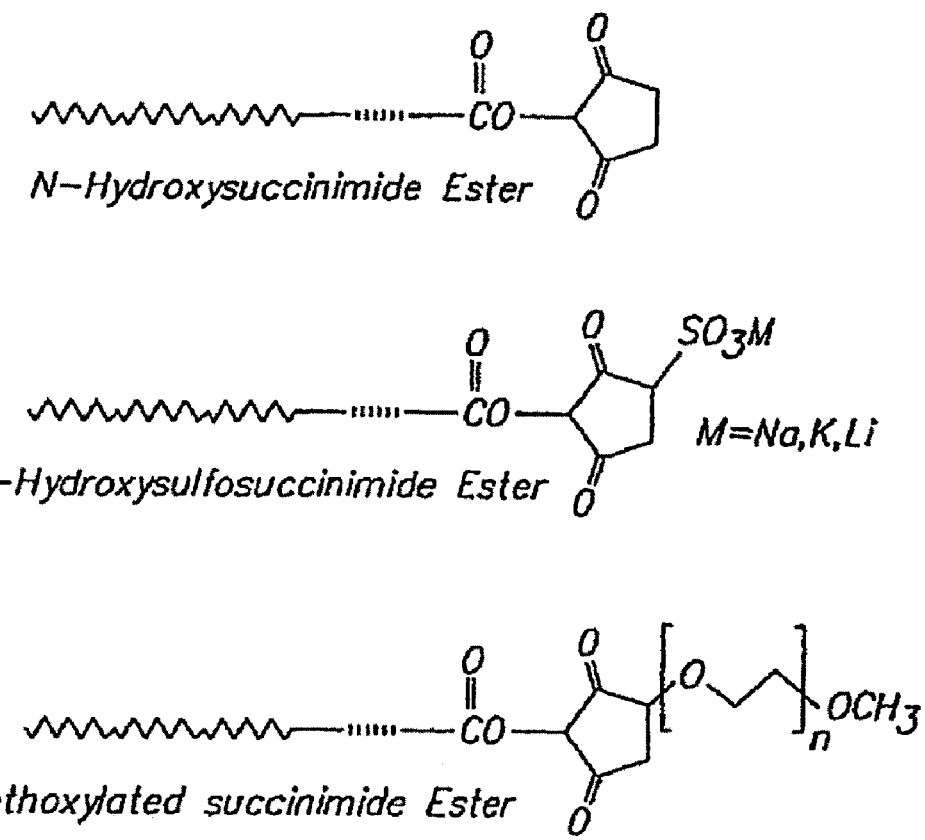
FIG. 6 depicts certain N-hydroxysuccinimide (NHS) esters.
Figure 7:
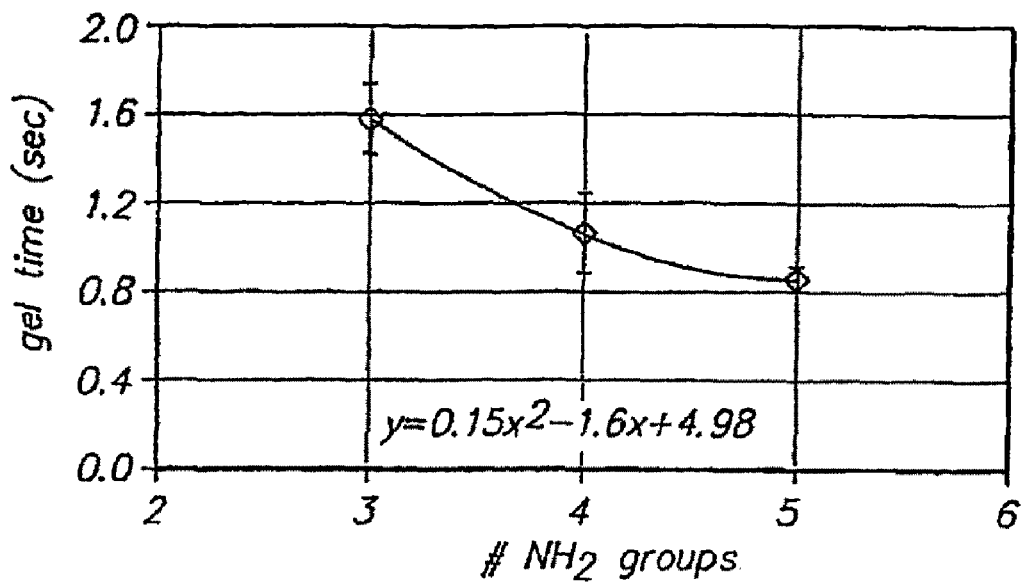
FIG. 7 shows the variation in gelation time plotted against the number of amino groups for the precursors of Examples 2-4, wherein 4 arm 10 kDa succinimidyl glutarate PEG ("SG-PEG") was reacted with di-, tri- or tetra-lysine.

For example, in a preferred embodiment, the functional polymer illustrated as Structure G in FIG. 2 is obtained by ring opening polymerization of cyclic lactones or carbonates initiated by a tetrahydroxy compound such as 4 arm, tetrahydroxy polyethylene glycol (molecular weight 10,000 Da), in the presence of a suitable catalyst such as stannous octoate. The molar equivalent ratio of cyclic lactone or carbonate to PEG is kept below 10 to obtain a low molecular weight extension, and to maintain water solubility (polymers of cyclic lactones generally are not as water soluble as PEG). Alternatively, hydroxyacid as a biodegradable link may be attached to the PEG chain using blocking/deblocking chemistry known in the peptide synthesis art. The terminal hydroxy groups of the resultant copolymer are activated using a variety of reactive groups known in the art. The CDI activation chemistry and sulfonyl chloride activation chemistry is shown in FIGS. 6 and 7, respectively, of U.S. application Ser No. 10/010,715.

The most preferred reactive groups are N-hydroxysuccinimide esters, synthesized by any of several methods. In a preferred method, hydroxyl groups are converted to carboxylic groups by reacting them with anhydrides such as succinic anhydride in the presence of tertiary amines such as pyridine or triethylamine or dimethylaminopyridine ("DMAP"). Other anhydrides such as glutaric anhydride, phthalic anhydride, maleic anhydride and the like may also be used. The resultant terminal carboxyl groups are reacted with N-hydroxysuccinimide in the presence of dicyclohexylcarbodiimide ("DCC") to produce N-hydroxysuccinimide ester (referred as NHS activation). Suitable N-hydroxysuccinimide esters are shown in FIG. 6.

In a preferred embodiment, the polymer shown as structure H is obtained by ring opening polymerization of glycolide or trimethylene carbonate initiated by a tetrahydroxy compound such as tetrafunctional polyethylene glycol (molecular weight 2000 Da) in the presence of a catalyst such as stannous 2-ethylhexoate. The molar equivalent ratio of glycolide to PEG is kept from 2 to 10 to obtain a low molecular weight extension. The terminal hydroxy groups of the resultant copolymer are converted into amine groups by reaction with lysine as mentioned previously. Similar embodiments can be obtained using analogous chain extension synthetic strategies to obtain structures F, G, I and J by starting with the appropriate corresponding polyol.

Structures K, L, M, N and O in FIG. 3 are made using a variety of synthetic methods. In a preferred embodiment, the polymer shown as Structure L in FIG. 3 is obtained by ring opening polymerization of cyclic lactones by a trihydroxy compound such as glycerol in the presence of a catalyst such as stannous 2-ethylhexanoate. The molar equivalent ratio of cyclic lactone to glycerol is kept below 2, so that only low molecular weight oligomers are obtained. The low molecular weight oligomer ester is insoluble in water. The terminal hydroxy groups of the resultant copolymer are activated using N-hydroxysulfosuccinimide groups. This is achieved by converting hydroxy groups to carboxylic groups by reacting with anhydrides such as succinic anhydride in presence of tertiary amines. The resultant terminal carboxyl groups are reacted with N-hydroxysulfosuccinimide or N-hydroxyethoxylated succinimide in the presence of dicyclohexylcarbodiimide ("DCC") to produce a sulfonated or ethoxylated NHS ester. The sulfonate or PEO chain on the succinimide ring gives water solubility to the oligoester.

The foregoing method generally is applied to solubilize only low molecular weight multi-branched oligoesters, with molecular weights below 1000. In another variation of this method, various non-toxic polyhydroxy compounds, preferably sugars, such as erythritol, xylitol are reacted with succinic anhydride in the presence of a tertiary amine. The terminal carboxyl group of succinated erythritol is esterified with N-hydroxysulfosuccinimide (FIG. 6). Similar embodiments may be obtained using analogous synthetic strategies to obtain structures K, and M-O by starting with the appropriate starting materials.

Structures P-R may be synthesized by reacting the appropriate starting material, such as a linear (P) or 2- or 3-arm branched PEG (Q, R) with hydroxy end groups, with lysine as mentioned previously, such that the arms of the PEG oligomers are capped with amine end groups. Structure S may be synthesized, using a multistep reaction, from PEG, glycerol and a diisocyanate. In the first step a PEG diol is reacted with excess diisocyanate, such as 4,4'diphenyl methane diisocyanate ("MDI"), methylene-bis(4-cyclohexylisocyanate) ("HMDI") or hexamethylenediisocyanate ("HDI"). After purification the resultant PEG diisocyanate is added dropwise to excess glycerol or trimethylol propane or other triol and reacted to completion. The purified product, now having diol end groups, is again reacted with excess diisocyanate and purified, yielding a PEG-tetra-isocyanate. This tetrafunctional PEG subsequently may be reacted with excess PEG diols, yielding a 4 arm PEG synthesized from a PEG diol oligomer. In the final step lysine end groups are incorporated, as discussed previously.

Structure T may be synthesized as follows: First synthesize a random copolymer of PEG-monoacrylate and some other acrylate or combination of acrylates, such that the final polyacrylate is water soluble. Other acrylates include, but are not limited to, 2-hydroxyethylacrylate, acrylic acid, and acrylamide. Conditions may be varied to control the molecular weight as desired. In the final step, the acrylate is reacted with lysine as discussed previously, using an appropriate quantity to achieve the desired degree of amination.

One method of synthesizing Structures U-Y is to use dicyclohexylcarbodiimide coupling to a carboxylate end group. For Structures U-W, one can react the appropriate PEG-diol, -triol or -tetra-hydroxy starting material with excess succinic anhydride or glutaric anhydride such that all end groups are effectively carboxylated. Structures X and Y may be made in a manner similar to that used for Structures S and T, except that in the last step instead of end capping with lysine, end capping with succinic anhydride or glutaric anhydride is performed.

Preparation of Biocompatible Polymers

Several biocompatible crosslinked hydrogels may be produced using the crosslinkers and functional polymers described in FIGS. 1 to 5. Preferred combinations of such polymers suitable for producing such biocompatible crosslinked polymers are described in Table 2. In Table 2, the crosslinker functional groups are N-hydroxy succinimide esters and the functional polymer functional groups are primary amines.

TABLE 2

Biocompatible Polymers Synthesized from Crosslinkers and Functional Polymers of Table 1

| Crosslinker Structure | Functional Polymer Structure | Concentration | Medium |
| --- | --- | --- | --- |
| B or C | H and R | Molar Equivalent; >20% W/V | Borate or triethanol amine buffer, pH 7-10 |
| A, B or C | H, P, Q, R and S | Molar Equivalent; >20% W/V | Borate or triethanol amine buffer, pH 7-10 |
| Y | T, H, P and Q | Molar Equivalent; >10% W/V | Borate or triethanol amine buffer, pH 7-910 |
| W, V | H and J | Molar Equivalent; >20% W/V | Bicarbonate buffer, pH 7-10 |
| X | I, J and H | Molar Equivalent; >20% W/V | Borate or triethanol amine buffer, pH 7-10 |

The reaction conditions for crosslinking will depend on the nature of the functional groups. Preferred reactions are conducted in buffered aqueous solutions at pH 5 to 12. The preferred buffers are sodium borate buffer (pH 10) and triethanol amine buffer (pH 7). Elevated pH increases the speed of electrophilic-nucleophilic reactions. In some embodiments, organic solvents such as ethanol or isopropanol may be added to improve the reaction speed or to adjust the viscosity of a given formulation.

Many of synthetic crosslinked gels described herein degrade due to hydrolysis of the biodegradable region, especially by hydrolysis of the isolated ester in the polymer. The degradation of gels containing synthetic peptide sequences will depend on the specific enzyme and its concentration. In some cases, a specific enzyme may be added during the crosslinking reaction to accelerate the degradation process.

When the crosslinker and functional polymers are synthetic (for example, when they are based on polyalkylene oxide), then it is desirable and in some cases essential to use molar equivalent quantities of the reactants. In some cases, molar excess crosslinker may be added to compensate for side reactions such as reactions due to hydrolysis of the functional group.

When choosing the crosslinker and crosslinkable polymer, at least one of polymers must have more than 2 functional groups per molecule and at least one degradable region, if it is desired that the resultant biocompatible crosslinked polymer be biodegradable. For example, the difunctional crosslinker shown as Structure A in FIG. 1 cannot form a crosslinked network with the difunctional polymers shown as Structure F in FIG. 2 or Structure P in FIG. 4. Generally, it is preferred that each biocompatible crosslinked polymer precursor have more than 2 and more preferably 4 or more functional groups.

Preferred electrophilic functional groups are NHS, SNHS and ENHS (FIG. 6). Preferred nucleophilic functional groups are primary amines. The advantage of the NHS-amine reaction is that the reaction kinetics lead to quick gelation usually within 10 about minutes, more usually within about 1 minute and most usually within about 10 seconds. This fast gelation is preferred for in situ reactions on live tissue.

The NHS-amine crosslinking reaction leads to formation of N-hydroxysuccinimide as a side product. The sulfonated or ethoxylated forms of N-hydroxysuccinimide are preferred due to their increased solubility in water and hence their rapid clearance from the body. The sulfonic acid salt on the succinimide ring does not alter the reactivity of NHS group with the primary amines.

The NHS-amine crosslinking reaction may be carried out in aqueous solutions and in the presence of buffers. The preferred buffers are phosphate buffer (pH 5.0-7.5). triethanolamine buffer (pH 7.5-9.0) and borate buffer (pH 9.0-12)

and sodium bicarbonate buffer (pH 9.0-10.0). Aqueous solutions of NHS based crosslinkers and functional polymers preferably are made just before the crosslinking reaction due to reaction of NHS groups with water. Longer "pot life" may be obtained by keeping these solutions at lower pH (pH 4-5). The crosslinking density of the resultant biocompatible crosslinked polymer is controlled by the overall molecular weight of the crosslinker and functional polymer and the number of functional groups available per molecule. A lower molecular weight between crosslinks such as 600 will give much higher crosslinking density as compared to a higher molecular weight such as 10,000. Higher molecular weight functional polymers are preferred, preferably more than 3000 so as to obtain elastic gels. The crosslinking density also may be controlled by the overall percent solids of the crosslinker and functional polymer solutions. Increasing the percent solids increases the probability that an electrophilic functional group will combine with a nucleophilic functional group prior to inactivation by hydrolysis. Yet another method to control crosslink density is by adjusting the stoichiometry of nucleophilic functional groups to electrophilic functional groups. A one to one ratio leads to the highest crosslink density.

Natural polymers, for example proteins or glycosaminoglycans, e.g., collagen, fibrinogen, albumin, and fibrin, may be crosslinked using reactive precursor species with electrophilic functional groups. Natural polymers are proteolytically degraded by proteases present in the body. Synthetic polymers and reactive precursor species are preferred, however, and may have electrophilic functional groups that are carbodiimidazole, sulfonyl chloride, chlorocarbonates, n-hydroxysuccinimidyl ester, succinimidyl ester or sulfasuccinimidyl esters. The term synthetic means a molecule that is not found in nature, e.g., polyethylene glycol. The nucleophilic functional groups may be, for example, amine, hydroxyl, carboxyl, and thiol. The polymers may also have a polyalkylene glycol portion, including polyethylene glycol. The polymers may also have a hydrolytically biodegradable portion or linkage, for example an ester, carbonate, or an amide linkage. Several such linkages are well known in the art and originate from alpha-hydroxy acids, their cyclic dimmers, or other chemical species used to synthesize biodegradable articles, such as, glycolide, dl-lactide, 1-lactide, caprolactone, dioxanone, trimethylene carbonate or a copolymer thereof. Another embodiment has reactive precursor species with two to ten nucleophilic functional groups each and reactive precursor species with two to ten electrophilic functional groups each. The hydrophilic species may be synthetic molecules.

An embodiment uses biocompatible crosslinked polymers formed from the reaction of precursors having electrophilic functional group and nucleophilic functional groups. The precursors are may be water soluble, non-toxic and biologically acceptable. Preferably, at least one of the precursors is a small molecule of about 2000 Da or less, or 1000 Da or about less, and may be referred to as a "crosslinker". The crosslinker preferably has a solubility of at least 1 g/100 mL in an aqueous solution. A crosslinked molecule may be crosslinked via an ionic or covalent bond, a physical force, or other attraction. At least one of the other precursors may be a macromolecule, and may be referred to as a "functional polymer". The macromolecule, when reacted in combination with a crosslinker, is preferably at least five to fifty times greater in molecular weight than the small molecule crosslinker and is preferably less than about 60,000 Da. Another range is a macromolecule that is seven to thirty times greater in molecular weight than the crosslinker and another range is about ten to twenty times difference in weight. Further, without being limited to a particular range, a macromolecular molecular weight of 5,000 to 50,000 is suitable, a molecular weight of 7,000 to 40,000 is also suitable and a molecular weight of 10,000 to 20,000 is also suitable. The term polymer, as used herein, means a molecule formed of at least three repeating groups. The term "reactive precursor species" means a polymer, functional polymer, macromolecule, small molecule, or crosslinker that can take part in a reaction to form a network of crosslinked molecules, e.g., a hydrogel.

Preparation of Biodegradable Crosslinked Proteins

The biodegradable crosslinkers described in FIGS. 1 and 3 may be reacted with proteins, such as albumin, other serum proteins, or serum concentrates to generate crosslinked polymeric networks. Briefly, aqueous solutions of the crosslinkers described in FIG. 1 and FIG. 3 (at a concentration of 50 to 300 mg/ml) are mixed with concentrated solutions of albumin (600 mg/ml) to produce a crosslinked hydrogel. This reaction can be accelerated if a buffering agent, e.g., borate buffer or triethanol amine, is added during the crosslinking step.

The resultant crosslinked hydrogel is a semisynthetic hydrogel whose degradation depends on the degradable segment in the crosslinker as well as degradation of albumin by enzymes. In the absence of any degradable enzymes, the crosslinked polymer will degrade solely by the hydrolysis of the biodegradable segment. If polyglycolate is used as the biodegradable segment, the crosslinked polymer will degrade in 1-30 days depending on the crosslinking density of the network. Similarly, a polycaprolactone based crosslinked network will degrade in 1-8 months. The degradation time generally varies according to the type of degradable segment used, in the following order: polyglycolate<polylactate<polytrimethylene carbonate<polycaprolactone. Thus it is possible to construct a hydrogel with a desired degradation profile, from a few days to months, using a proper degradable segment.

The hydrophobicity generated by biodegradable blocks such as oligohydroxy acid blocks or the hydrophobicity of PPO blocks in PLURONIC or TETRONIC polymers are helpful in dissolving small organic drug molecules. Other properties which will be affected by incorporation of biodegradable or hydrophobic blocks are: water absorption, mechanical properties and thermosensitivity.

Methods of Using Biocompatible Polymers

The biocompatible crosslinked polymers and their precursors described above may be used in a variety of applications, such as components of tissue adhesives, tissue sealants, drug delivery vehicles, wound covering agents, barriers in preventing postoperative adhesions, and others. These and other suitable applications are reviewed in Schlag and Redl, "Fibrin Sealant" in Operative Surgery, volumes 1-7 (1986), which is hereby incorporated herein by reference to the extent it does not contradict what is explicitly disclosed.

In Situ Formation

Some of these approaches allow for the polymers to be added to the patient "in situ" in a solution and then chemically reacted inside the patient so that the polymers form covalent crosslinks to create a polymer network. The in situ approach lets the polymer be formed in a way that closely conforms to the shape of the tissues in the body, as described, for example, in U.S. Pat. Nos. 5,410,016; 5,573,934 and 5,626,863.

In many applications, the biocompatible crosslinked polymers typically will be formed "in situ" at a surgical site in the body. The various methodologies and devices for performing "in situ" gelation, developed for other adhesive or sealant systems such fibrin glue or sealant applications, may generally be suitably used with the biocompatible crosslinked polymers. Thus, in one embodiment, an aqueous solution of a freshly prepared crosslinker (e.g., SNHS-terminated oligolactide synthesized from a glycerol core in phosphate buffered saline ("PBS") at pH 5 to 7.2) and a functional polymer (e.g., albumin or amine terminated tetrafunctional polyethylene glycol at pH 10 in sodium borate) are applied and mixed on the tissue using a double barrel syringe (one syringe for each solution). The two solutions may be applied simultaneously or sequentially. In some embodiments, it is preferred to apply the precursor solutions sequentially so as to "prime" the tissue, resulting in improved adherence of the biocompatible crosslinked polymer to the tissue. Where the tissue is primed, the crosslinker precursor is preferably applied to the tissue first, followed by the functional polymer solution.

The in situ formation process may be used to make, for example, coatings, adhesion prevention barriers, tissue glues, matrices for drug delivery, wound dressings, implants, and tissue engineering matrices. One may use specialized devices to apply the precursor solutions, including those described in U.S. Pat. Nos. 4,874,368; 4,631,055; 4,735,616; 4,359,049; 4,978,336; 5,116,315; 4,902,281; 4,932,942; Published Patent Cooperation Treaty Patent Application No. WO 91/09641; and R. A. Tange, "Fibrin Sealant" in Operative Medicine: Otolaryngology, volume 1 (1986), the disclosures of which are hereby incorporated herein by reference to the extent they do not contradict what is explicitly disclosed.

Tissue glues may be formed by using precursors that result in the formation of adhesive hydrogels, as described elsewhere herein. As set forth herein, devices such as dual lumen syringes may be used to deliver precursors that form a crosslinked matrix in situ. The matrix acts as a binding agent that functions as a glue or adhesive. Many aspects relating to the tissue glue arts are known, as set forth in, for example, U.S. Pat. Nos. 6,187,347; 6,310,036; 6,121,422; 5,804,428; 5,381,524; 4,973,466; 4,631,055; 4,377,572; and will be evident after reading this application. One aspect of the tissue glue is that most applications require that the glue be readily degradable so that the patients may experience a full recovery after use of the glue.

Wound dressings include coatings, dressings, gels, bandages, and barriers formed in situ or ex vivo for hemostasis, wound healing, drug delivery, prevention of infection, and treating injuries that have damaged the skin. Certain embodiments of the wound dressing agents are readily degradable. Wound dressings may be made using hydrogels as set forth herein, including in situ or ex vivo formation. Certain aspects of wound dressings are set forth in, for example, U.S. patent application Nos. 6,413,539; 6,270,793; 6,096,727; 5,834,007; 5,679,371; 5,604,200; 5,395,305; 4,938,763; 4,570,629; 4,141,973; and 4,060,081.

Implants include matrices, e.g., non-degradable, or those that are readily degradable in vivo via biodegradable linkages, e.g., that are isolated hydrolytically degradable esters. Implants may be formed as needed, e.g., to deliver a drug or other agents, to serve as a barrier, a coating, or a bulking agent.

Tissue engineering matrices are three dimensional matrices that are implantable or formable within the body and allow for cell ingrowth into the matrix. Certain embodiments are tissue engineering matrices that are readily degradable in vivo, with the matrices comprising biodegradable linkages that are isolated hydrolytically degradable esters. As the cells invade the matrix, the matrix slowly degrades so that the cells may populate the matrix and organize into tissues. Certain aspects of tissue engineering matrices are set forth in, for example, U.S. Pat. Nos. 6,471,993; 6,103,255; 6,093,792 6,022,743; and 5,399,665.

Drug Delivery

The subject crosslinkers, functional polymer and their reaction products, the crosslinked materials advantageously may be used for localized drug therapy. Biologically active agents or drug compounds that may be added and delivered from the crosslinked polymer or gel include: proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides. To prepare such crosslinked composition, the bioactive compounds described above are mixed with the crosslinkable polymer prior to making the aqueous solution or during the aseptic manufacturing of the functional polymer. This mixture then is mixed with the crosslinker to produce a crosslinked material in which the biologically active substance is entrapped. Functional polymers made from inert polymers like PLURONIC, TETRONICS or Tween surfactants are preferred in releasing small molecule hydrophobic drugs.

In a preferred embodiment, the active agent or agents are present in a separate phase when crosslinker and crosslinkable polymers are reacted to produce a crosslinked polymer network or gel. This phase separation prevents participation of bioactive substance in the chemical crosslinking reaction such as reaction between NHS ester and amine group. The separate phase also helps to modulate the release kinetics of active agent from the crosslinked material or gel, where 'separate phase' could be oil (oil-in water emulsion), biodegradable vehicle, and the like. Biodegradable vehicles in which the active agent may be present include: encapsulation vehicles, such as microparticles, microspheres, microbeads, micropellets, and the like, where the active agent is encapsulated in a bioerodable or biodegradable polymers such as polymers and copolymers of: poly(anhydride), poly(hydroxy acid)s, poly(lactone)s, poly(trimethylene carbonate), poly(glycolic acid), poly(lactic acid), poly(glycolic acid)-co-poly (glycolic acid), poly(orthocarbonate), poly(caprolactone), crosslinked biodegradable hydrogel networks like fibrin glue or fibrin sealant, caging and entrapping molecules, like cyclodextrin, molecular sieves and the like. Microspheres made from polymers and copolymers of poly(lactone)s and poly (hydroxy acid) are particularly preferred as biodegradable encapsulation vehicles.

In using crosslinked materials which are described herein as drug delivery vehicles, the active agent or encapsulated active agent may be present in solution or suspended form in crosslinker component or functional polymer solution component. The nucleophilic component, whether it be in the crosslinker or the functional polymer is the preferred vehicle due to absence of reactive groups. The functional polymer along with bioactive agent, with or without encapsulating vehicle, is administered to the host along with equivalent amount of crosslinker and aqueous buffers. The chemical reaction between crosslinker and the functional polymer solution readily takes place to form a crosslinked gel and acts as a depot for release of the active agent to the host. Such methods of drug delivery find use in both systemic and local administration of an active agent.

In using the crosslinked composition for drug delivery as mentioned above, the amount of crosslinkable polymer, crosslinker and the dosage agent introduced in the host will necessarily depend upon the particular drug and the condition to be treated. Administration may be by any convenient means such as syringe, canula, trocar, catheter and the like.

Adhesion Prevention Barriers

Several methods for the formation of regional adhesion barriers are described, in which any of a variety of water soluble macromeric precursors are used. The term "macromeric precursor" or "macromer" is meant to connote an oligomeric or polymeric molecule that contains functional groups that enable further crosslinking. Preferably the functionality of a macromer molecule is >2 so that a crosslinked network or hydrogel results upon crosslinking.

In one embodiment, a crosslinked regional barrier is formed in situ, for example, by electrophilic-nucleophilic reaction, free radical polymerization initiated by a redox system or thermal initiation, wherein two components of an initiating system are simultaneously, sequentially or separately instilled in a body cavity to obtain widespread dispersal and coating of all or most visceral organs within that cavity prior to gelation and crosslinking of the regional barrier. Once the barrier is formed, the organs remain isolated from each other for a predetermined period, depending upon the absorption profile of the adhesion barrier material.

Preferably, the barrier is selected to have a low stress at break in tension or torsion, so as to not adversely affect normal physiological function of visceral organs within the region of application. The barrier also may contain a drug or other therapeutic agent.

Controlled Release

Certain embodiments are accomplished by providing compositions and methods to control the release of relatively low molecular weight therapeutic species using hydrogels. In accordance with the principles of certain embodiments, a therapeutic species first is dispersed or dissolved within one or more relatively hydrophobic rate modifying agents to form a mixture. The mixture may be formed into microparticles, which are then entrapped within a bioabsorbable hydrogel matrix so as to release the water soluble therapeutic agents in a controlled fashion. Alternatively, the microparticles may be formed in situ during crosslinking of the hydrogel.

In one method, hydrogel microspheres are formed from polymerizable macromers or monomers by dispersion of a polymerizable phase in a second immiscible phase, wherein the polymerizable phase contains at least one component required to initiate polymerization that leads to crosslinking and the immiscible bulk phase contains another component required to initiate crosslinking, along with a phase transfer agent. Pre-formed microparticles containing the water soluble therapeutic agent may be dispersed in the polymerizable phase, or formed in situ, to form an emulsion. Polymerization and crosslinking of the emulsion and the immiscible phase is initiated in a controlled fashion after dispersal of the polymerizable phase into appropriately sized microspheres, thus entrapping the microparticles in the hydrogel microspheres. Visualization agents may be included, for instance, in the microspheres, microparticles, and/or microdroplets.

Embodiments include compositions and methods for forming composite hydrogel-based matrices and microspheres having entrapped therapeutic compounds. In one embodiment, a bioactive agent is entrapped in microparticles having a hydrophobic nature (herein called "hydrophobic microdomains"), to retard leakage of the entrapped agent. More preferably, the composite materials that have two phase dispersions, where both phases are absorbable, but are not miscible. For example, the continuous phase may be a hydrophilic network (such as a hydrogel, which may or may not be crosslinked) while the dispersed phase may be hydrophobic (such as an oil, fat, fatty acid, wax, fluorocarbon, or other synthetic or natural water immiscible phase, generically referred to herein as an "oil" or "hydrophobic" phase).

The oil phase entraps the drug and provides a barrier to release by slow partitioning of the drug into the hydrogel. The hydrogel phase in turn protects the oil from digestion by enzymes, such as lipases, and from dissolution by naturally occurring lipids and surfactants. The latter are expected to have only limited penetration into the hydrogel, for example, due to hydrophobicity, molecular weight, conformation, diffusion resistance, etc. In the case of a hydrophobic drug which has limited solubility in the hydrogel matrix, the particulate form of the drug may also serve as the release rate modifying agent.

Hydrophobic microdomains, by themselves, may be degraded or quickly cleared when administered in vivo, making it difficult to achieve prolonged release directly using microdroplets or microparticles containing the entrapped agent in vivo. In accordance with certain embodiments, however, the hydrophobic microdomains are sequestered in a gel matrix. The gel matrix protects the hydrophobic microdomains from rapid clearance, but does not impair the ability of the microdroplets or microparticles to release their contents slowly. Visualization agents may be included, for instance, in the gel matrix or the microdomains.

In one embodiment, a microemulsion of a hydrophobic phase and an aqueous solution of a water soluble molecular compound, such as a protein, peptide or other water soluble chemical is prepared. The emulsion is of the "water-in-oil" type (with oil as the continuous phase) as opposed to an "oil-in-water" system (where water is the continuous phase). Other aspects of drug delivery are found in commonly assigned U.S. patent application Ser. Nos. 09/134,287 entitled "Composite Hydrogel Drug Delivery Systems"; 09/390,046 entitled "Methods and Apparatus for Intraluminal Deposition of Hydrogels"; and 09/134,748 entitled "Methods for Forming Regional Tissue Adherent Barriers and Drug Delivery Systems", each of which are hereby incorporated herein by reference to the extent they do not contradict what is explicitly disclosed.

In some embodiments, the hydrogel microspheres are formed having a size that will provide selective deposition of the microspheres, or may linked with ligands that target specific regions or otherwise affect deposition of the microspheres within a patient's body.

Controlled rates of drug delivery also may be obtained in certain embodiments by degradable, covalent attachment of the bioactive molecules to the crosslinked hydrogel network. The nature of the covalent attachment can be controlled to enable control of the release rate from hours to weeks or longer. By using a composite made from linkages with a range of hydrolysis times, a controlled release profile may be extended for longer durations.

Composite Biomaterials

The biocompatible crosslinked polymers of certain embodiments optionally may be reinforced with flexible or rigid fibers, fiber mesh, fiber cloth and the like. The insertion of fibers improves mechanical properties like flexibility, strength, and tear resistance. In implantable medical applications, biodegradable fibers, cloth, or sheets made from oxidized cellulose or poly(hydroxy acid)s polymers like polylactic acid or polyglycolic acid, are preferred. Such reinforced structures may be produced using any convenient protocol known in the art.

In a preferred method, aqueous solutions of functional polymers and crosslinkers are mixed in appropriate buffers and proportions are added to a fiber cloth or net such as Interceed (Ethicon Inc., New Brunswick, N.J.). The liquid mixture flows into the interstices of the cloth and becomes crosslinked to produce a composite hydrogel. Care is taken to ensure that the fibers or fiber mesh are buried completely inside the crosslinked hydrogel material. The composite structure can be washed to remove side products such as N-hydroxysuccinimide. The fibers used are preferably hydrophilic in nature to ensure complete wetting of the fibers by the aqueous gelling composition.

EXAMPLES

The following non-limiting examples are intended to illustrate the synthesis of new biocompatible crosslinked polymers and their precursors, and their use in making several medical products. Those skilled in the art will appreciate that modifications can be made to these examples, drawings, illustrations and claims that are intended to fall within the scope of the present invention.

Materials and Equipment

Polyethylene glycol was purchased from various sources such as Shearwater Polymers, Union Carbide, Fluka and Polysciences. Multifunctional hydroxyl and amine terminated polyethylene glycol were purchased from Shearwater Polymers, Dow Chemicals and Texaco. PLURONIC and TETRONIC series polyols were purchased from BASF Corporation. DL-lactide, glycolide, caprolactone and trimethylene carbonate was obtained from commercial sources like Purac, DuPont, Polysciences, Aldrich, Fluka, Medisorb, Wako and Boehringer Ingelheim. N-hydroxysulfosuccinimide was purchased from Pierce. All other reagents, solvents were of reagent grade and were purchased from commercial sources such as Polysciences, Fluka, Aldrich and Sigma. Most of the reagents and solvents were purified and dried using standard laboratory procedures such as described in D. D. Perrin et al., Purification of Laboratory Chemicals (Pergamon Press 1980).

General Analysis

The polymers synthesized according to these examples were chemically analyzed using structure-determining methods such as nuclear (proton and carbon-13) magnetic resonance spectroscopy, infrared spectroscopy. Molecular weights were determined using high pressure liquid chromatography and gel permeation chromatography. Thermal characterization of the polymers, including melting point and glass transition temperatures, were performed using differential scanning calorimetric analysis. Aqueous solution properties such as micelle and gel formation was determined using fluorescence spectroscopy, UV-visible spectroscopy and laser light scattering instruments.

In vitro degradation of the polymers was followed gravimetrically at 37° C., in an aqueous buffered medium such as phosphate buffered saline (at pH 7.2). In vivo biocompatibility and degradation life times was assessed by injecting or forming a gelling formulation directly into the peritoneal cavity of a rat or rabbit and observing its degradation over a period of 2 days to 12 months.

Alternatively, the degradation was also assessed by prefabricating a sterile implant, made by a process like solution casting, then surgically implanting the implant within an animal body. The degradation of the implant over time was monitored gravimetrically or by chemical analysis. The biocompatibility of the implant was assessed by standard histological techniques.

Some aspects of methods and procedures for certain embodiments are set forth herein are provided and set forth in detail in commonly owned U.S. Pat. No. 7,009,034, which is hereby incorporated herein by reference to the extent it does not contradict what is explicitly disclosed. Some of these methods and procedures are the synthesis of a water-soluble difunctional, biodegradable functional polymer based on polyalkylene oxide block copolymer, synthesis of amine terminated synthetic biodegradable crosslinkable polymers, synthesis of carboxyl terminated oligolactic acid polymer activated with N-hydroxysulfosuccinimide, preparation of polyethylene glycol based tetrafunctional crosslinker, synthesis of sulfonyl chloride activated crosslinkers, synthesis of multifunctional oligopolycaprolactone, preparation of polyethylene glycol-co-polytrimethylene carbonate copolymer terminated with N-hydroxysuccinimide, synthesis of succinated polyhydroxy compounds activated with N-hydroxysulfosuccinimide ES, preparation of composite synthetic crosslinked colored biodegradable gels, evaluation of the stability of colorants in solution, concentrations of coloring agent for use in an in situ crosslinked hydrogel coating, the effect of coloring agents on gelation times.

Example 1

Preparation of Synthetic Crosslinked Biodegradable Gels 1.57 g (0.8 mM) of 4 arm amine terminated polyethylene glycol molecular weight 2000 was dissolved in 10 ml 0.1 M sodium borate buffer at pH 9.5 2 g of 4 arm succinimidyl ester activated polymer (4PEG2KGS, molecular weight 2500) was dissolved in phosphate buffered saline. These two solutions were mixed to produce a crosslinked gel. In another variation of this method, the 4PEG2KGS polymer solid was directly added to the amine terminated polymer solution to produce a crosslinked polymer.

In another variation, a crosslinker consisting of an equimolar solution of dilysine can be used in place of the 4 arm PEG amine solution to form a hydrogel. Gelation was seen to occur within 10 seconds of mixing the two solutions. The amine terminated polymer solution described above was added with 0.1% of F D and C blue or indigo dye prior to crosslinking reaction. The addition of dye allows the preparation of colored gels.

Example 2

Formulation of SG-PEG with Di-Lysine

A four arm PEG with succinimidyl glutarate (SG) end groups (Shearwater Polymers, approx. 9,100 g/mol, 0.704 grams, $6.5 \times 10^{-5}$ moles) was dissolved in 2.96 g 0.01M pH 4.0 phosphate buffer (19.2% solids). Di-lysine (Sigma, 347.3 g/mol, 0.03 grams, $8.7 \times 10^{-5}$ moles) was dissolved in 3.64 grams of 0.1M pH 9.5 borate buffer (0.8% solids). On combination of the two solutions, a hydrogel formed having a percent solids of 10%. The di-lysine has 3 amine groups. The SG-PEG has 4 NHS groups. After correction for the less than 100% degree of substitution on the SG-PEG, the formulation gives a 1:1 stoichiometry of amine groups to NHS groups.

Example 3

Formulation of SG-PEG with Tri-Lysine

A four arm PEG with SG end groups (Shearwater Polymers, approx. 9,100 g/mol, 0.675 grams, $6.2 \times 10^{-5}$ moles) was dissolved in 2.82 g 0.01M pH 4.0 phosphate buffer (19.3% solids). Tri-lysine (Sigma, 402.5 g/mol, 0.025 grams, $6.2 \times 10^{-5}$ moles) was dissolved in 3.47 grams of 0.1M pH 9.5 borate buffer (0.7% solids). On combination of the two solutions, a hydrogel formed having a percent solids of 10%. The tri-lysine has 4 amine groups. The SG-PEG has 4 NHS groups. After correction for the less than 100% degree of substitution on the SG-PEG, the formulation gives a 1:1 stoichiometry of amine groups to NHS groups.

Example 4

Formulation of SG-PEG with Tetra-Lysine

A four arm PEG with SG end groups (Shearwater Polymers, approx. 9,100 g/mol, 0.640 grams, $5.9 \times 10^{-5}$ moles, also referred to herein as being about 10,000 MW) was dissolved in 2.68 g 0.01M pH 4.0 phosphate buffer (19.2% solids). Tetra-lysine (Sigma, 530.7 g/mol, 0.025 grams, $4.7 \times 10^{-1}$ moles) was dissolved in 3.30 grams of 0.1M pH 9.5 borate buffer (0.8% solids). On combination of the two solutions, a hydrogel formed having a percent solids of 10%. The tetra-lysine has 5 amine groups. The SG-PEG has 4 NHS groups. After correction for the less than 100% degree of substitution on the SG-PEG, the formulation gives a 1:1 stoichiometry of amine groups to NHS groups.

Example 5

Gel Time Measurement

The amine solution (100 μL) was aliquotted into a 100×13 test tube. A flea-stirbar (7×2 mm, Fisher Scientific p/n 58948-976) was placed in the test tube. The test tube was held stationary over a digital magnetic stirrer (VWR Series 400S Stirrer) set at 300 rpm. A 1 cc tuberculin syringe (Becton Dickinson, p/n BD309602) was filled with 100 μL of the ester solution. The syringe was inserted up to the flanges so that the distal end was just over the amine solution. Simultaneously the plunger was depressed and a stop watch started. When the solution solidifies sufficiently so that the stir bar stops spinning, the stop watch was stopped. Each solution was measured in triplicate and the mean ±1 standard deviation was plotted. Results for the formulations of examples 2, 3 and 4 are shown in FIG. 7.

Example 6

Change in Gel Time as a Function of Ester Solution Age

Figure 8:
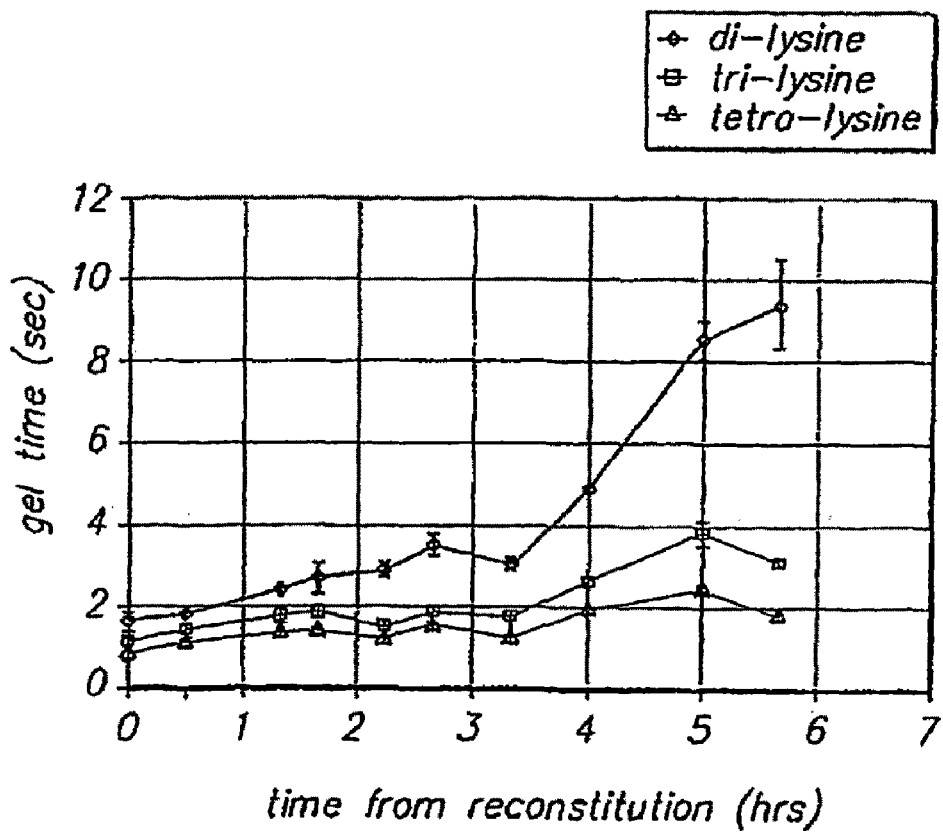
FIG. 8 shows variation in gelation time with the solution age of the electrophilic functional polymers of Examples 2-4, see also Example 6.

An important characteristic of these systems is the loss in reactivity over time from reconstitution of the ester solution, also referred to as the ester's pot life. This loss in reactivity occurs due to hydrolysis of the N-hydroxysuccinimidyl ester, before the activated molecule can combine with its respective nucleophilic functional group. The loss of reactivity was characterized by measuring the change in gel time as a function of time from reconstitution of the NHS ester solution. The gel time was measured periodically. The NHS ester solution was stored at ambient conditions during this measurement. Results for the solutions described in Examples 2, 3 and 4 are shown in FIG. 8.

Example 7

Gel Formation at Different Percent Solids from 4 arm CM-HBA-NHS PEG and Lys-Lys

Using the gel time method described in Example 5, five different gel compositions were made using 4 arm PEG (CM-HBA-NHS, see FIG. 19, about 10,000 MW) (Shearwater Polymers) and di-lysine (Sigma). The formulations are listed below in Table 3.

TABLE 3

| Conc. (%) | CM-HBA-NHS (g) | Phosphate (g) | Lys-Lys (g) | Borate (g) |
|---|---|---|---|---|
| 8.5 | 0.2469 | 1.264 | 0.01 | 1.5012 |
| 10 | 0.2904 | 1.2209 | 0.012 | 1.4994 |
| 12.5 | 0.363 | 1.1483 | 0.015 | 1.4964 |
| 15 | 0.4356 | 1.0757 | 0.018 | 1.4936 |
| 20 | 0.5808 | 0.9305 | 0.024 | 1.4876 |

Figure 9:
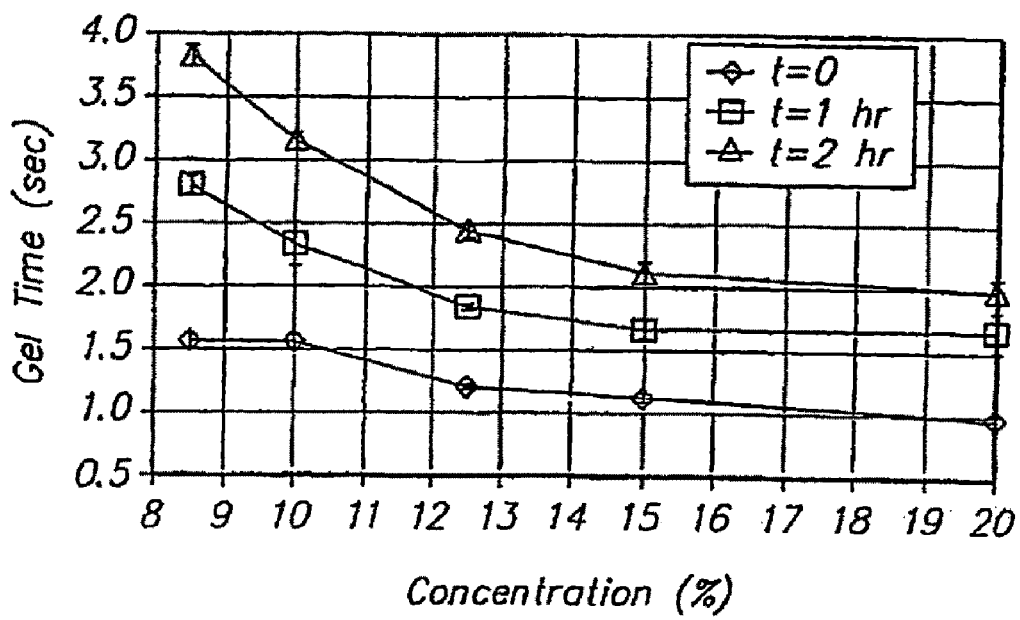
FIG. 9 shows the variation in gelation time with the concentration of biocompatible crosslinked polymer precursors, and with the solution age of the 4 arm 10 kDa carboxymethyl-hydroxybutyrate-N-hydroxysuccinimidyl PEG ("CM-HBA-NHS") electrophilic functional polymer of Example 7.

The formulations were adjusted to give a 1 to 1 ratio of electrophilic functional end groups on the CM-HBA-NHS to nucleophilic reactive groups on the di-lysine ("Lys-Lys") (3). The CM-HBA-NHS quantities were dissolved in 0.01M pH 5.0 phosphate buffer. The di-lysine was dissolved in 0.1M pH 11 borate buffer. Gel time results are shown in FIG. 9. This data also shows that the higher percent solids solutions also are the most stable with respect to retention of speed of reaction.

Example 8

Degradation of Hydrogels

Figure 10:
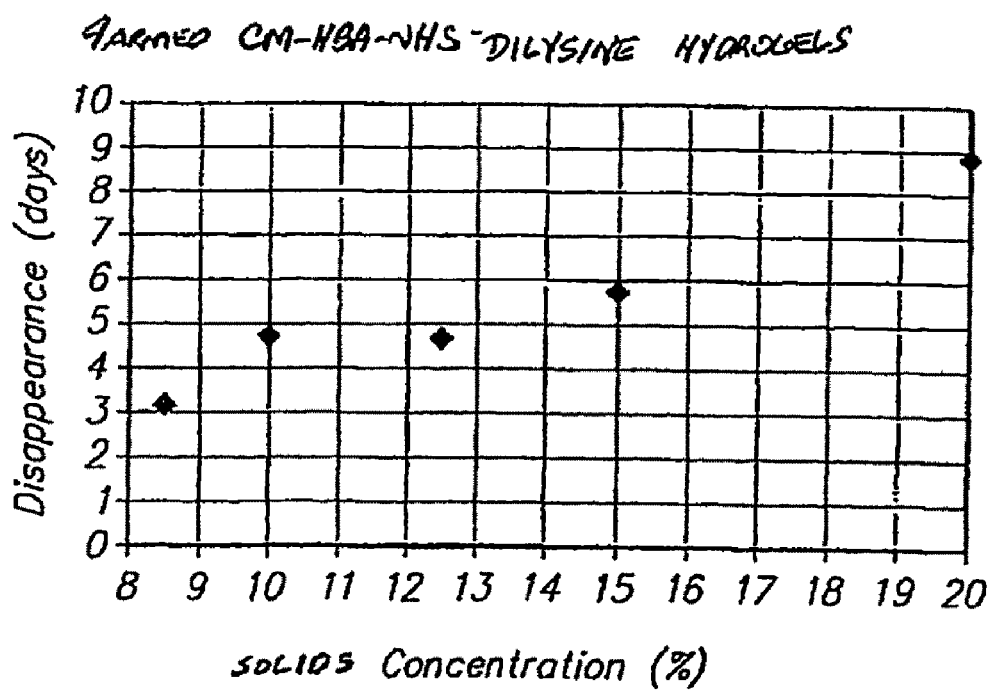
FIG. 10 shows variation in degradation time with concentration for the biocompatible crosslinked polymer of Example 8.
Figure 12:
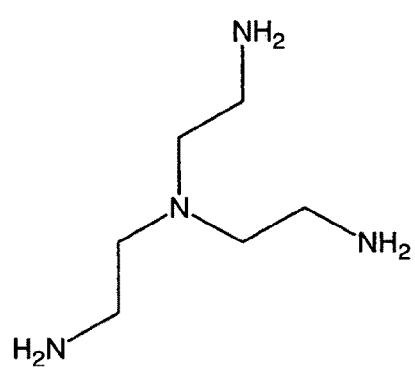
FIG. 12 depicts the chemical structure of Tris.
Figure 11:
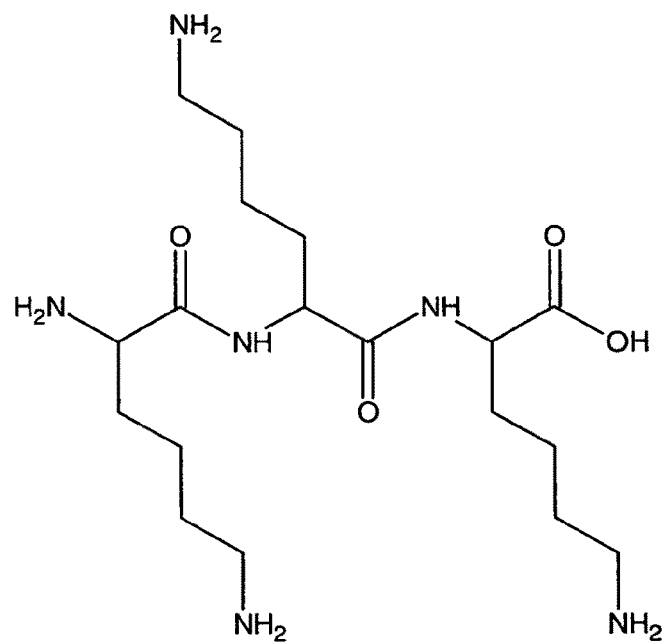
FIG. 11 depicts the chemical structure of trilysine (LLL).

Hydrogel plugs made as per Example 7 were placed in approximately 25 mL 0.1 M phosphate buffered saline at pH 7.4 in 50 mL Falcon tubes and placed in a constant temperature bath at 37° C. The hydrogel plugs were observed visually at periodic intervals and the time of gel disappearance noted. The data are plotted in FIG. 10.

Example 9

Precursor Spray Procedure to Form a 7.5% Solids Hydrogel from 4 Arm SG and Dilysine An ethylene oxide sterilized air assisted sprayer was used in conjunction with aqueous solutions of polymerizable monomers. Solution 1 consisted of a 14.4% solution of 4 arm PEG succinimidyl glutarate (SG-PEG, MW 10,000 purchased from Shearwater Polymers) dissolved in 0.01M phosphate buffer at pH 4.0 and was sterile filtered (Pall Gelman syringe filter, p/n 4905) and drawn up in a sterile 5 cc syringe. Solution 2 consisted of a 1.2% solution of a dilysine (purchased from Sigma Chemicals) dissolved in 0.1 M borate buffer at pH 11 with 0.5 mg/mL methylene blue for visualization and was also sterile filtered and drawn up in a sterile 5 cc syringe. These solutions, when combined 1:1 on a volumetric basis, resulted in a 1:1 ratio of NHS ester to amine end group. The final % solids after combination was 7.5%. The two syringes were individually loaded in the two separate receptacles through a LUER-LOK type of linkage. Airflow from a regulated source of compressed air (an air compressor such as those commercially available for airbrushes) was connected to the device using a piece of TYGON tube. On compressing the syringe plungers a steady spray of the two liquid components was observed. When this spray was directed to a piece of tissue (rat cecum) a hydrogel coating was observed to form on the surface of the tissue. This hydrogel coating was rinsed with saline (the hydrogel coating is resistant to rinsing) and was observed to be well adherent to the tissue surface. Within a short period of time (less than a minute) an area of 10 cm×5 cm could be coated with ease.

Example 10

Precursor Spray Procedure to Form a 12.5% Solids Hydrogel from 4 Arm CM-HBA-NHS and Dilysine A hydrogel barrier film made from 4 arm CM-HBA NS (MW 10,000 purchased from Shearwater Polymers), and dilysine was similarly prepared and sprayed as described in Example 9. In the present example the 4 arm CM-HBA-NHS solution was made up to 24.0% solids and the dilysine solution was made up to 1.0% solids such that on combination in an equal volume delivery system a 1:1 ratio of NHS to amine end groups results, giving a final % solids of 12.5%. This formulation was effective for making a hydrogel.

Example 11

Spray Application of Crosslinker and Polymer to Form Crosslinked Film

Two solutions (component A and component B) were prepared. Component A consisted of dilysine in 0.1M borate buffer, pH 9.5. Component B consisted of either 4 arm SG-PEG (FIG. 20) or 4 arm CM-HBA-NHS (FIG. 19) in 0.01M phosphate buffer, pH 4.0. These solutions were prepared such that the amine to ester stoichiometric ratio was 1:1 and the final total solution concentration was 7.5% or 12.5%, respectively.

A FIBRIJECT (Micromedics, Inc.) 5 cc syringe holder and cap was used, preloaded with 5 cc of each solution and attached to a dual barrel atomizing sprayer. The sprayer has two hubs for the syringes to connect to allowing the two fluids to be advanced through two separate lumens over any preset distance. A third hub exists for the application of the atomizing gas. Air was used in this example. The distal tip of the sprayer contains a chamber where the gas expands out of an introduction tube, then flows past the two polymer solution nozzles in an annular space around each. The gas is accelerated in the annular spaces using a flow rate suitable for the complete atomization of the two fluid streams (~2L/min.). Two overlapping spray cones are thus formed allowing for well mixed, thin, uniform coatings to be applied to surfaces, and such coatings resulted from mixtures of A and B.

Example 12

Adhesion Prevention in Rat Cecum Model

Surgical procedure Male Sprague Dawley rats (250-300 grams were anesthetized with an intramuscular 4 ml/kg "cocktail" of Ketamine (25 mg/ml), Xylazine (1.3 mg/mL) and Acepromazine (0.33 mg/mL). The abdominal area was shaved and prepped for aseptic surgery. A midline incision was made to expose the abdominal contents. The cecum was identified and location within the abdomen was noted. The cecum was pulled out of the abdomen and the surface of one side was abraded using dry sterile gauze. A technique of abrading one area by stroking the surface 12 times with the gauze was used. The cecal arterial supply was interrupted using bipolar coagulation along the entire surface area of the damaged cecum.

The opposing abdominal sidewall which lays in proximity to the damaged cecal surface was deperitonealized with a scalpel blade and the underlying muscle layer was scraped to the point of hemorrhaging.

Figure 19:
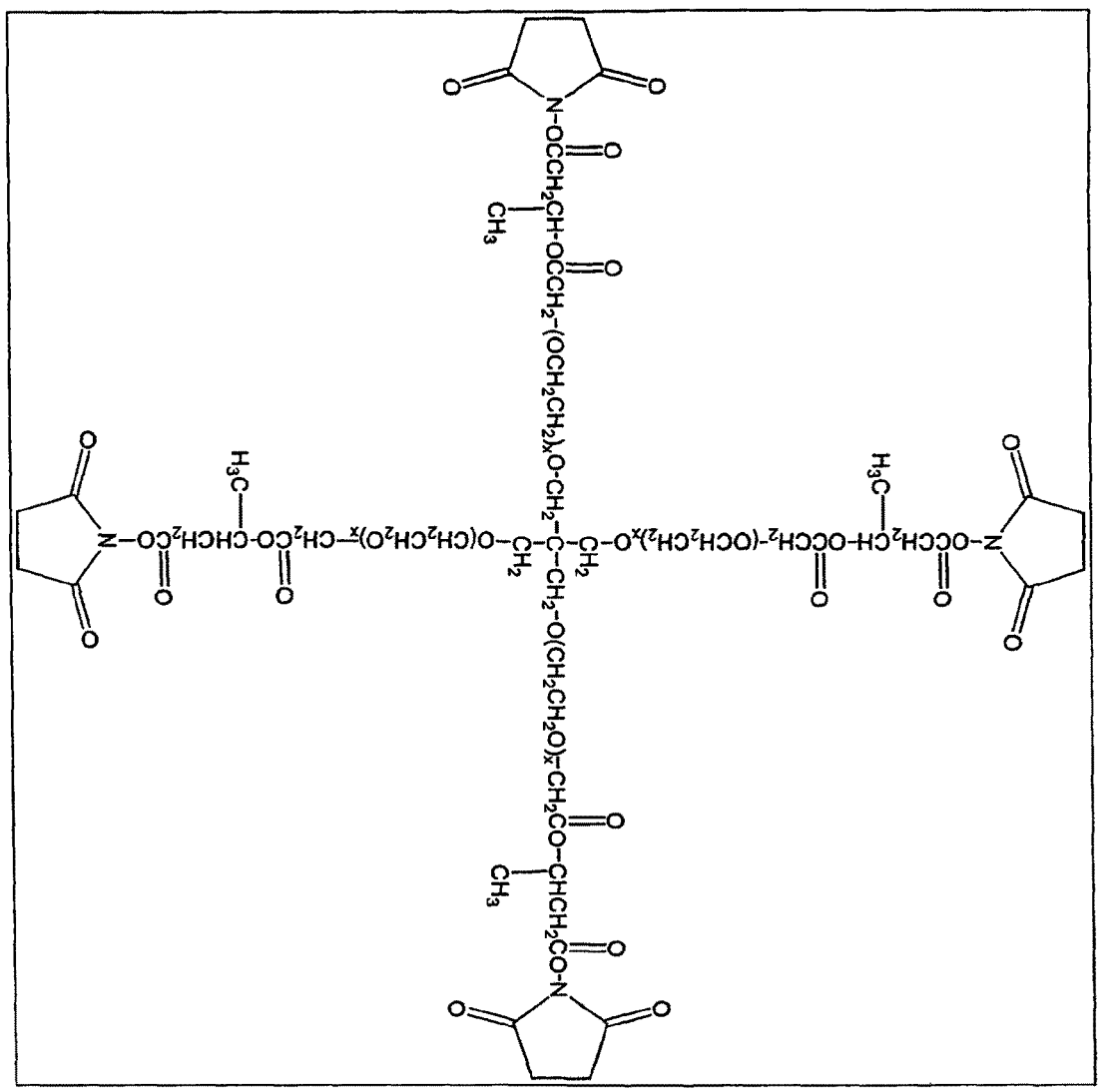
FIG. 19 depicts a four-armed CM-HBA-NHS, an electrophile made with polyethylene glycol and NHS esters.
Figure 20:
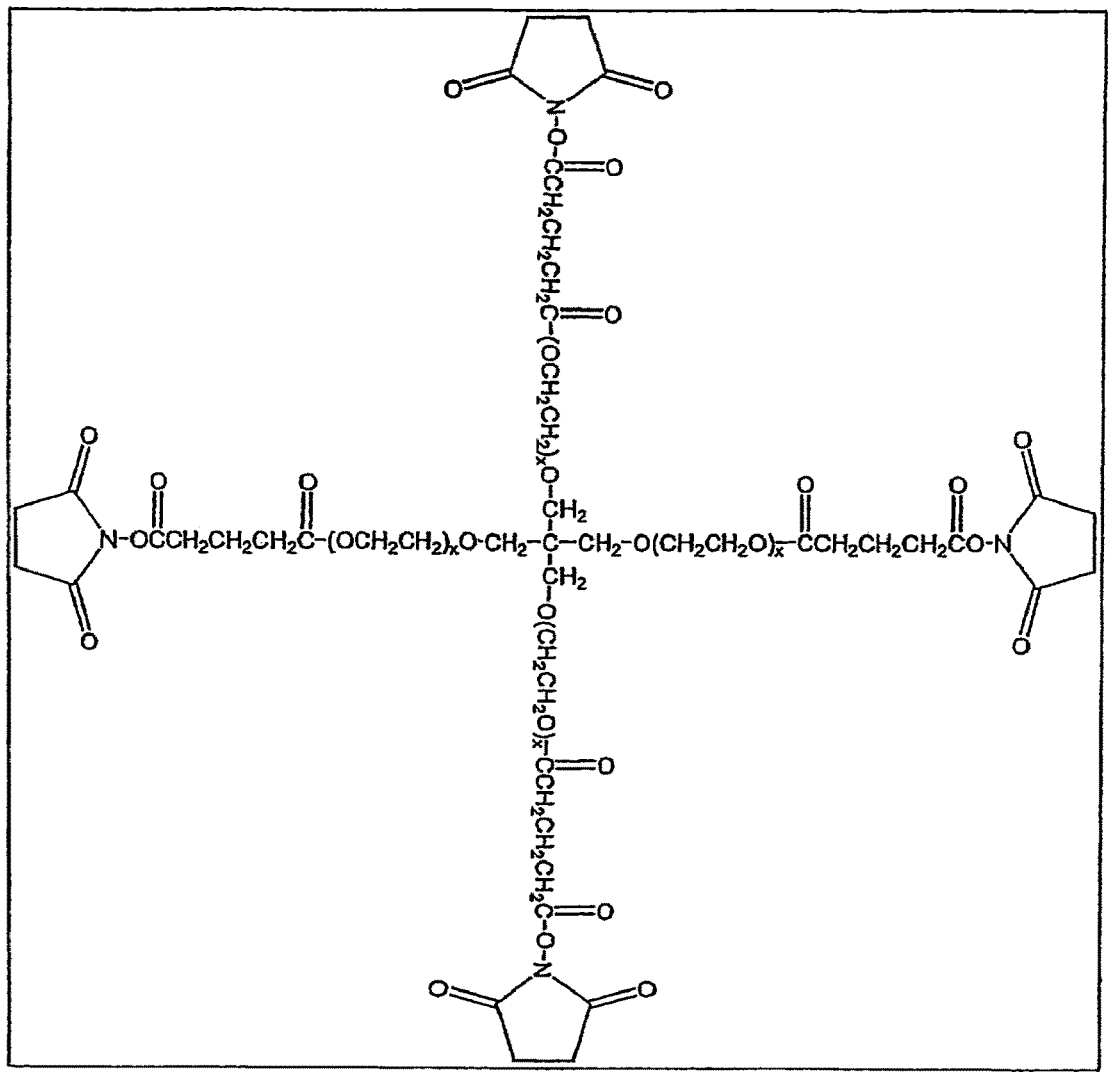
FIG. 20 depicts 4a PEG-SG-NHS, a four armed succinimidyl glutarate made with polyethylene glycol and NHS.

The cecum was sprayed with either the SG-PEG system or the CM-HBA-NHS system using the air assisted spray method described in the preceding example. The cecum was placed with the damaged (ischemic area) side up opposite the damaged side wall. Active bleeding was controlled before closing. The peritoneum and muscle wall was closed with 3-0 nylon and the skin was closed with 4-0 silk. Rats were returned to their cages for one to two weeks at which time evaluation of the adhesion between the side wall and cecum was noted. The rats were killed at 10 days and the tenacity and extent of adhesion was evaluated. The results are summarized in Table 4, with 4a SG standing for SG-PEG as shown in FIG. 20, MB standing for methylene blue, and 4a CM standing for CM-HBA-NHS as shown in FIG. 19.

TABLE 4

| Rat # | Material Applied | Reference Example | Finding on Day 10 |
|---|---|---|---|
| 403 | 7.5% 4aSG with Lys-Lys w/MB | Example 9 | Small amount of gel present on cecum. No adhesions from cecum to sidewall. No gel on sidewall |
| 404 | 7.5% 4aSG with Lys-Lys w/MB | Example 9 | Some mesentery stuck to cecum. No gel. No adhesions. |
| 405 | 7.5% 4aSG with Lys-Lys w/MB | Example 9 | Small amount of gel present on cecum. Some mesentery stuck to cecum and sidewall. Some gel between mesentery and cecum where stuck. No adhesions. |
| 406 | 12.5% 4aCM with Lys-Lys w/MB | Example 10 | No gel present. No adhesions. |
| 407 | 12.5% 4aCM with Lys-Lys w/MB | Example 10 | No gel on cecum or sidewall. No adhesions. |
| 408 | 12.5% 4aCM with Lys-Lys w/MB | Example 10 | Rat died post-op (anesthesia overdose). |

Example 13

Control of Degradation Time of Hydrogels Using Mixtures of Low Molecular Weight Molecules of Trilysine and Tris(2-Aminoethyl)Amine(Tris)

This example shows that the swelling, gelation time, and degradation time of a hydrogel is controllable by incorporating various amounts, types, and combinations of low molecular weight amines in the hydrogel. The low molecular weight precursors were nucleophiles of trilysine (Bachem, see FIG. 11) or Tris (Aldrich, see FIG. 12) that were reacted with a 4-armed PEG-SG-NHS with MW of about 20,000 (FIG. 20). Gel time, swelling, and degradation of the hydrogels were measured as a function of the relative amounts of Tris and trilysine. All hydrogel formulations were made with 9.1% solids, in pH 9.5 buffers with a 1 to 1 ratio of nucleophiles to electrophiles. The mixing was accomplished by connecting syringes loaded with the precursor solutions to a mixing tip (ASHBY-CROSS, STATOMIX) that quickly and thoroughly mixed the solutions.

FIGS. 13, 14, 15, 16 show the results of gelation time, swelling, degradation, and mechanical properties tests, respectively. Increased amounts of Tris relative to the amount of trilysine unexpectedly accelerated gelation, increased swelling, and accelerated degradation rates. Significantly, these trends were approximately linear so that the ratio of nucleophiles could be predicted and chosen to achieve a desired hydrogel property, e.g., a desired degradation rate. Gelation measurements were performed by the methods of Example 5.

Swelling measurements were performed by forming gels of a defined geometry and measuring their weight as a function of time immersed in 37° C. phosphate buffered saline (PBS). Weight measurements were performed by weighing the samples before immersion or by removing immersed samples from the PBS, blotting them with a dry towel, and weighing them. The % swelling was defined as ((final weight−initial weight)/initial weight*100.

The degradation tests were performed by forming gel plugs in a 3 cc syringe, forcing them out of the plunger-end of the syringe with PBS forced through the syringe tip, and placing the plugs in 50 ml centrifuge tubes filled with 20 ml PBS and stored at 37° C. and monitored until they were no longer visible to the human eye, a test also referred to herein as measuring the disappearance time of the gels.

Example 14

Degradation of Hydrogels Made from Trilysine

This example evaluated the persistence time of a hydrogel made from a four armed 20,000 MW PEG-SG-NHS precursor and a trilysine precursor as described in Example 13. The precursors were mixed and gelled in a 3 cc capacity plastic syringe, pushed out of the syringe, and divided into four pieces weighing about 0.25 g each. Two parts were inserted subcutaneously in pockets created by blunt dissection in each rat, one on either side of the midline on the back of the rat. One piece was placed in each pocket. The subcutaneous pockets were closed with interrupted sutures, and the animals were allowed to recover. At scheduled timepoints tissue samples were taken from the subcutaneous pocket and fixed in fomalin for histological evaluation according to methods known to those skilled in these arts. At each timepoint, (4 days, 1 week, 2 weeks, 3 weeks, 4 weeks), the subcutaneous pockets were opened and the gel plugs were evaluated using the following scoring system: 4=solid gel; 3=loose, extrudable gel; 2=viscous liquid; 1=no gel. The gels were clear at all timepoints and no infections were noted throughout the study. Results are shown in Table 5. Gels appeared to be present at 35 days; no data was recorded after 35 days.

TABLE 5

Observations of trilysine hydrogels in vivo

| Rat Number | Days after implant | Observations |
|---|---|---|
| 1 | 4 | Score = 4 on both sides. Gels were clear, had no infection |
| 2 | 7 | Score = 4 on both sides. Gels were clear, had no infection |
| 3 | 15 | Score = 4 on both sides. Gels were clear, had no infection |
| 4 | 21 | Score = 4 on both sides. Gels were clear, had no infection |
| 5 | 28 | Score = 3.5 on one side and no gel found on the other side. Gels were clear, had no infection |
| 6 & 7 | 35 | Gels were present as determined by palpitation of the subcutaneous pockets, gels were not removed. |

Example 15

Degradation of Hydrogels Made from Trilysine or Tris

This example evaluated the persistence time of a hydrogel made from four armed 20,000 MW PEG-SG-NHS and trilysine or Tris. To make a hydrogel including trilysine, about 0.8 g of trilysine (Bachem) was added to 19 ml of 0.1 M borate followed by pH adjustment to 10.5. About 0.4 g of the four armed PEG-SG-NHS (Shearwater) was dissolved in 1.65 ml 0.01 M phosphate buffer, pH 4.0 immediately before use to make a solution of about 18% solids. The solutions were mixed in 1:1 proportions, with a final solids concentration in the hydrogel of about 9%. The mixing was accomplished by connecting syringes loaded with the solutions to a mixing tip (ASHBY-CROSS, STATOMIX) that quickly and thoroughly mixed the solutions.

To make a hydrogel including Tris, about 10 ml of 0.14% Tris (Aldrich) was made by adding about 0.014 g of Tris to 10 ml 0.1 M borate, and the pH was adjusted to pH 8.5. About 0.3 g of the SG-NHS (Shearwater) was dissolved immediately before use in 1.7 ml of phosphate buffer, pH 4.0, so that a solids concentration of about 15% was achieved. The solutions were mixed in 1:1 proportions, with a final solids concentration in the hydrogel of about 8%.

Figure 17:
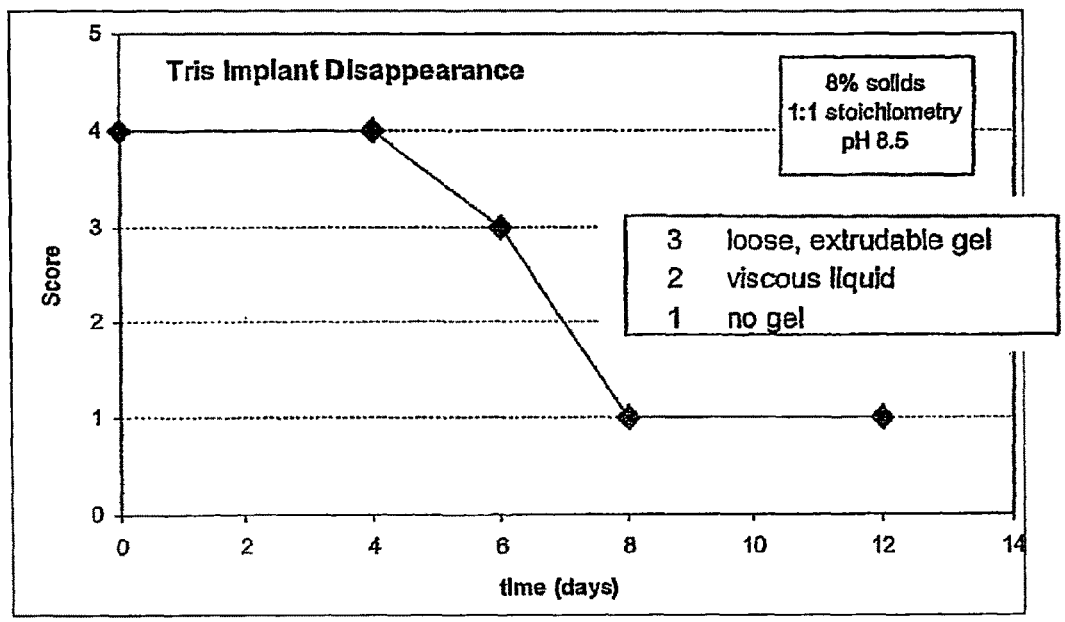
FIG. 17 is a graph of degradation of a Tris-based hydrogel, as is further described in Example 15.
Figure 18:
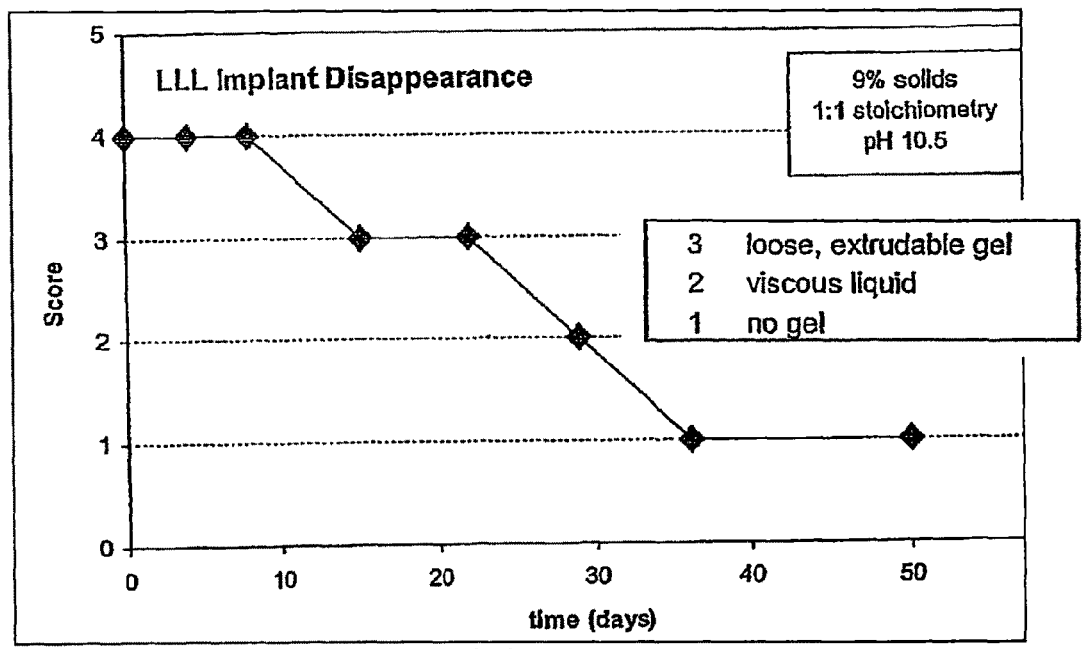
FIG. 18 is a graph of degradation of an LLL-based hydrogel, as is further described in Example 15.

The gels were made in a 3 cc syringe, implanted into rats, and evaluated for degradation as described in Example 14. The results for hydrogels including Tris and trilysine are shown in FIGS. 17 and 18, respectively. The Tris based hydrogels were completely degraded within 4 to 8 days. The trilysine based gels persisted longer. At about 22 days, the trilysine gels were noticeably degraded and at day 29 the gels were liquefied.

Example 16

Degradation and Properties of Dilysine-based Hydrogels

This experiment produced data showing degradation profiles for hydrogels made from dilysine plus a four armed carboxymethyl Hydroxybutyrate N-Hydroxysuccinimidyl polyethylene glycol (CM-HBA-NHS, see FIG. 19, "4aCM") of about 10,000 MW or a 20,000 MW PEG-SG-NHS, see FIG. 20, "4aSG". Formulations of hydrogels made from 4 armed 10,000 MW CM-HBA-NHS and eight armed 20,000 MW PEG amine are plotted as "X" in FIGS. 21 and 22. Gelation time, swelling, and the effect of solids concentrations are also reported, with the tests being performed essentially as described in Example 13.

A nebulizer connected to a sprayer that rapidly combined and thoroughly mixed the component solutions as a spray was used to combine the precursor solutions to create the hydrogels, as described in commonly owned and assigned U.S. Pat. No. 6,165,201. The nucleophilic precursor solution was made by dissolving the nucleophile (e.g., dilysine) in pH 11.0, 0.1 M buffer. The electrophilic precursor solution was made by dissolving the electrophilic precursor (e.g., 10,000 MW CM-HBA-NHS or 20,000 MW PEG-SG-NHS) in about 2.3 ml of 0.05 M phosphate buffer of pH 5.0. The precursor solutions were combined in a 1:1 v/v ratio to achieve the reported solids concentration. The hydrogel was formed on a horizontal Mylar surface, cut into three pie-shaped samples, and their degradation and swelling properties were measured as described in Example 13.

FIGS. 21, 22, and 23 show the degradation rate, gelation time, and swelling, respectively, of hydrogels formed with dilysines. The time for a gel to disappear (a measure of degradability) increased as the solids concentration increased, with the time increasing faster for hydrogels made with PEG-SG-NHS as compared to CM-HBA-NHS, see FIG. 21. The gelation time decreased as the solids concentration increased, see FIG. 22. The swellability of the hydrogels increased as the solids concentration increased, see FIG. 23.

Figure 24:
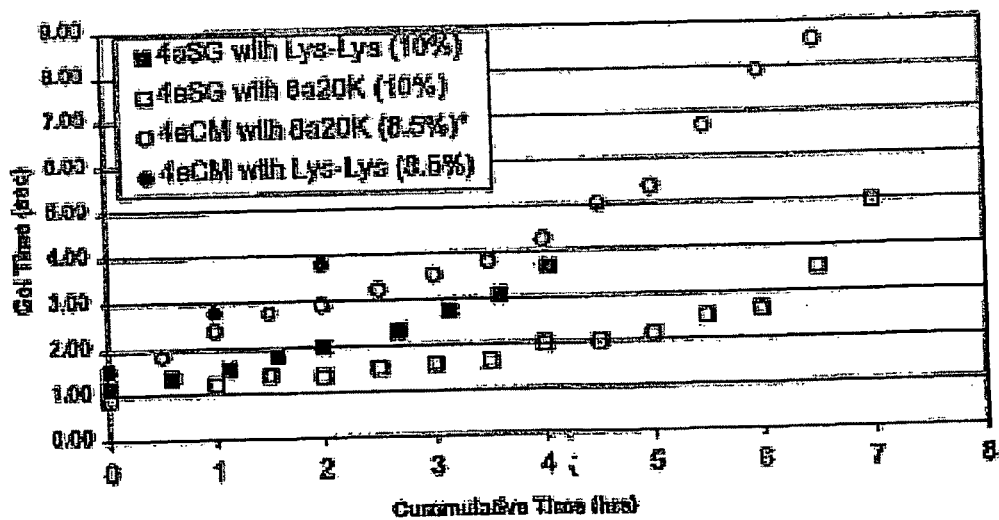
FIG. 24 depicts the effect of electrophile pot life on gel time for hydrogels made with dilysine (LL or Lys-Lys), see also Example 16.
Figure 25:
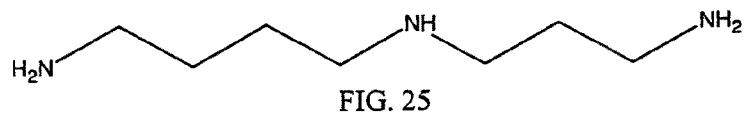
FIG. 25 depicts a chemical structure for spermidine.
Figure 26:
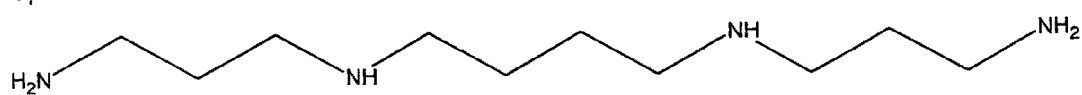
FIG. 26 depicts a chemical structure for spermine.
Figure 27:
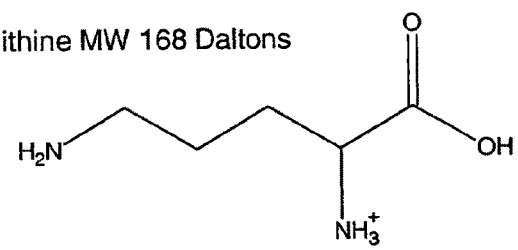
FIG. 27 depicts a chemical structure for ornithine.
Figure 28:
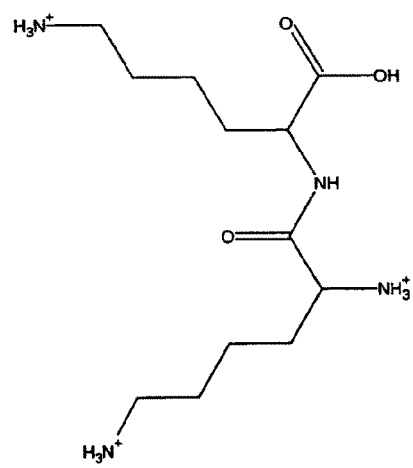
FIG. 28 depicts a chemical structure for dilysine (LL, or Lys-Lys).

Other experiments were performed to determine the "pot life" of the formulations, see FIG. 24. The pot life is a measure of the time that the chemical activity of a solution will be maintained. In general, NHS-esters lose the ability to covalently bind nucleophiles in aqueous solutions. Thus NHS-esters have a limited pot life in aqueous solutions so that it is preferable to store them in a dry form and reconstitute them in solution immediately before use. FIG. 24 depicts the amount of time between reconstitution and use on the x-axis. The gelation time increased as the storage time of the NHS-esters in the aqueous solution increased. The legend of FIG. 24 shows the combinations tested, with 4aSG indicating the four armed PEG-SG-NHS of about 20,000 MW, 4a CM indicating 4 armed 10,000 MW CM-HBA-NHS, Lys-Lys indicating dilysine, 8a20K indicating an eight armed 20,000 MW PEG terminating in primary amines, and the percentages in parentheses indicating solids concentrations in the hydrogels.

Example 17

Degradation and Swelling Properties of Hydrogels Made with Small Molecule Precursors Hydrogels made of trilysine were compared to hydrogels made with Spermine, Spermidine, Ornithine and Dilysine. Various trilysine formulations were made to demonstrate the wide range of characteristics that could be developed using small molecule precursors, including formulations with varying percent solids and pHs.

This Example produced data showing the properties of hydrogels made with a variety of low molecular weight precursors: Tris, trilysine, ornithine, spermidine, dilysine, and spermine, having structures depicted in FIGS. 12, 11, 27, 25, 28, and 26, respectively. Hydrogels of these compositions were made essentially as described in Example 13, using four armed 10,000 MW SG-PEG as the electrophile. The solution pH of each nucleophile was further adjusted to pH 10.2, or as indicated. The solids concentration for each hydrogel was 8.5%, or as indicated, and the electrophile: nucleophile stoichiometric ratio was kept constant at 1:1. The formulations were tested for gelation time, swelling, and degradation essentially as described in Example 13.

Other experiments (not described herein) show that the secondary amines of spermine and spermidine essentially do not participate in covalent bonding with the electrophiles so that they have a nucleophilic functionality of 2. Apparently, since spermine and spermidine are long in length compared to the other small molecules tested, they make hydrogels that have properties somewhat different from hydrogels made with trilysine, Tris, dilysine, and ornithine.

When the pH of the formulation solution used to make trilysine hydrogels was increased, gel times and disappearance times decreased while swelling increased. As the percent solids was increased, gel times were faster while swelling and disappearance times increased.

Figure 29:
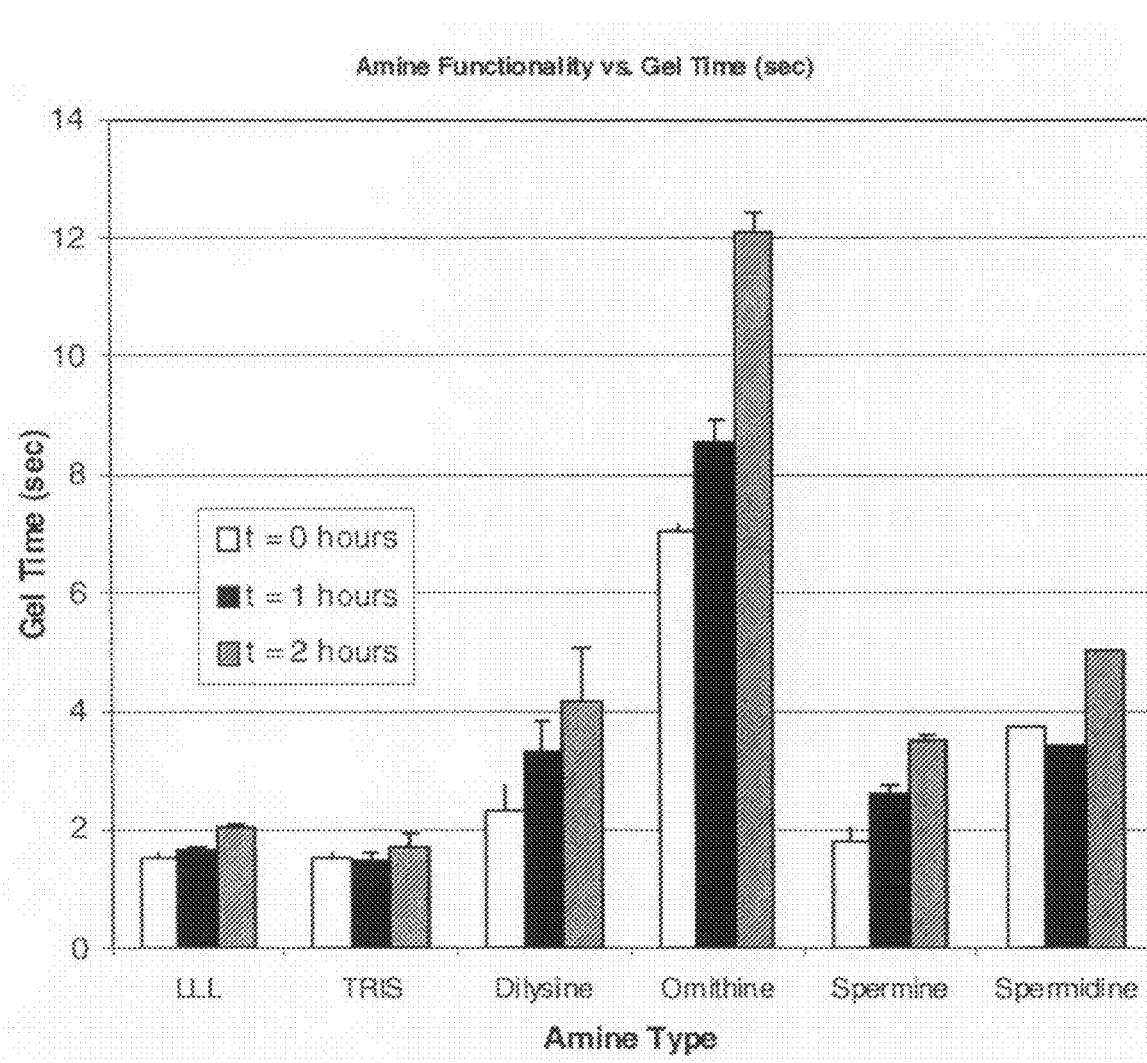
FIG. 29 is a bar graph of gelation time as a function of the number of reactive amines per nucleophile, see also Example 17.

FIG. 29 depicts the gelation times for the hydrogels at 1 and 2 hours after reconstitution of the precursors into solution. LLL denotes trilysine. Trilysine has four amines, Tris and dilysine have three amines, and ornithine, spermine, and spermidine have two amines.

Figure 30:
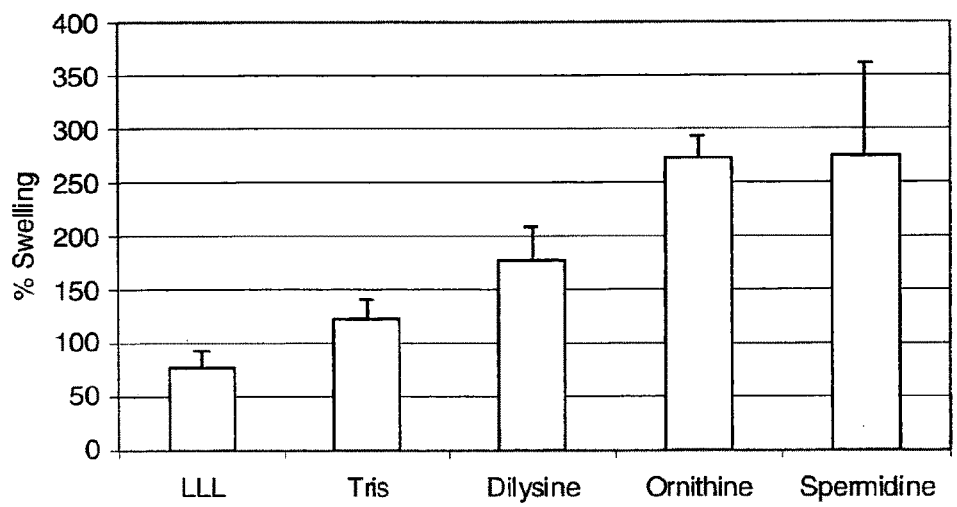
FIG. 30 is a bar graph of swelling as a function of the number of reactive amines per nucleophile, see also Example 17.

FIG. 30 depicts swelling data for the hydrogels made with small molecule precursors. Swelling also showed a trend with functionality of the low molecular weight nucleophilic precursor. As the functionality of the nucleophilic precursor increased, the network was less able to expand. The linear molecules act as chain extenders and do not add to the crosslinking density of the network. The spermine samples at 24 hours were so loose that their swelling could not be measured, apparently due to degradation of the hydrogel.

Figure 31:
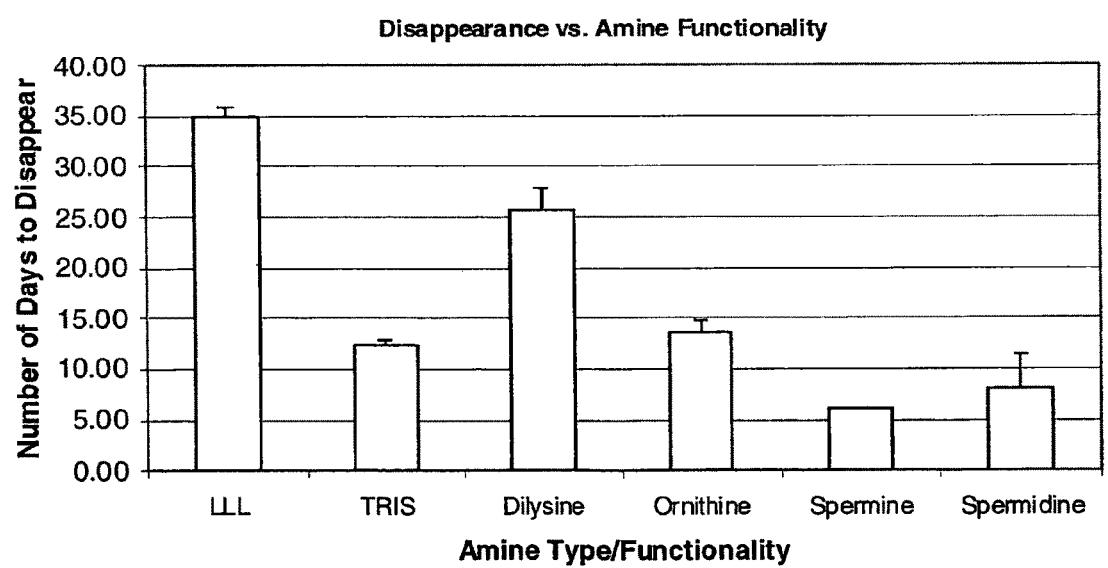
FIG. 31 is a bar graph of degradation time as a function of the number of reactive amines per nucleophile, see also Example 17.

FIG. 31 depicts the degradation of hydrogels made with low molecular weight amines as a function of the number of amines. Generally, hydrogels made with small molecules having a greater amine functionality required longer times to degrade compared to hydrogels made with small molecules having a lower amine functionality, with the exception of hydrogels made with Tris, which degraded more quickly than other hydrogels having three or four amines.

Figure 32:
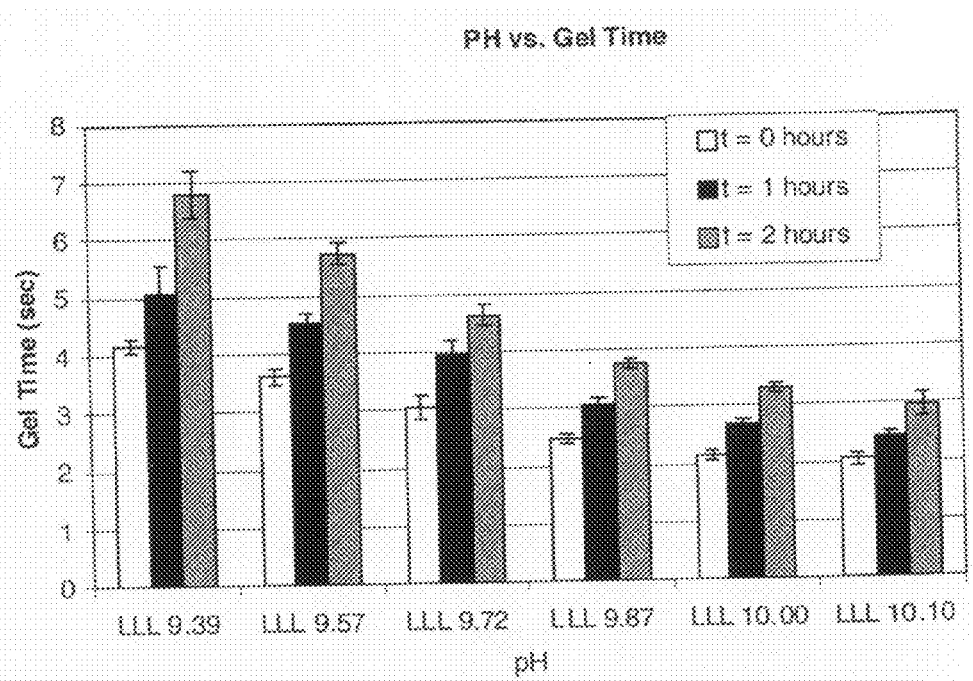
FIG. 32 is a bar graph of gelation time as a function of pH, see also Example 17.

FIG. 32 depicts the gelation time for trilysine as a function of the pH of the formulation solution. In general, an increase of the pH of the solution containing the precursors in the range between about 9 and about 10 caused a decrease in gelation time. Also, an increase in the time between reconstitution of the electrophile in aqueous solution and the formation of the hydrogel caused a decrease in gelation time.

Figure 33:
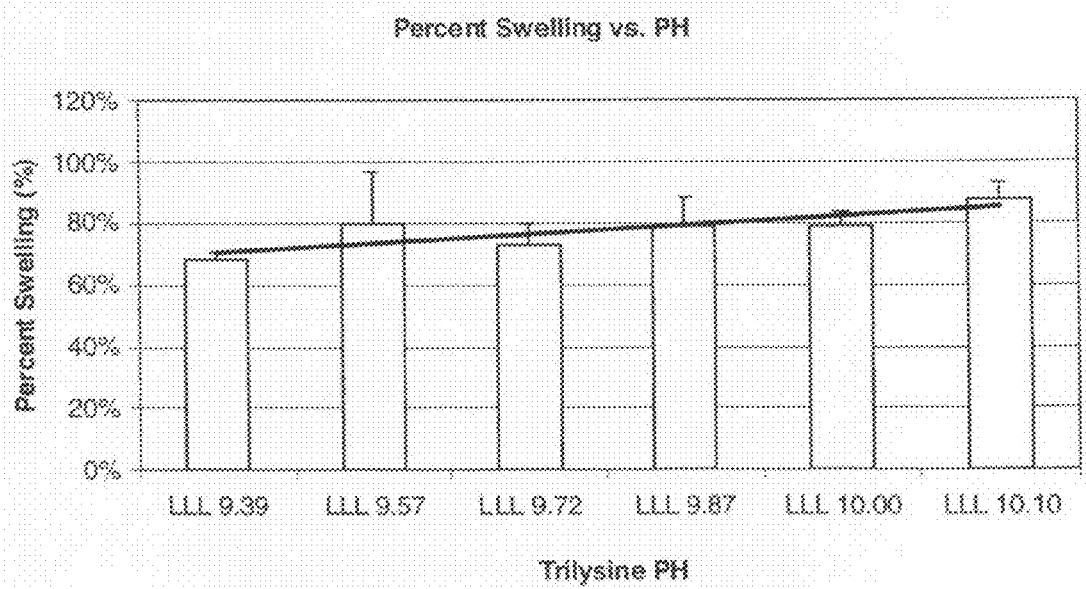
FIG. 33 is a bar graph of swelling as a function of pH, see also Example 17.

FIG. 33 depicts the relationship of swelling as a function of the pH of the formulation solution. As the pH of the formulation solution was increased from about 9 to about 10, the swelling of the resultant hydrogels increased.

Figure 34:
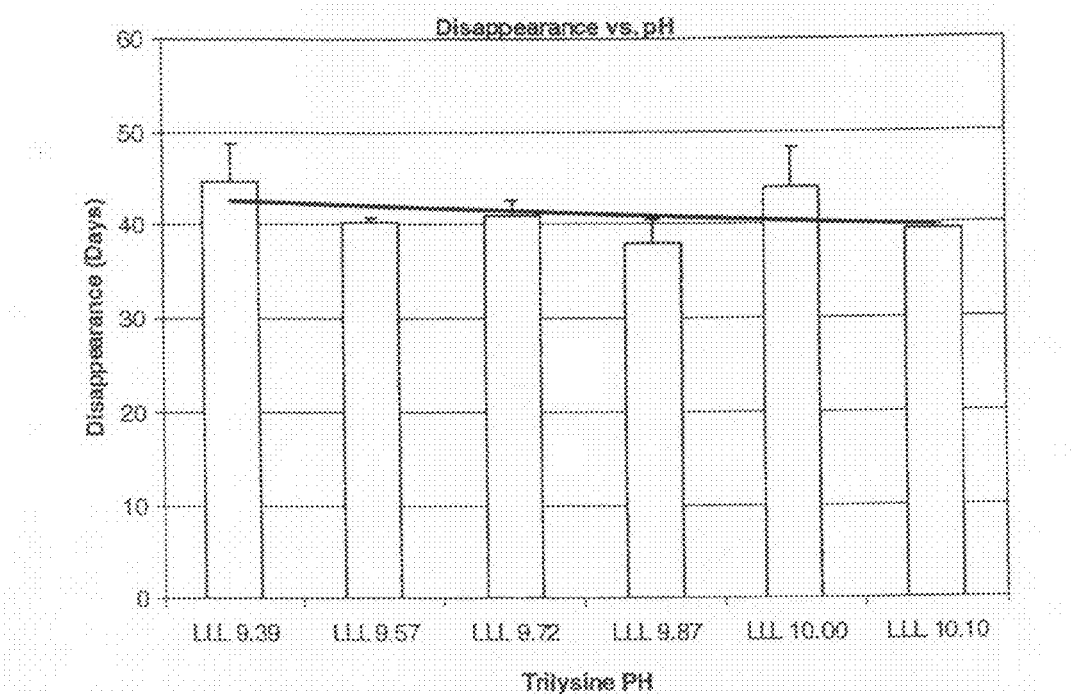
FIG. 34 is a bar graph of degradation as a function of pH, see also Example 17.
Figure 35:
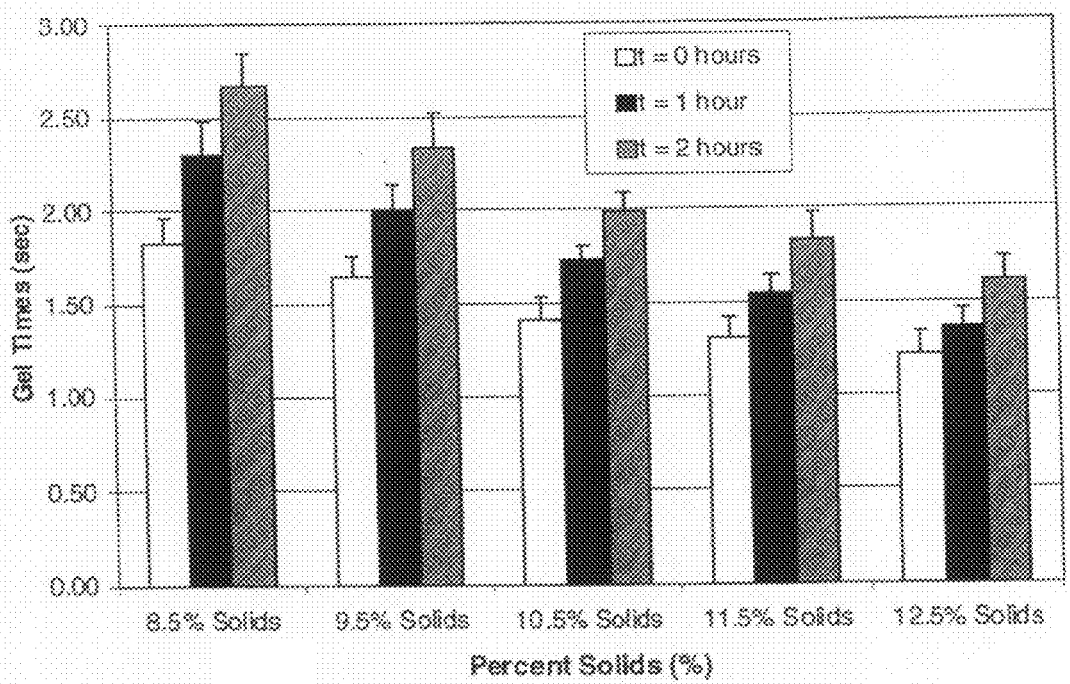
FIG. 35 is a bar graph of gel time as a function of solids and electrophilic pot life, see also Example 17.
Figure 36:
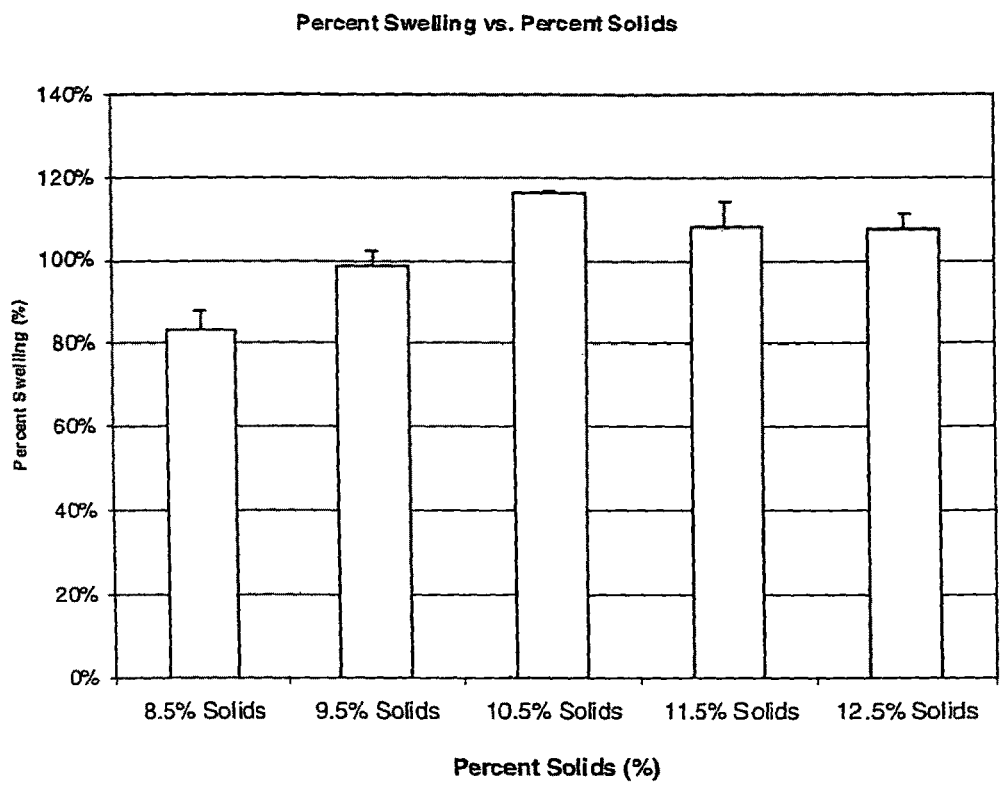
FIG. 36 is a bar graph of swelling as a function of solids content, see also Example 17.
Figure 37:
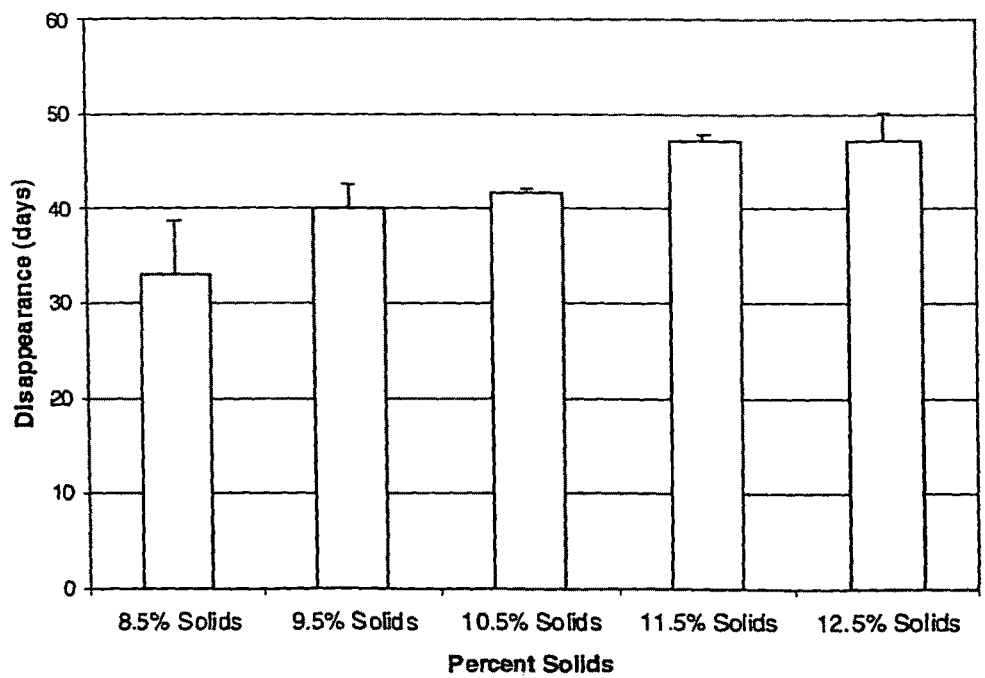
FIG. 37 is a bar graph of degradation as a function of solids and electrophilic pot life, see also Example 17.
Figure 38:
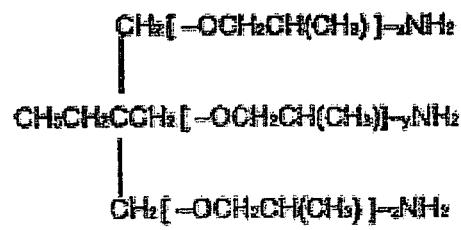
FIG. 38 depicts the chemical structure of JEFFAMINE®.

FIG. 34 depicts the degradation rate of hydrogels as a function of pH. FIG. 35 depicts the gelation time as a function of the total percent solids and the formulation solution pot life. Gelation time decreased as the percent solids in the formulation solution increased from about 8 to about 13 percent. FIG. 36 depicts the swelling of hydrogels formed from trilysine as a function of the amount of solids in the formulation solution. FIG. 37 depicts the degradation of hydrogels formed from trilysine as a function of the amount of solids in the formulation solution.

Example 18

This example shows the results of experiments performed with the nucleophiles spermidine, ornithine, JEFFAMINE T-403 (FIG. 38), LUPASOL polyethyleneimine, and trilysine. The electrophile in these experiments was a four-armed 20,000 MW PEG-SG-NHS. Hydrogels of these compositions were gelled and tested for gelation time, swelling, and degradation essentially as described in Example 13. The solution pH of each nucleophile and electrophile was further adjusted to about pH 9.5. The solids concentration for each hydrogel was 12.5%, and the electrophile: nucleophile stoichiometric ratio was kept constant at 1:1.

Figure 39:
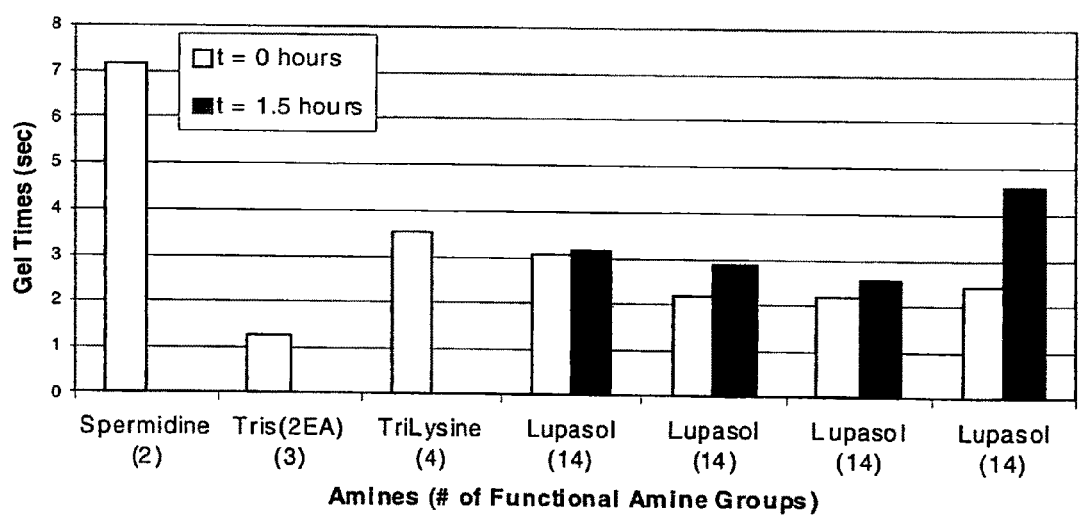
FIG. 39 is a bar graph of the gel time for hydrogels made with LUPASOL®, Tris, LLL, or spermidine, plotted as a function of amine content, see Example 18.
Figure 40:
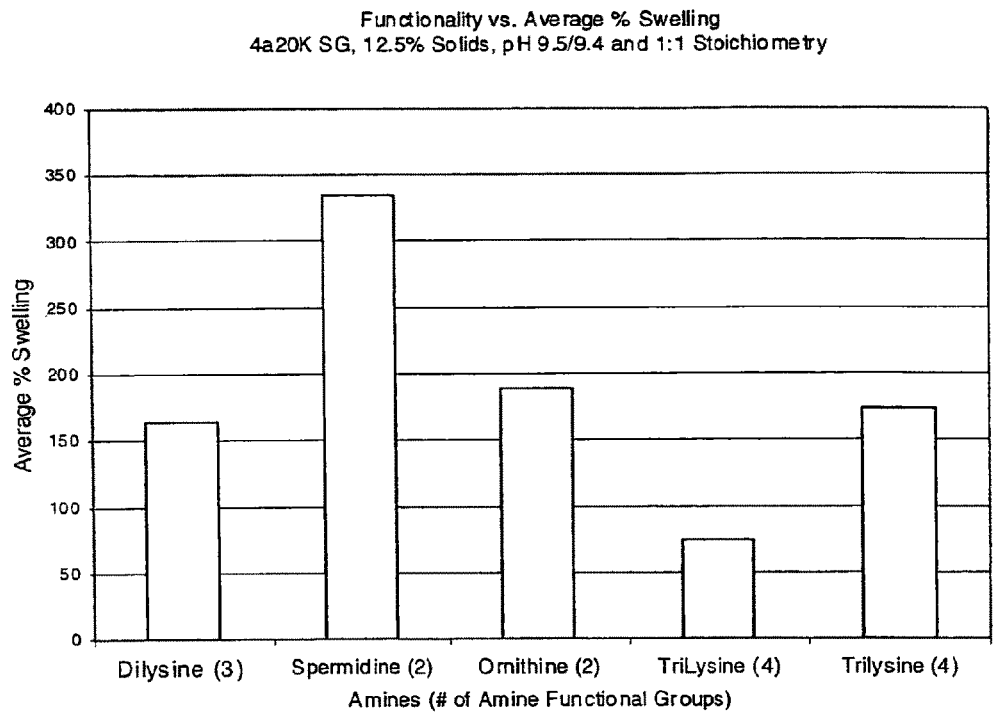
FIG. 40 is a bar graph of the swelling for various hydrogels, see Example 18.
Figure 41:
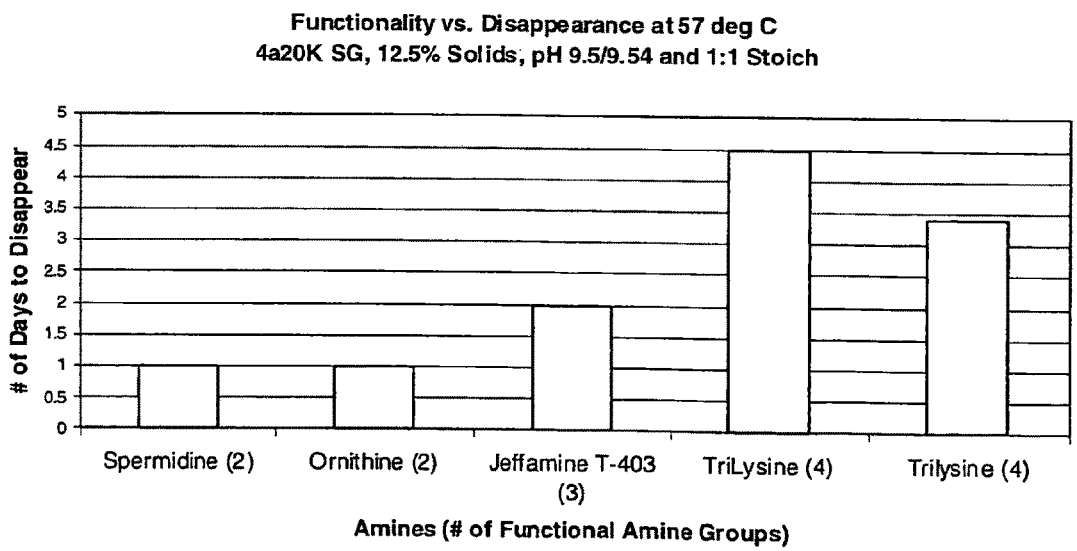
FIG. 41 is a bar graph of the degradation time for various hydrogels, see Example 18.
Figure 42:
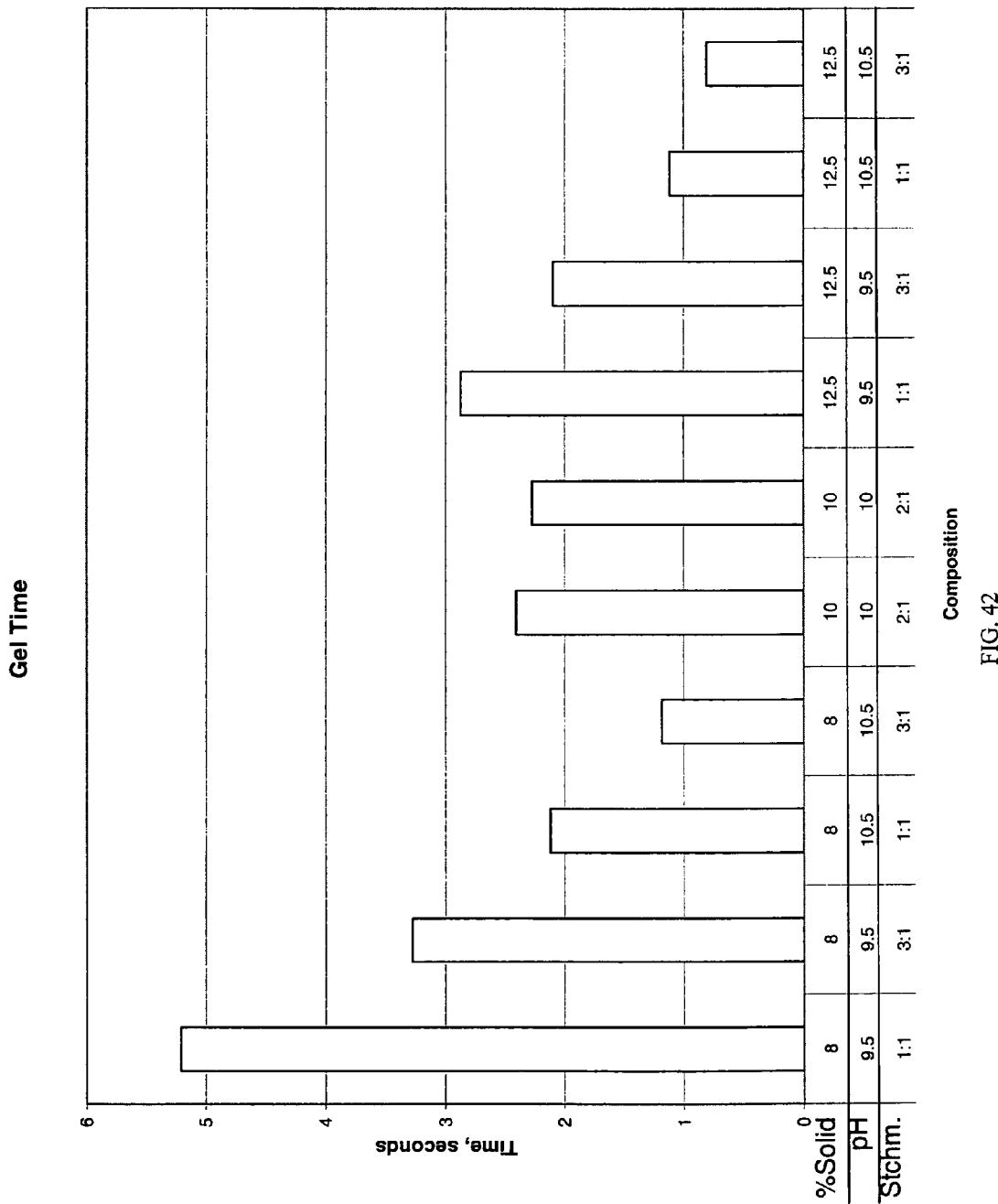
FIG. 42 shows the relationship between gel time and pot life as a function of solids content, pH, and stoichiometry of electrophiles: amines, see Example 19.

FIGS. 39, 40, and 41 show the results for the gelation times, swelling, and degradation, respectively. FIG. 39 shows the gelation time for hydrogels made immediately following placing the electrophile into solution (t=0) and for 1.5 hours after putting the electrophile into solution (t=1.5). FIG. 41 shows accelerated degradation at 57° C.

Example 19

Methods for Using Low Molecular Weight Precursors to Make Hydrogels with Predictable Degradability This example shows methods for choosing formulations to make degradable hydrogels. Included is data that allows the identification of a hydrogel with desired properties of gelation time, water uptake, degradation, and mechanical properties. The electrophile was a 4 armed 20,000 MW PEG-SG-NHS (Shearwater Polymers). The nucleophile was trilysine (Bachem). Hydrogels of these compositions were gelled and tested for gelation time, swelling, and degradation essentially as described in Example 13. The pH, solids concentration, and stoichiometry of nucleophile:electrophile were controlled as indicated. FIGS. 42, 43, 44, and 45 show the gelation time, swelling, degradation, and modulus, respectively, of the hydrogels, with the ratios indicating nucleophile:electrophile stoichiometric (Stchm.) ratios, and the pH and solids content being as indicated.

Figure 43:
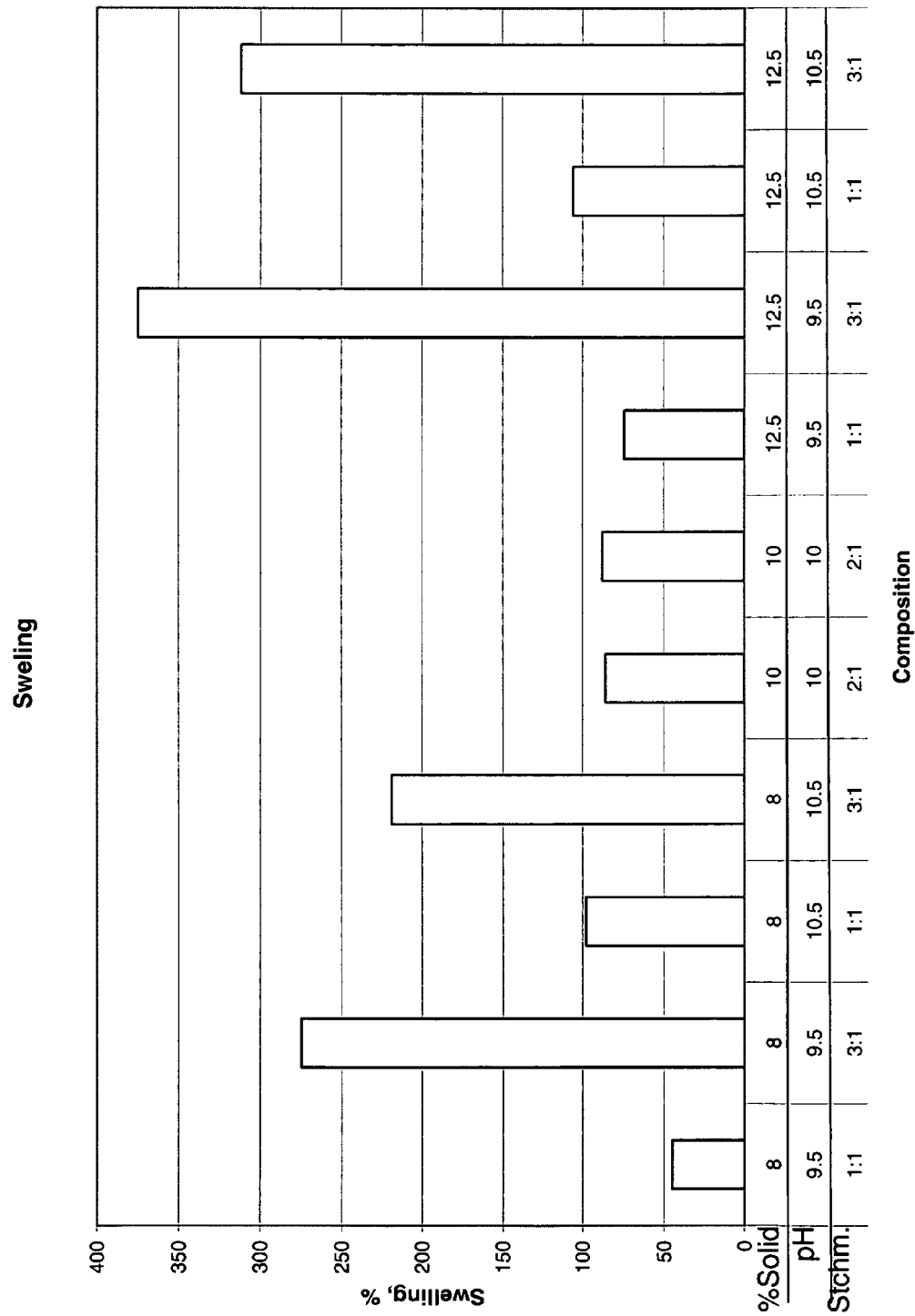
FIG. 43 shows the relationship between swelling and solids content, pH, and stoichiometry of electrophiles: amines, see Example 19.
Figure 44:
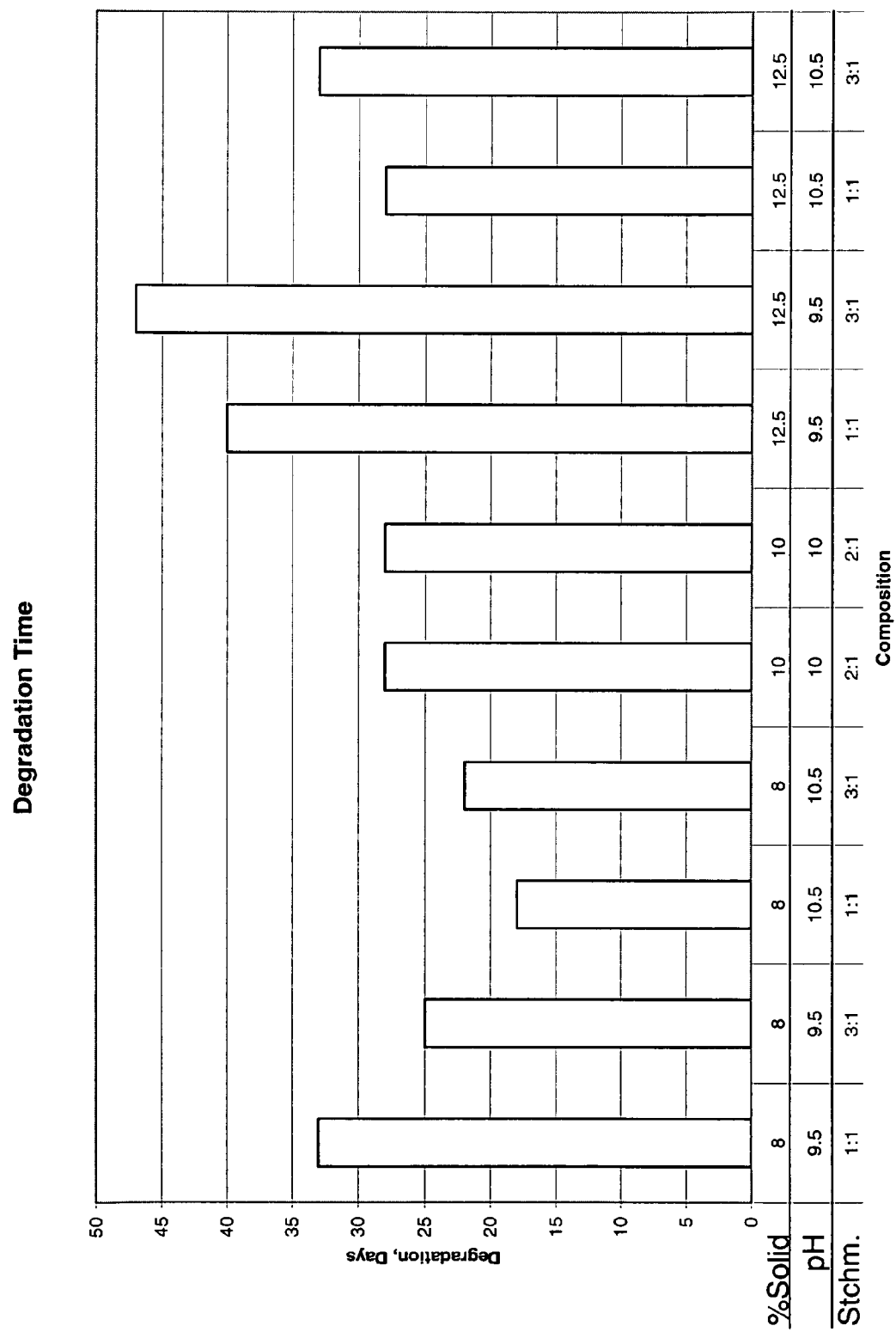
FIG. 44 shows the relationship between degradation and solids content, pH, and stoichiometry of electrophiles: amines, see Example 19.
Figure 45:
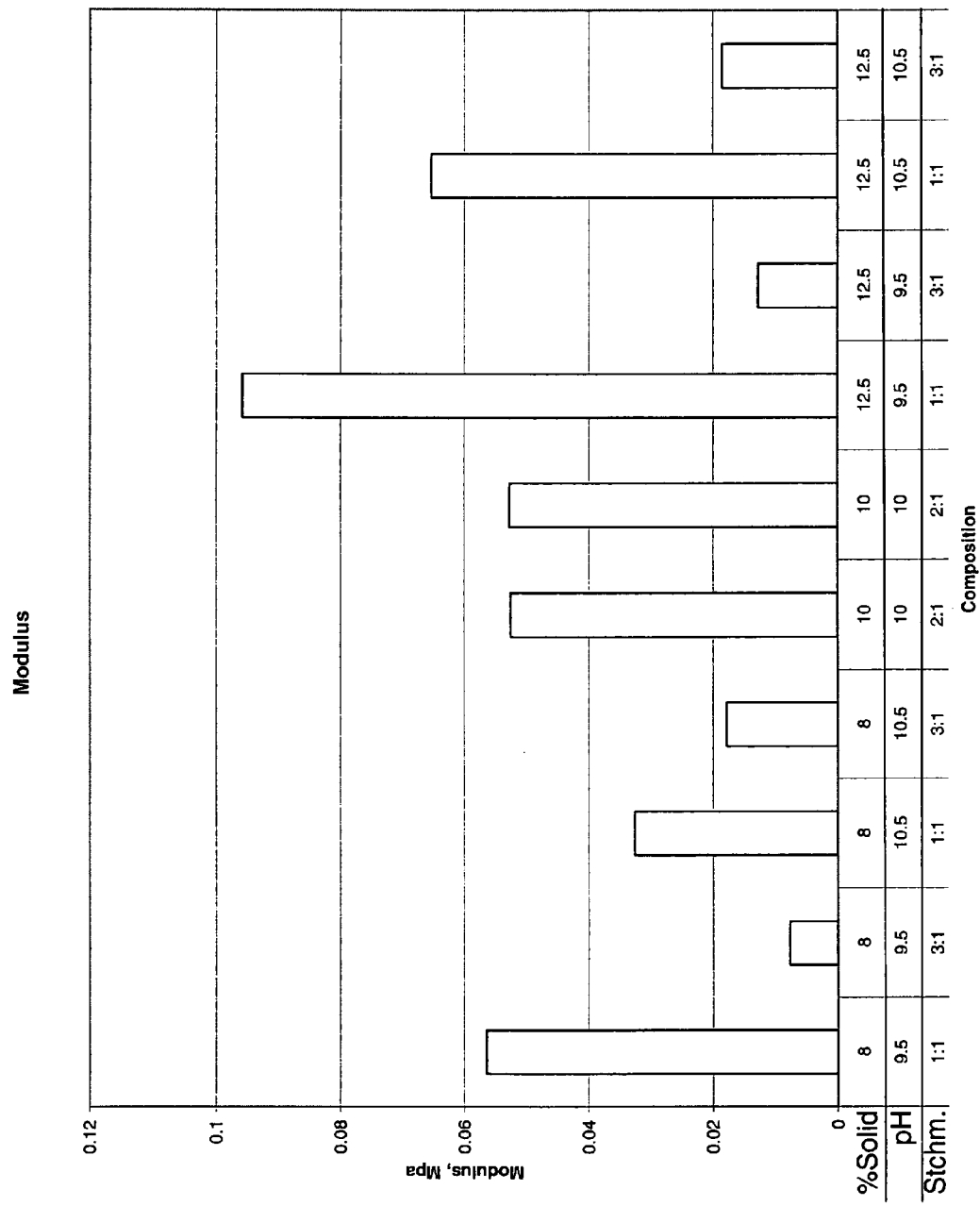
FIG. 45 shows the relationship between modulus and solids content, pH, and stoichiometry of electrophiles:amines, see Example 19.

To illustrate the identification process, a user that desired to identify a formulation with a gelation time of less than 2.5 seconds, less than 100% water uptake, an in-vitro degradation time of four weeks or less, and a high modulus would be able to review the indicated Figures and use FIG. 43 to eliminate all 3:1 nucleophile to electrophile stoichiometry samples since they would fail the water uptake criterion and because, as demonstrated in FIG. 45, they had a lower modulus than the 1:1 ratio hydrogels, which had a modulus of over 30 kPa. The user could refer to FIG. 42 to ascertain that 1:1 ratio gels that satisfy the gelation time criterion have solids concentrations between 12.5% and 8.0%. Referring to FIG. 44, the degradation rates of a hydrogel can be controlled, in part, by altering the pH of the formulation solutions, so that the pH between more than about 9.5 to about 10.5 would be suitable.

Example 20

Hydrogels Made with Dilysine as the Low Molecular Weight Precursor

This example shows the properties of hydrogels made with various formulations of electrophiles in combination with Dilysine. The electrophiles were four armed 10,000 molecular weight PEG-SG (4a10k PEG-SG), four armed 20,000 molecular weight PEG-SG (4a20k PEG-SG), two armed 10,000 molecular weight PEG terminated in N-hydroxy succinimidyl carbonates (2a10k PEG-SC), and eight armed 10,000 molecular weight PEG terminated in N-hydroxy succinimidyl carbonates (8a10k PEG-SC). The hydrogels were made and tested essentially as described in Example 13, with dilysine (ICN Biomedical) being dissolved in 0.1 M pH 10.0 borate buffer and the electrophiles being dissolved in 0.01 M pH 4.0 phosphate buffer.

Table 6 shows the gel times for dilysine precursors reacted at pH 10.0 with various electrophiles mixed to achieve 12.5% solids concentrations. Table 6 shows the effect of the time lapse between reconstitution of the electrophiles of Table 6 and their gelation with dilysine. Table 6 shows the swelling of hydrogels made with various electrophiles reacted with dilysine at pH 10.0 and 12.5% solids, with 4a indicating four arms, 10k indicating a molecular weight of about 10,000.

TABLE 6

Gel times for dilysine precursors reacted with various electrophilic precursors

| Electrophile Formulation | Average Initial Gel Time (seconds) |
|---|---|
| 4a10k PEG-SG | 3.19 ± 0.03 |
| 4a20k PEG-SG | 2.76 ± 0.04 |
| 2a10k PEG-CM-HBA-NHS | No gel formed |
| 8a10k PEG-CM-HBA-NHS | 1.85 ± 0.04 |

TABLE 7

The effect of the time lapse between reconstitution of the electrophiles of Table 6 from the powder form to aqueous solution and their gelation with dilysine

| Electrophile | Cumulative time since reconstitution (hours) | Average Gel Time (Seconds ± Std. Dev.) |
|---|---|---|
| 4a10k PEG-SG | 0 | 3.19 ± 0.03 |
| | 0.5 | 3.75 ± 0.02 |
| | 1.0 | 3.19 ± 0.03 |
| | 1.5 | 5.11 ± 0.04 |
| 4a20k PEG-SG | 0 | 2.76 ± 0.04 |
| | 0.5 | 2.96 ± 0.04 |
| | 1.0 | 3.38 ± 0.04 |
| | 1.5 | 3.52 ± 0.04 |
| 8a10k PEG-SC | 0 | 1.85 ± 0.04 |
| | 0.5 | 2.68 ± 0.01 |
| | 1.0 | 2.85 ± 0.06 |
| | 1.5 | 3.52 ± 0.05 |

TABLE 8 comparison of swelling for hydrogels of Table 6 made with various electrophiles and dilysine at pH 10.0 in 12.5% solids.

| FORMULATION | AVERAGE % SWELLING |
|---|---|
| 4a10k PEG-SG | 70.6 ± 10.8 |
| 4a20k PEG-SG | 165.5 ± 8.8 |
| 2a10k PEG-CM-HBA-NHS | No gel |
| 8a10k PEG-CM-HBA-NHS | 45.1 ± 0.6 |

TABLE 9

Times to degrade gels of Table 6 in vitro.

| FORMULATION | Time (days) |
|---|---|
| 4a10k PEG-SG | 32 |
| 4a20k PEG-SG | 28 |
| 2a10k PEG-CM-HBA-NHS | No gel |
| 8a10k PEG-CM-HBA-NHS | Less than 28 |

Example 21

Physical Properties of Selected Hydrogels

This Example shows physical properties of hydrogels obtained by mixing certain combinations of electrophiles and nucleophiles. Procedures for making and testing the hydrogels were as per Example 13 unless otherwise indicated. The electrophiles that were tested were four armed 10,000 molecular weight PEG-SG (4a10k PEG-SG), four armed 20,000 molecular weight PEG-SG (4a20k PEG-SG), and 10,000 molecular weight, four armed CM-HBA-NHS PEG (4a10k CM-HBA-NHS). The nucleophile was trilysine (LLL) or 8 armed 20,000 molecular weight PEG amine (8a20k amine). The electrophile: nucleophile ratio was approximately 1:1, the pH of the mixture was 9.5, the electrophiles were reconstituted in pH 4.0 0.01 molar phosphate buffer.

In general, the 4a20k PEG-SG exhibited significantly higher energy to failure than the other two electrophiles. The modulus of the 4a20k PEG-SG was the lowest at 0.058 MPa, compared to 0.086 for the 4a10k CM-HBA-NHS, and 1.121 MPa for the 4a10k PEG-SG.

While preferred illustrative embodiments of the invention are described above, the embodiments are only examples, and are not intended to limit the scope or spirit of the present disclosure. All patents, patent applications, publications, and journal articles that are referenced herein are hereby incorporated herein by reference to the extent they do not contradict what is explicitly disclosed.

The invention claimed is:

1. A method for making a medical device, the method comprising:
   providing at least a first biocompatible precursor having least two electrophilic functional groups, and providing at least a second biocompatible precursor comprising at least two primary amine functional groups; wherein the first biocompatible precursor and the second biocompatible precursor are resistant to enzymatic degradation and at least one of the first biocompatible precursor or second biocompatible precursor comprises at least one isolated hydrolytically degradable ester group; and
   mixing at least the first biocompatible precursor and the second biocompatible precursor in situ to form a device comprising a crosslinked hydrogel that comprises covalent bonds formed by reaction of the functional groups of the first biocompatible precursor and second biocompatible precursor with each other and further comprising the at least one isolated hydrolytically degradable ester group; wherein the crosslinked hydrogel is resistant to enzymatic degradation, is degradable by hydrolysis of the at least one isolated hydrolytically degradable ester group so that the device is degradable in less than about 180 days, and wherein the second biocompatible precursor has a molecular weight of less than about 2000, wherein the second precursor is a member of the group consisting of ornithine, spermine, spermidine, urea, guanidine, dianmiopimelic acid, diaminobutyric acid, methylornithine, diaminopropionic acid, cystine, lanthionine, cystamine, trioxatridecanediamine, cyclohexanebis(methylamine), tetraethylenepentamine, pentaethylenehexamine, methylenebis(methylcyclohexamine), diaminocyclohexane, n-(2-aminoethyl)-1,3-propanediamine, diaminomethyldipropylamine, iminobispropylamine, bis(hexamethlyene)triamine, triethylenetetramine, bis(aminopropyl)ethylenediamine, bis(2-aminoethyl)-1,3-propanediamine, bis(aminopropyl)propanediamine, diamniomethylpropane, 1,2-diamino-2-methylpropane, 1,3-diaminopentane, dimethylpropanediamine, 2,2-dimethyl 1,3-propanediamine, methylpentanediamine, 2-methyl-1,5 pentanediamine, diaminoheptane, diaminooctane, diaminononane, and diaminododecane.

2. A method for making a medical device, the method comprising:
   providing at least a first biocompatible precursor having least two electrophilic functional groups, and providing at least a second biocompatible precursor comprising at least two primary amine functional groups; wherein the first biocompatible precursor and the second biocompatible precursor are resistant to enzymatic degradation and at least one of the first biocompatible precursor or second biocompatible precursor comprises at least one isolated hydrolytically degradable ester group; and
   mixing at least the first biocompatible precursor and the second biocompatible precursor in situ to form a device comprising a crosslinked hydrogel that comprises covalent bonds formed by reaction of the functional groups of the first biocompatible recursor and second biocompatible precursor with each other and further comprising the at least one isolated hydrolytically degradable ester group; wherein the crosslinked hydrogel is resistant to enzymatic degradation, is degradable by hydrolysis of the at least one isolated hydrolytically degradable ester group so that the device is degradable in less than about 180 days, and wherein the second biocompatible precursor has a molecular weight of less than about 2000, and
   further comprising a third biocompatible precursor reacted with the first biocompatible precursor, wherein the third biocompatible precursor is a member of the group consisting of dilysine, trilysine, tetralysine, and Tris.

3. A method for making a medical device, the method comprising:
   providing at least a first biocompatible precursor having least two electrophilic functional groups, and providing at least a second biocompatible precursor comprising at least two primary amine functional groups; wherein the first biocompatible precursor and the second biocompatible precursor are resistant to enzymatic degradation and at least one of the first biocompatible precursor or second biocompatible precursor comprises at least one isolated hydrolytically degradable ester group; and
   mixing at least the first biocompatible recursor and the second biocompatible precursor in situ to form a device comprising a crosslinked hydrogel that comprises covalent bonds formed by reaction of the functional groups of the first biocompatible precursor and second biocompatible precursor with each other and further comprising the at least one isolated hydrolytically degradable ester group; wherein the crosslinked hydrogel is resistant to enzymatic degradation, is degradable by hydrolysis of the at least one isolated hydrolytically degradable ester group so that the device is degradable in less than about 180 days, and wherein the second biocompatible precursor has a molecular weight of less than about 2000, further comprising a third biocompatible precursor reacted with the first biocompatible precursor, wherein the second biocompatible precursor and the third biocompatible precursor are selected from the group consisting of dilysine, trilysine, tetralysine, and Tris.

4. A kit comprising:
   a first biocompatible precursor having at least two electrophilic functional groups, and a second biocompatible precursor comprising at least two primary amine functional groups, a third biocompatible precursor comprising at least two primary amine functional groups and, an applicator;
   wherein the first biocompatible precursor, the second biocompatible precursor, and the third biocompatible precursor are reactable with each other to form a crosslinked hydrogel, are resistant to enzymatic degradation, and at least one of the first, second, or third biocompatible precursors comprises at least one isolated hydrolytically degradable ester group;
   wherein the applicator is configured to mix at least the first precursor, the second precursor, and the third precursor to form a crosslinked hydrogel in situ comprising covalent bonds formed by reaction of the functional groups of the precursors and further comprising the at least one isolated hydrolytically degradable ester group;
   wherein the hydrogel comprises a sufficient number of the at least one isolated hydrolytically degradable ester groups in the crosslinked hydrogel so that the crosslinked hydrogel is degradable in less than about 180 days, is resistant to enzymatic degradation, and is degradable by hydrolysis of the at least one isolated hydrolytically degradable ester group; and wherein the kit further comprises instructions that comprise directions for making a hydrogel that is degradable in an amount of time, with the amount of time being less than about 180 days.

5. The kit of claim 4 wherein the second biocompatible precursor and the third biocompatible precursor each have a molecular weight of less than about 1000.

6. The kit of claim 4 wherein the amount of time is less than about 90 days.

7. The kit of claim 4 wherein the amount of time is less than about 45 days.

8. The kit of claim 4 wherein the second biocompatible precursor and the third biocompatible precursor are selected from the group consisting of dilysine, trilysine, tetralysine, and Tris.

9. The kit of claim 4 wherein the second biocompatible precursor is a member of the group consisting of ornithine, spermine, and spermidine.

10. A readily degradable material comprising:
a crosslinked biocompatible hydrogel that comprises a products of a reaction between a first biocompatible precursor, a second biocompatible precursor, and a third biocompatible precursor, with at least one of the biocompatible precursors comprising an isolated hydrolytically degradable ester group, wherein the crosslinked hydrogel is resistant to enzymatic degradation and is degradable by hydrolysis of the isolated hydrolytically degradable ester groups, and
with the second biocompatible precursor, before reaction, being chosen from a group consisting of dilysine, trilysine, and tetralysine; and
with the third biocompatible precursor, before reaction, being chosen from the group consisting of Tris, ornithine, spermine, spermidine, urea, guanidine, diamniopimelic acid, diaminobutyric acid, methylornithine, diaminopropionic acid, cystine, lanthionine, cystamine, trioxatridecanediamine, cyclohexanebis(methylamine), tetraethylenepentamine, pentaethylenehexamine, methylenebis(methylcyclohexamine), diaminocyclohexane, n-(2-aminoethyl)-1,3-propanediamine, diaminomethyldipropylamine, iminobispropylamine, bis(hexamethylene)triamine, triethylenetetramine, bis(aminopropyl)ethylenediamine, bis(2-aminoethyl)-1,3-propanediamine, bis(aminopropyl)propanediamine, diamniomethylpropane, 1,2-diamino-2-methylpropane, 1,3-diaminopentane, dimethylpropanediamine, 2,2-dimethyl 1,3-propanediamine, methylpentanediamine, 2-methyl-1,5 pentanediamine, diaminoheptane, diaminooctane, diaminononane, and diaminododecane.

11. A method of making a hydrogel, the method comprising:
providing a first biocompatible precursor having at least two electrophilic functional groups, a second biocompatible precursor comprising at least two primary amine functional groups, a third biocompatible precursor comprising at least two primary amine functional groups; wherein at least one of the first, the second, or the third biocompatible precursors comprises at least one isolated hydrolytically degradable ester group; wherein the first, the second, and the third biocompatible precursors are resistant to enzymatic degradation; and
mixing, in situ, the first biocompatible precursor, the second biocompatible precursor, and the third biocompatible precursor to form a crosslinked hydrogel that comprises covalent bonds formed by reaction of the functional groups of the first, the second, and the third biocompatible precursors, with the hydrogel being resistant to enzymatic degradation and comprising the at least one isolated hydrolytically degradable ester group; wherein the hydrogel comprises a sufficient number of the at least one isolated hydrolytically degradable ester groups in the crosslinked hydrogel so that the crosslinked hydrogel is degradable in less than about 180 days and is degradable by hydrolysis of the at least one isolated hydrolytically degradable ester group.

12. The method of claim 11 wherein the second biocompatible precursor and the third biocompatible precursor each have a molecular weight of less than about 1000.

13. The method of claim 11 wherein the hydrogel is degradable in less than about 90 days.

14. The method of claim 11 wherein the hydrogel is degradable in less than about 45 days.

15. The method of claim 11 wherein the second biocompatible precursor and the third biocompatible precursor are selected from the group consisting of dilysine, trilysine, tetralysine, and Tris.

16. The method of claim 11 wherein the second biocompatible precursor is a member of the group consisting of ornithine, spermine, spermidine, urea, guanidine, diamniopimelic acid, diaminobutyric acid, methylornithine, diaminopropionic acid, cystine, lanthionine, cystamine, trioxatridecanediamine, cyclohexanebis(methylamine), tetraethylenepentamine, pentaethylenehexamine, methylenebis(methylcyclohexamine), diaminocyclohexane,n-(2-aminoethyl)-1,3-propanediamine, diaminomethyldipropylamine, iminobispropylamine, bis(hexamethlyene)triamine, triethylenetetramine, bis(aminopropyl)ethylenediamine, bis(2-aminoethyl)-1,3-propanediamine, bis(aminopropyl)propanediamine, diamniomethylpropane, 1,2-diamino-2-methylpropane, 1,3-diaminopentane, dimethylpropanediamine, 2,2-dimethyl 1,3-propanediamine, methylpentanediamine, 2-methyl-1,5 pentanediamine, diaminoheptane, diaminooctane, diaminononane, and diaminododecane.

17. The kit of claim 4 wherein the second biocompatible precursor is a member of the group consisting of urea, guanidine, diamniopimelic acid, diaminobutyric acid, methylornithine, and diaminopropionic acid.

18. The kit of claim 4 wherein the second biocompatible precursor is a member of the group consisting of cystine, lanthionine, cystamine, trioxatridecanediamine, and cyclohexanebis(methylamine).

19. The kit of claim 4 wherein the second biocompatible precursor is a member of the group consisting of tetraethylenepentamine, pentaethylenehexamine, methylenebis(methylcyclohexamine), diaminocyclohexane, n-(2-aminoethyl)-1,3-propanediamine, diaminomethyldipropylamine, and iminobispropylamine.

20. The kit of claim 4 wherein the second biocompatible precursor is a member of the group consisting of bis(hexamethlyene)triamine, triethylenetetramine, bis(aminopropyl)ethylenediamine, bis(2-aminoethyl)-1,3-propanediamine, bis(aminopropyl)propanediamine, diamniomethylpropane, and 1,2-diamino-2-methylpropane.

21. The kit of claim 4 wherein the second biocompatible precursor is a member of the group consisting of 1,3-diaminopentane, dimethylpropanediamine, 2,2-dimethyl 1,3-propanediamine, and methylpentanediamine.

22. The kit of claim 4 wherein the second biocompatible precursor is a member of the group consisting of 2-methyl-1,5 pentanediamine, diaminoheptane, diaminooctane, diaminononane, and diaminododecane.

* * * * *